United States Patent
Kim et al.

(10) Patent No.: US 10,611,797 B2
(45) Date of Patent: Apr. 7, 2020

(54) PEPTIDE HAVING ANTICANCER ACTIVITY, AND PHARMACEUTICAL COMPOSITION AND DIETARY SUPPLEMENT COMPOSITION FOR PREVENTING AND TREATING CANCER, BOTH OF WHICH CONTAIN SAME AS ACTIVE INGREDIENT

(71) Applicant: IUCF-HYU (INDUSTRY-UNIVERSITY COOPERATION FOUNDATION HANYANG UNIVERSITY), Seoul (KR)

(72) Inventors: Chul Geun Kim, Seoul (KR); Min Young Kim, Incheon (KR); Chan Gil Kim, Chungju-si (KR); Ho Chul Kang, Suwon-si (KR); Ji Hyung Chae, Seoul (KR); Su Jae Lee, Seoul (KR); Eun Jung Baek, Seoul (KR); Chae Ok Yun, Seoul (KR); Jin Won Lee, Seoul (KR); Young Su Lim, Jeonju-si (KR); Je Min Choi, Seoul (KR); Dae Hyun Ha, Seoul (KR); Hyung Sik Won, Chungju-si (KR); Seung Han Son, Incheon (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 0 days.

(21) Appl. No.: 15/563,533

(22) PCT Filed: Mar. 29, 2016

(86) PCT No.: PCT/KR2016/003179
§ 371 (c)(1),
(2) Date: Sep. 29, 2017

(87) PCT Pub. No.: WO2016/159627
PCT Pub. Date: Oct. 6, 2016

(65) Prior Publication Data
US 2018/0086788 A1 Mar. 29, 2018

(30) Foreign Application Priority Data
Mar. 31, 2015 (KR) .................... 10-2015-0045480
Mar. 21, 2016 (KR) .................... 10-2016-0033118

(51) Int. Cl.
| | |
|---|---|
| A61K 38/00 | (2006.01) |
| A61K 9/00 | (2006.01) |
| C07K 7/06 | (2006.01) |
| C07K 7/08 | (2006.01) |
| C07K 14/00 | (2006.01) |
| A23L 33/18 | (2016.01) |
| A23L 33/00 | (2016.01) |

(52) U.S. Cl.
CPC ............ *C07K 7/06* (2013.01); *A23L 33/18* (2016.08); *A23L 33/40* (2016.08); *A61K 9/0056* (2013.01); *C07K 14/00* (2013.01); *A23V 2002/00* (2013.01); *A61K 38/00* (2013.01); *C07K 2319/00* (2013.01); *C07K 2319/10* (2013.01)

(58) Field of Classification Search
CPC ........ A61K 38/00; A61K 9/0056; A61K 9/00; C07K 7/06; C07K 7/08; C07K 14/00; C07K 2319/00; C07K 2319/10; A23L 33/18; A23L 33/00; A23L 33/40
USPC ...... 530/300, 324, 327, 329; 514/19.3, 21.3, 514/21.5, 21.8
See application file for complete search history.

(56) References Cited

U.S. PATENT DOCUMENTS

| | | | | |
|---|---|---|---|---|
| 5,595,756 A | * | 1/1997 | Bally ............... | A61K 9/1272 264/4.1 |
| 2013/0028899 A1 | | 1/2013 | Sarkar et al. | |
| 2017/0290882 A1 | * | 10/2017 | Andronova ....... | A61K 9/0019 |
| 2017/0360955 A1 | * | 12/2017 | Janssen ............ | A61K 47/6849 |

OTHER PUBLICATIONS

Hait WN, "Anticancer drug development: the grand challenges," Nature Reviews, 2010, 9: 253-254.*
Sporn et al, "Chemoprevention of cancer,", Carcinogenesis, 2000, 21(3): 525-530.*
Auerbach et al, "Angiogenesis assays: Problems and pitfalls," Cancer and Metastasis Reviews, 2000, 19: 167-172.*
Gura T, "Systems for Identifying New Drugs Are Often Faulty," Science, 1997, 278: 1041-1042.*
Jain RK, "Barriers to Drug Delivery in Solid Tumors," Scientific American, 1994, 58-65.*

(Continued)

*Primary Examiner* — Julie Ha
(74) *Attorney, Agent, or Firm* — Sughrue Mion, PLLC

(57) ABSTRACT

A peptide binding to transcription factor CP2c, having an activity of preventing and treating cancer and represented by SEQ ID NO: 1: Asn-Tyr-Pro-Gln-Arg-Pro, and a pharmaceutical composition and a dietary supplement composition for preventing and treating cancer, both of which contain the same as an active ingredient are disclosed. When cancer cells are treated with the peptide and the pharmaceutical composition containing the same, the peptide can specifically bind to CP2c by passing, with very high stability, through the cell membrane and can inhibit the DNA binding ability of CP2c, thereby disturbing CP2c-mediated cancer cell-specific transcriptional activity through the inhibition of CP2c activity. Thus, the peptide and pharmaceutical composition containing the same can be effectively used for specifically treating only cancer cells and can be utilized for cancer prevention and as a dietary supplement additive therefor.

12 Claims, 66 Drawing Sheets
Specification includes a Sequence Listing.

(56) References Cited

OTHER PUBLICATIONS

Neidle, Stephen, ed., Cancer Drug Design and Discovery, Elsevier/Academic Press, 2008, 427-431.*
Kim et al., "A DNA immunoprecipitation assay used in quantitative detection of in vitro DNA-protein complex binding", Analytical Biochemistry, 441 (2013) 147-151.
Kang et al., "Identification and characterization of four novel peptide motifs that recognize distinct regions of the transcription factor CP2", FEBS Journal 272 (2005) 1265-1277.
Xu et al., "Characterization of genome-wide TFCP2 targets in hepatocellular carcinoma: implication of targets FN1 and TJP1 in metastasis", Journal of Experimental & Clinical Cancer Research (2015) 34:6.
Santhekadur et al., "The transcription factor LSF: a novel oncogene for hepatocellular carcinoma", Am J Cancer Res 2012; 2(3):269-285.
Grant et al., "Antiproliferative small-molecule inhibitors of transcription factor LSF reveal oncogene addiction to LSF in hepatocellular carcinoma", PNAS, Mar. 20, 2012, vol. 109, No. 12: 4503-4508.
International Search Report for PCT/KR2016/003179, dated Jul. 12, 2016, 6 pages.

* cited by examiner

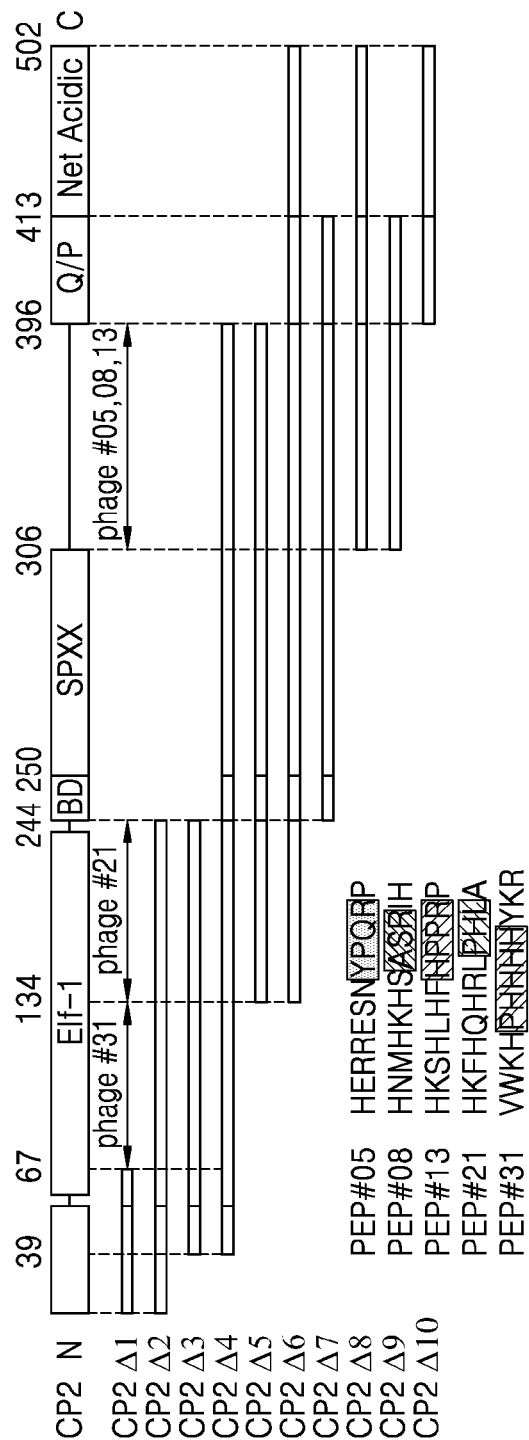
[Fig. 1]

[Fig. 2]
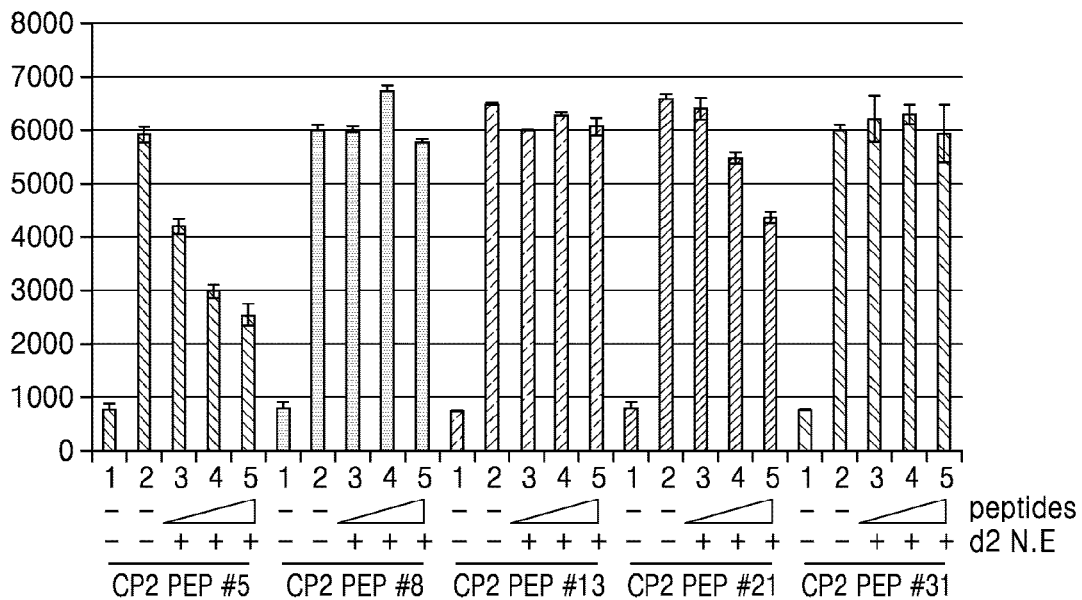
[Fig. 3]
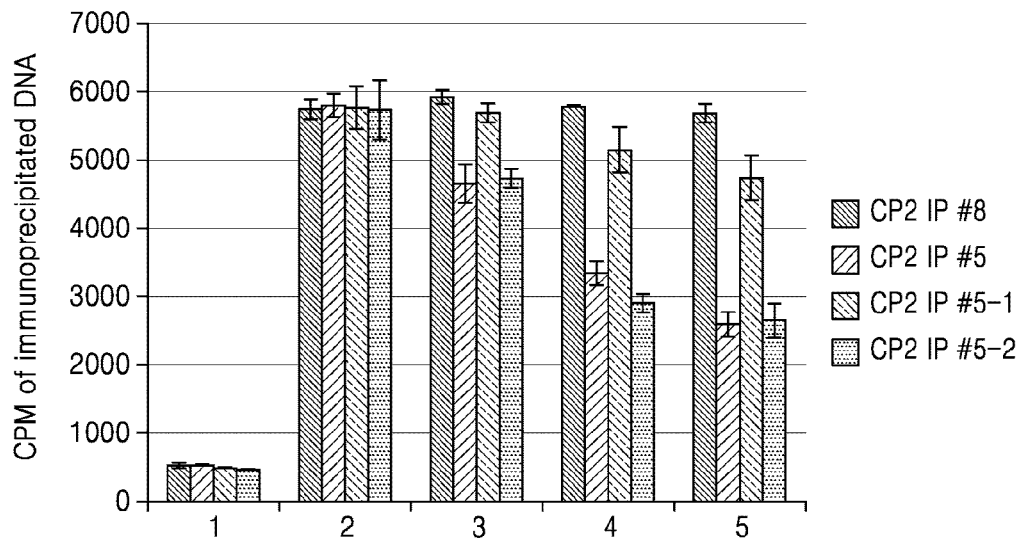

[Fig. 4a]
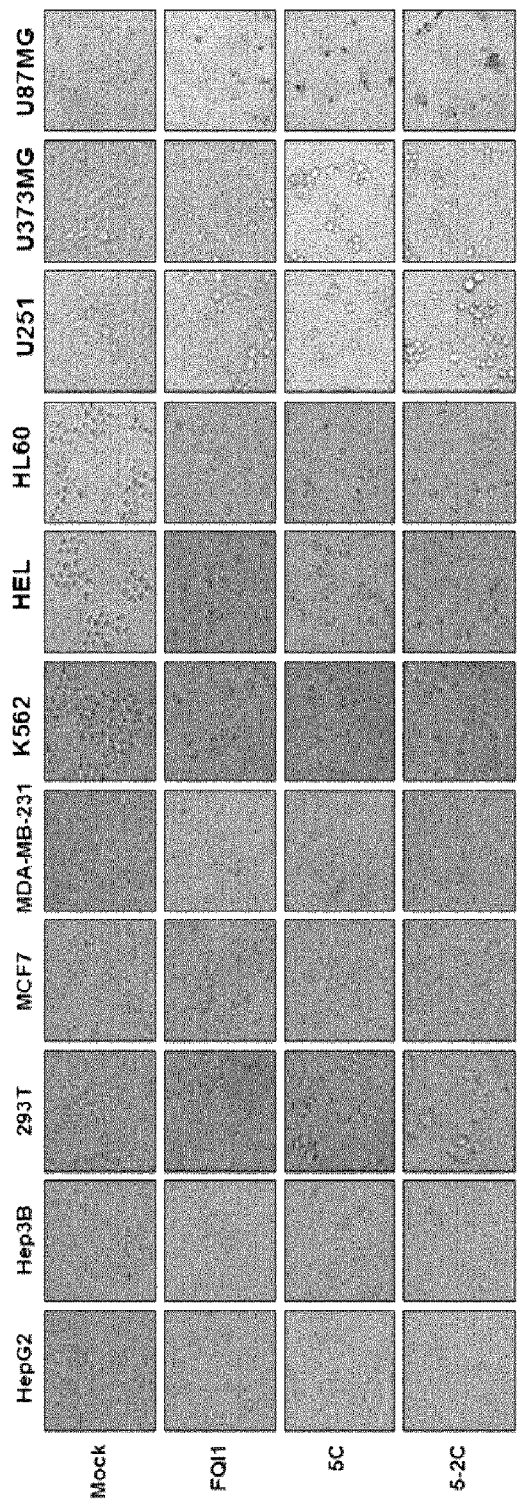

[Fig. 4b]
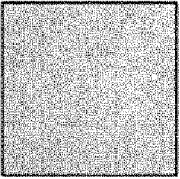

[Fig. 4c]
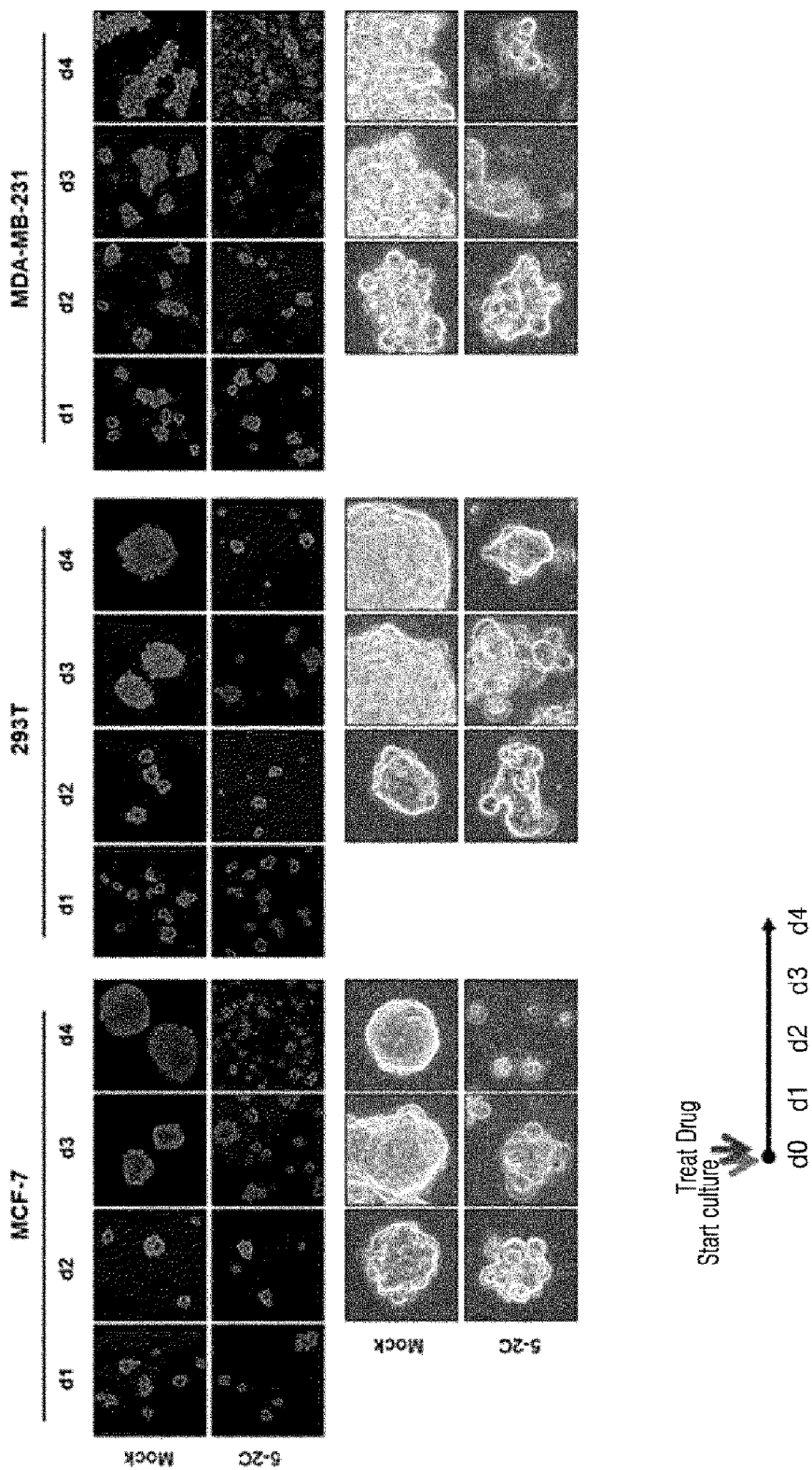

[Fig. 4d]
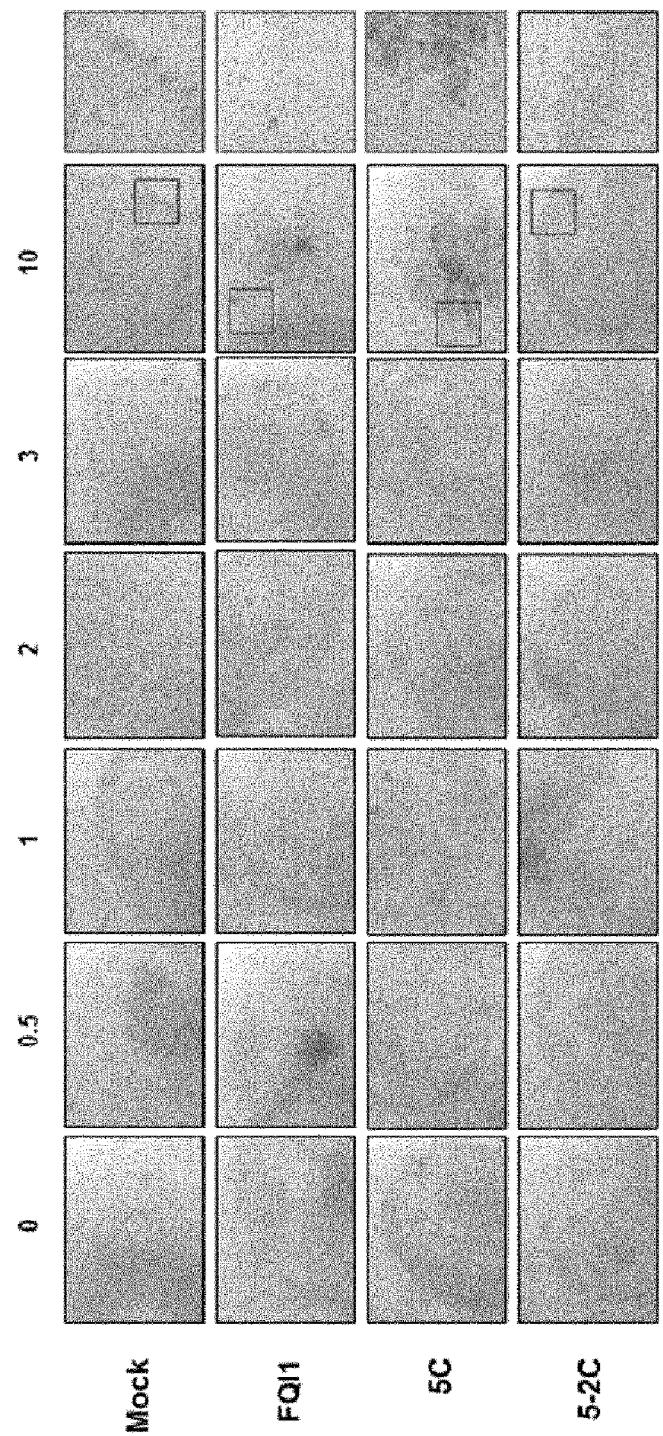
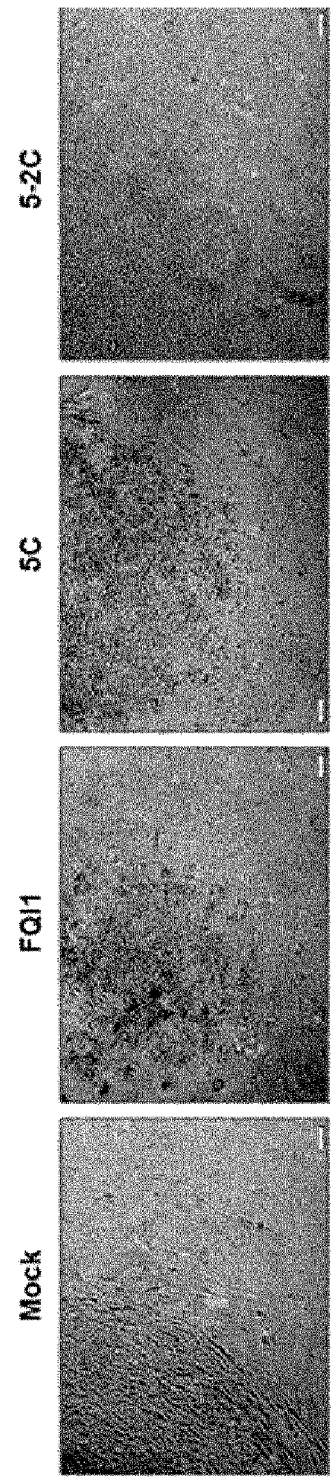

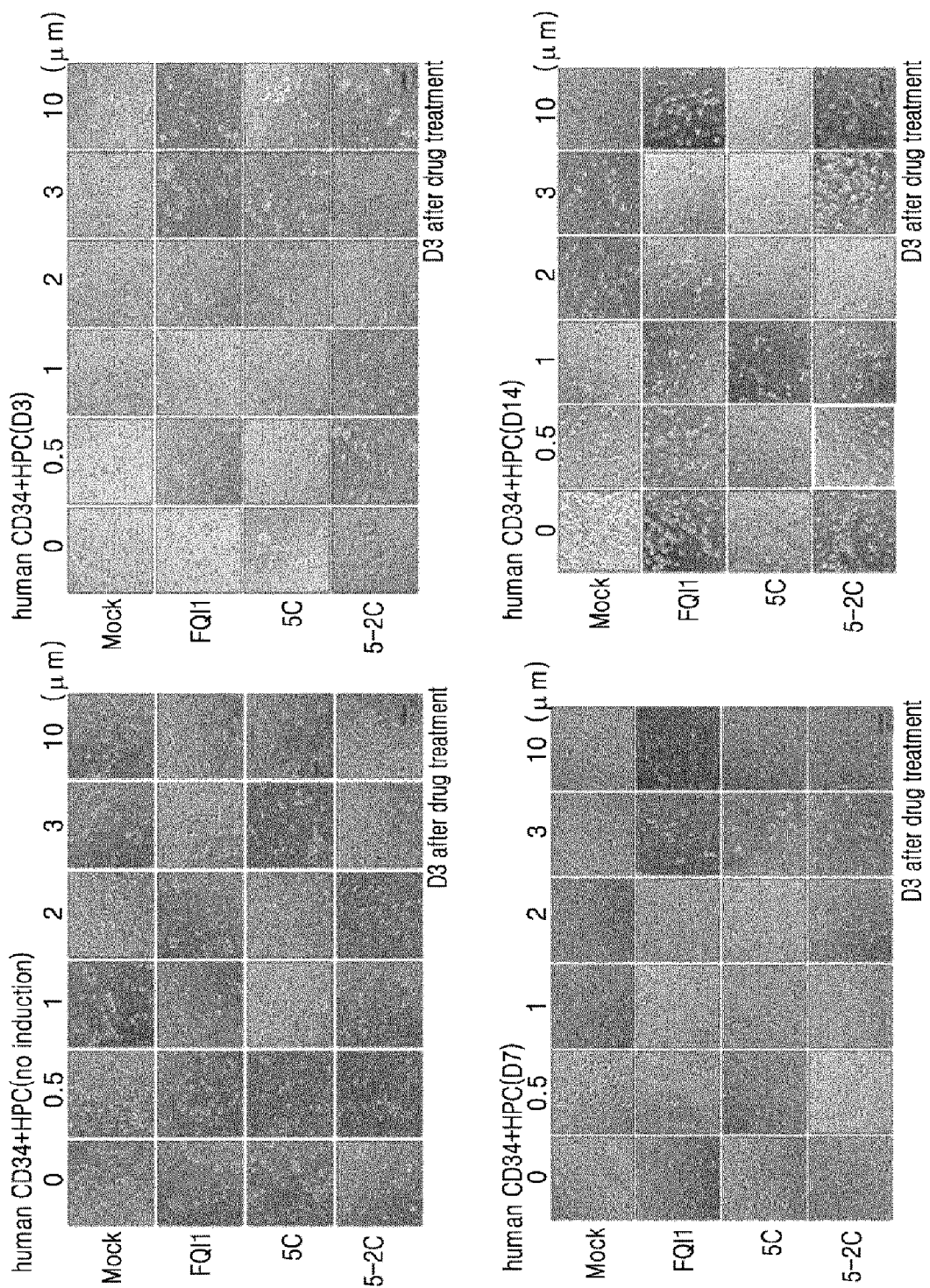
[Fig. 4e]

[Fig. 5a]
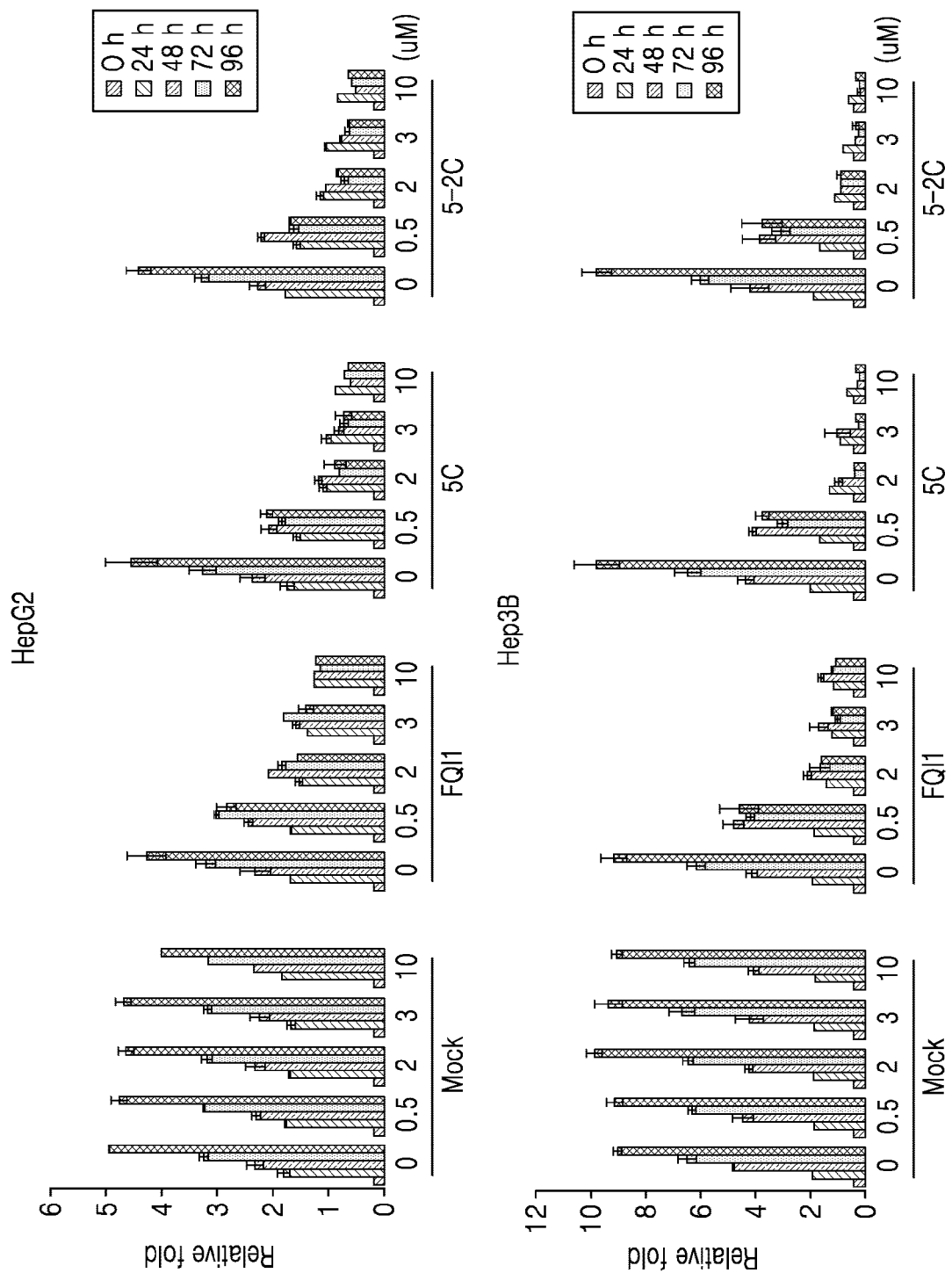

[Fig. 5b]
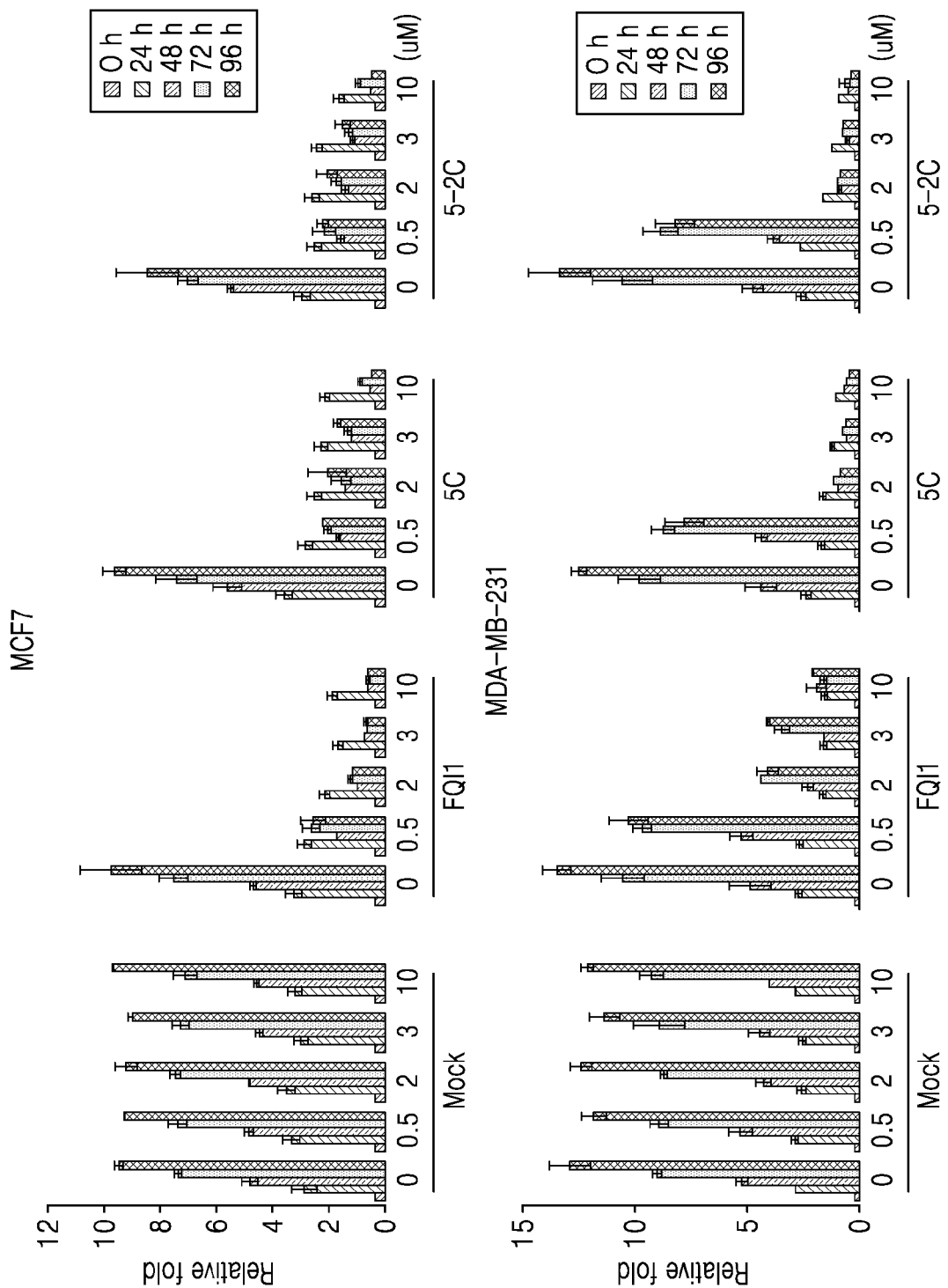

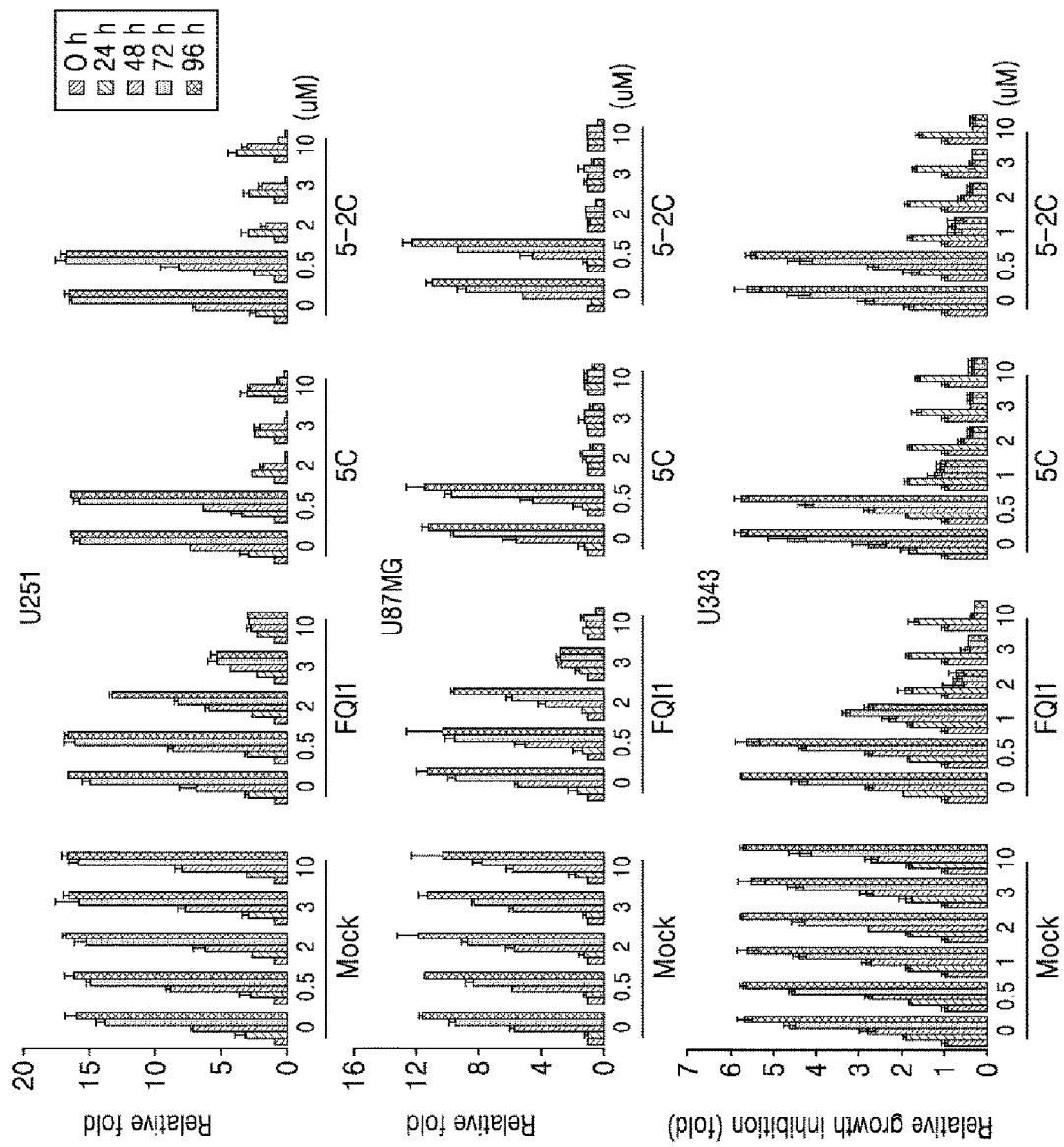
[Fig. 5c]

[Fig. 5d]
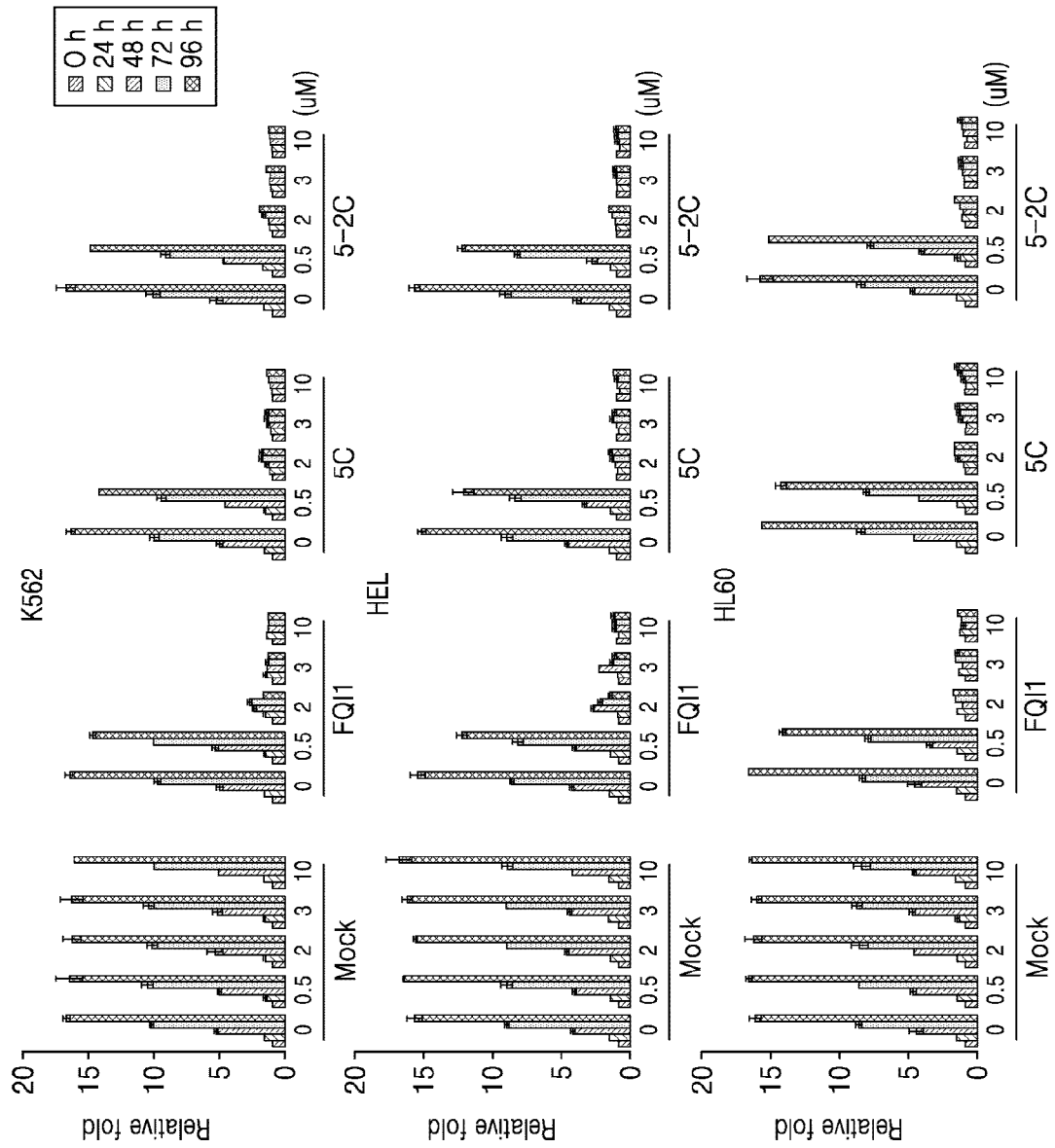

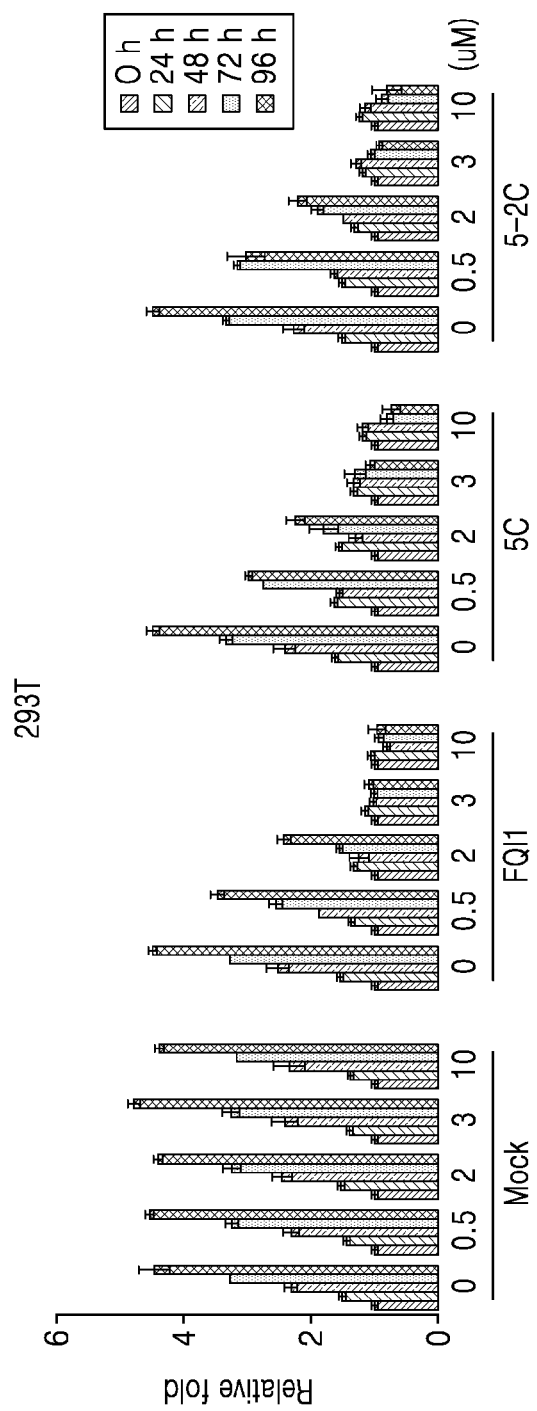
[Fig. 5e]

[Fig. 5f]
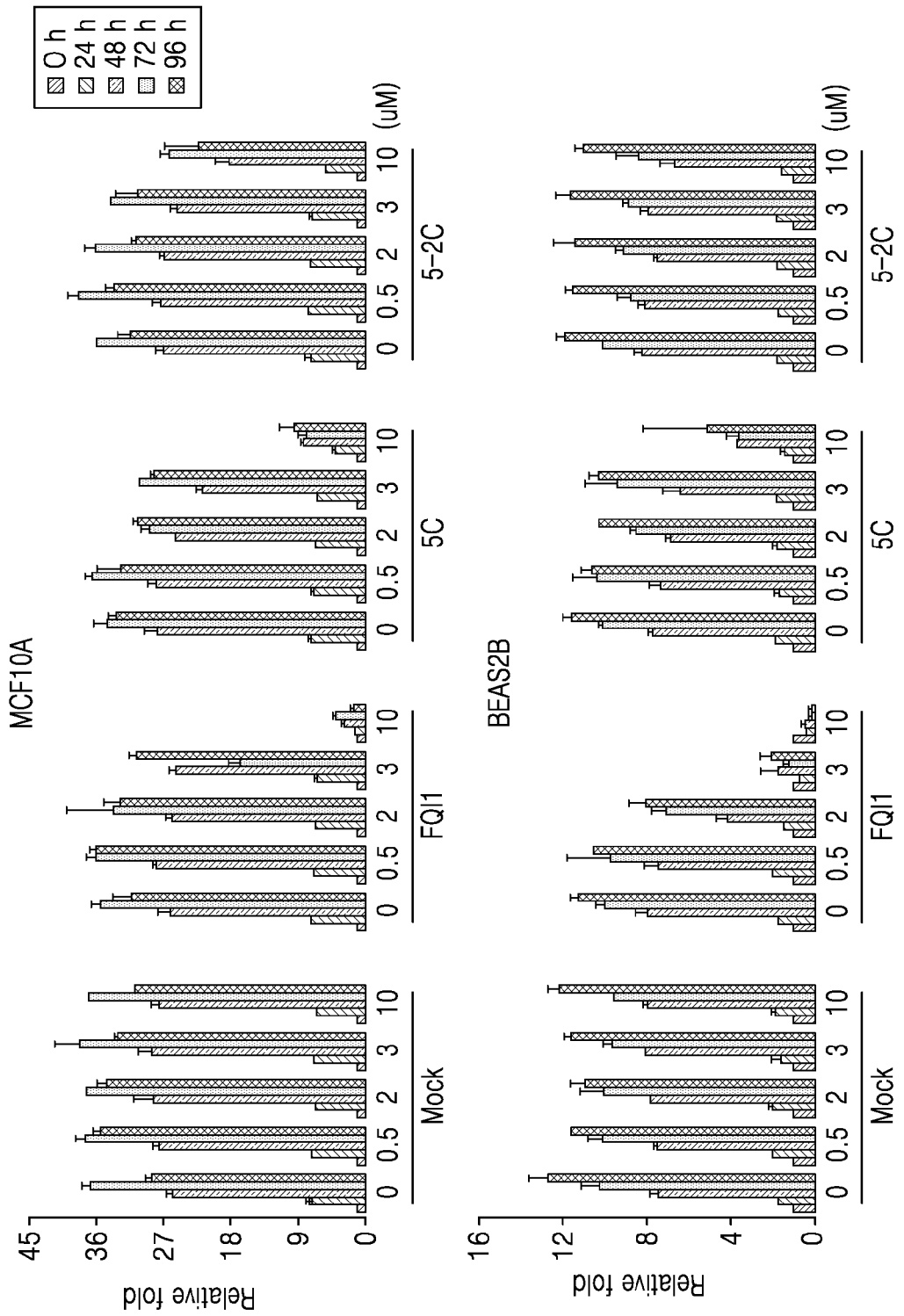

[Fig. 5g]
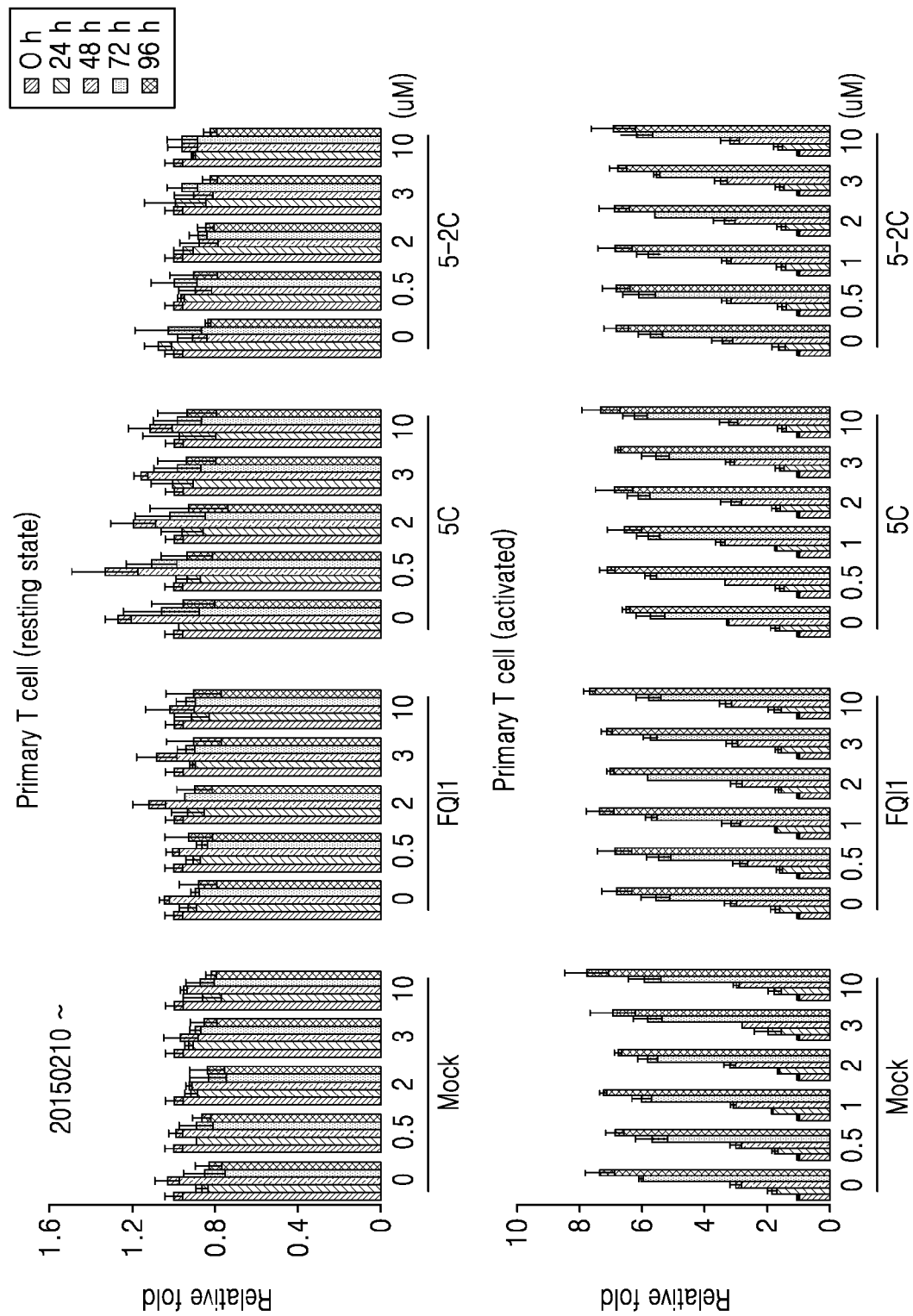

[Fig. 5h]
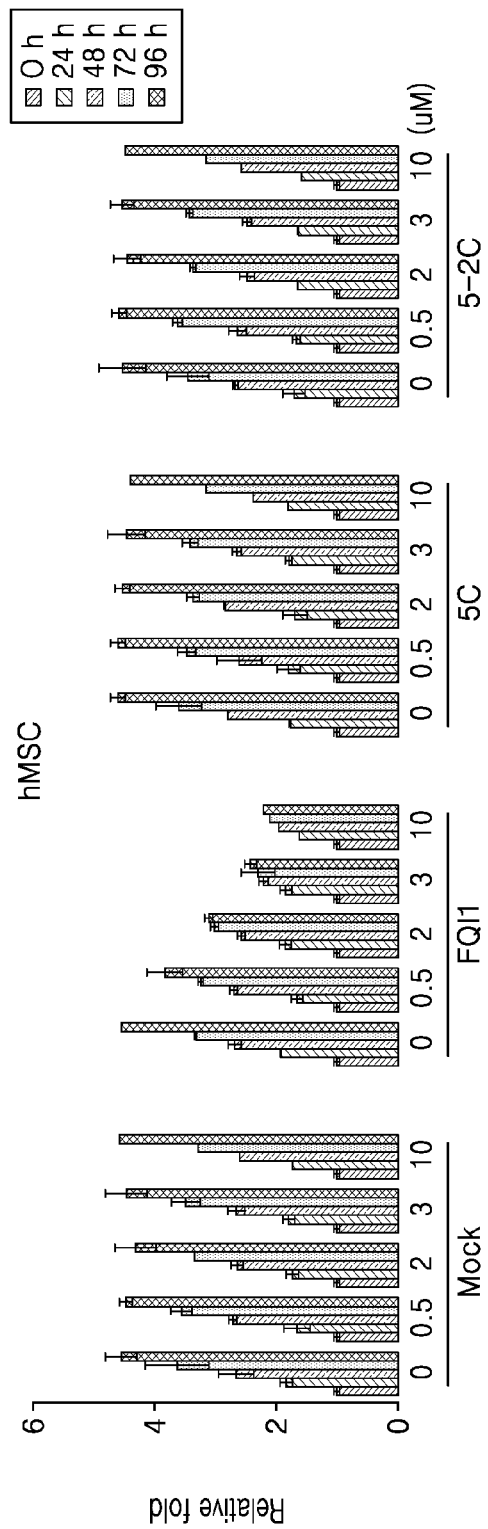

[Fig. 5i]
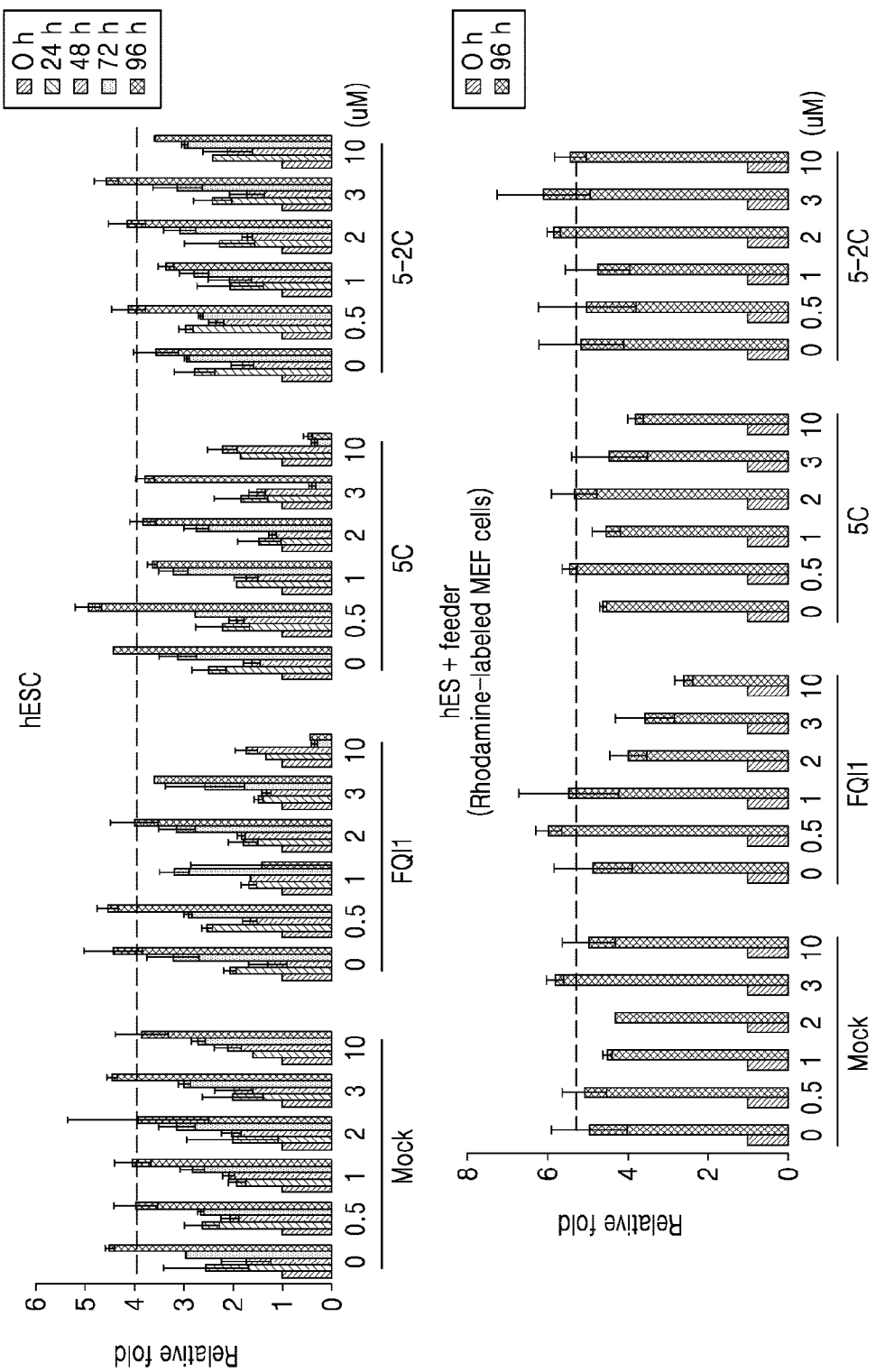

[Fig. 5j]
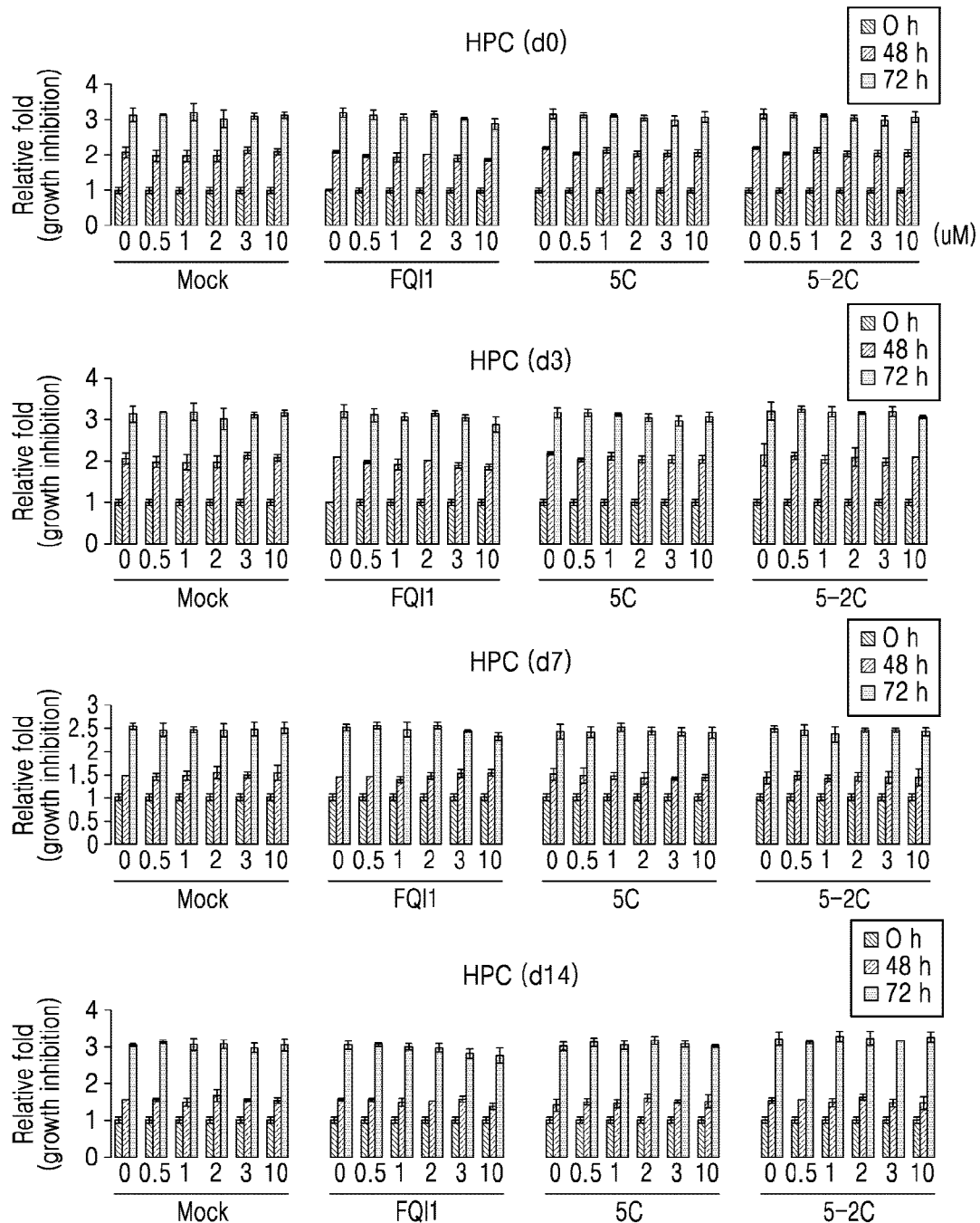

[Fig. 5k]
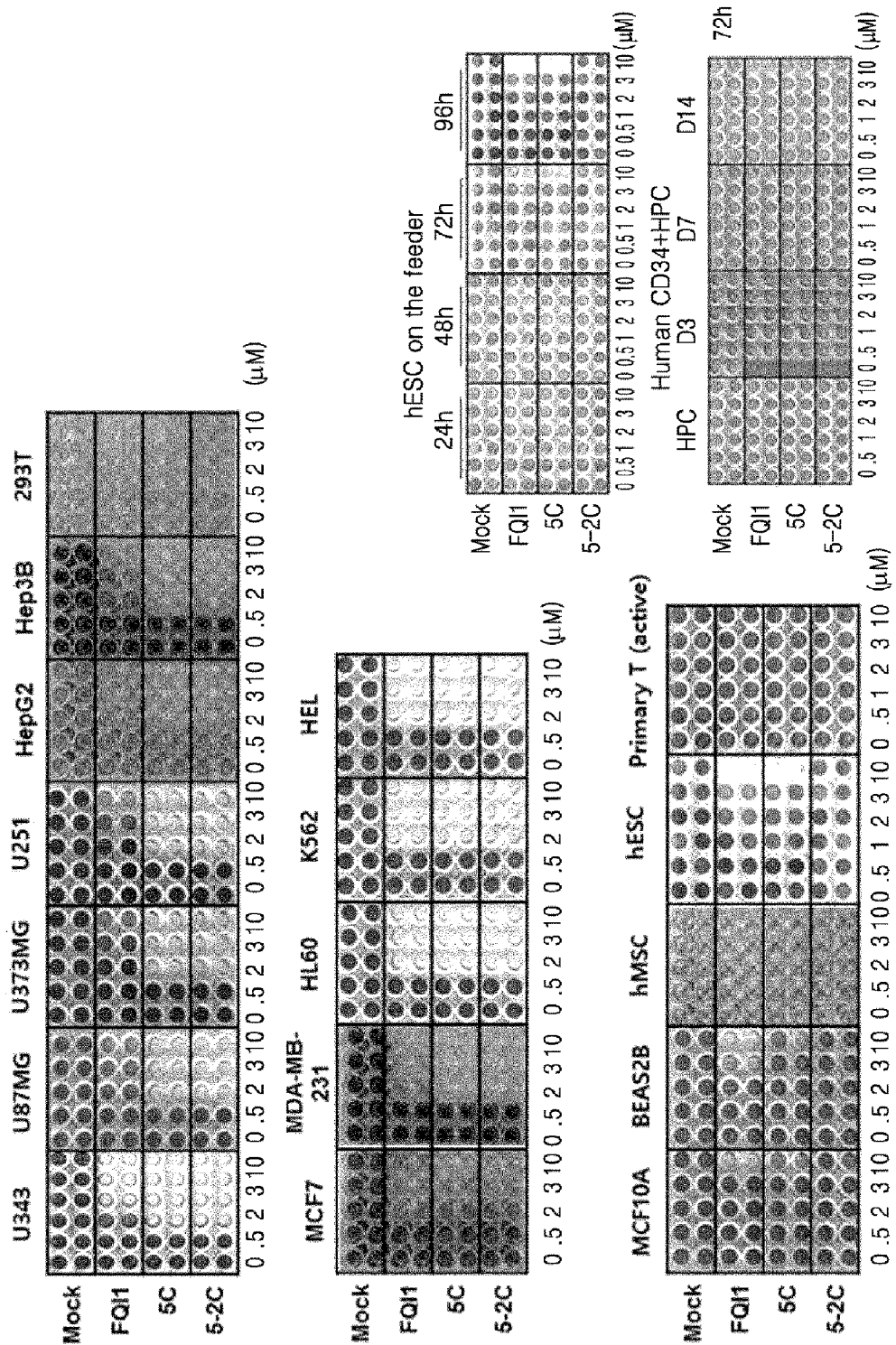

[Fig. 6a]
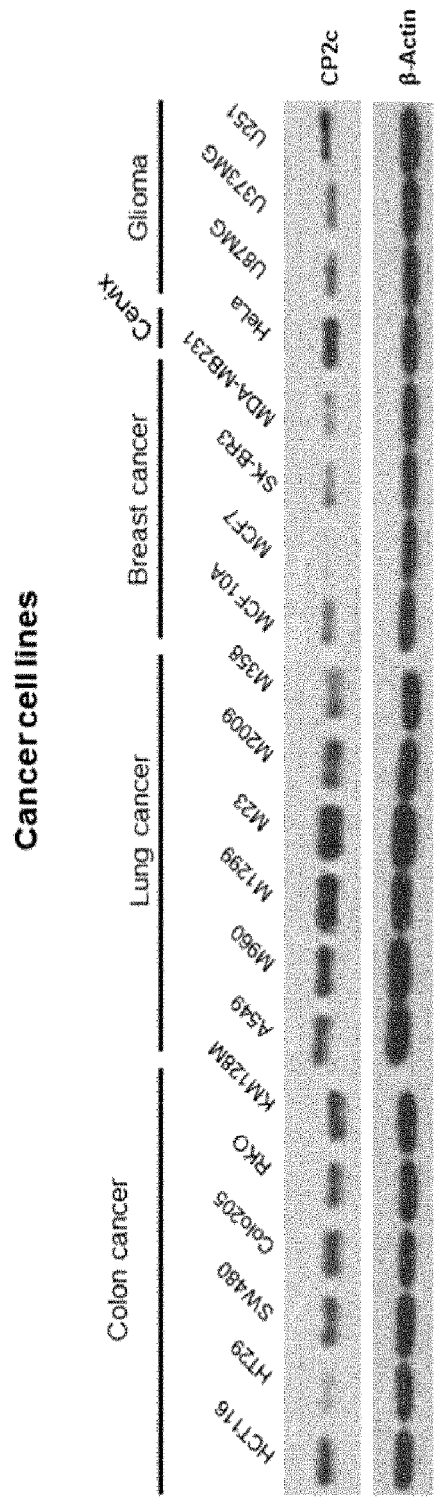

[Fig. 6b]
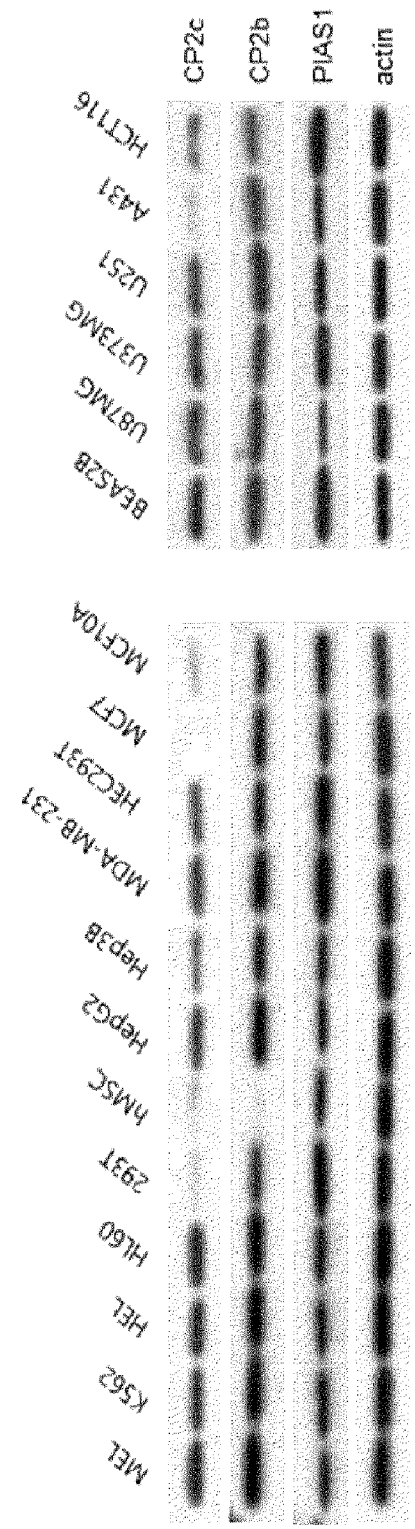

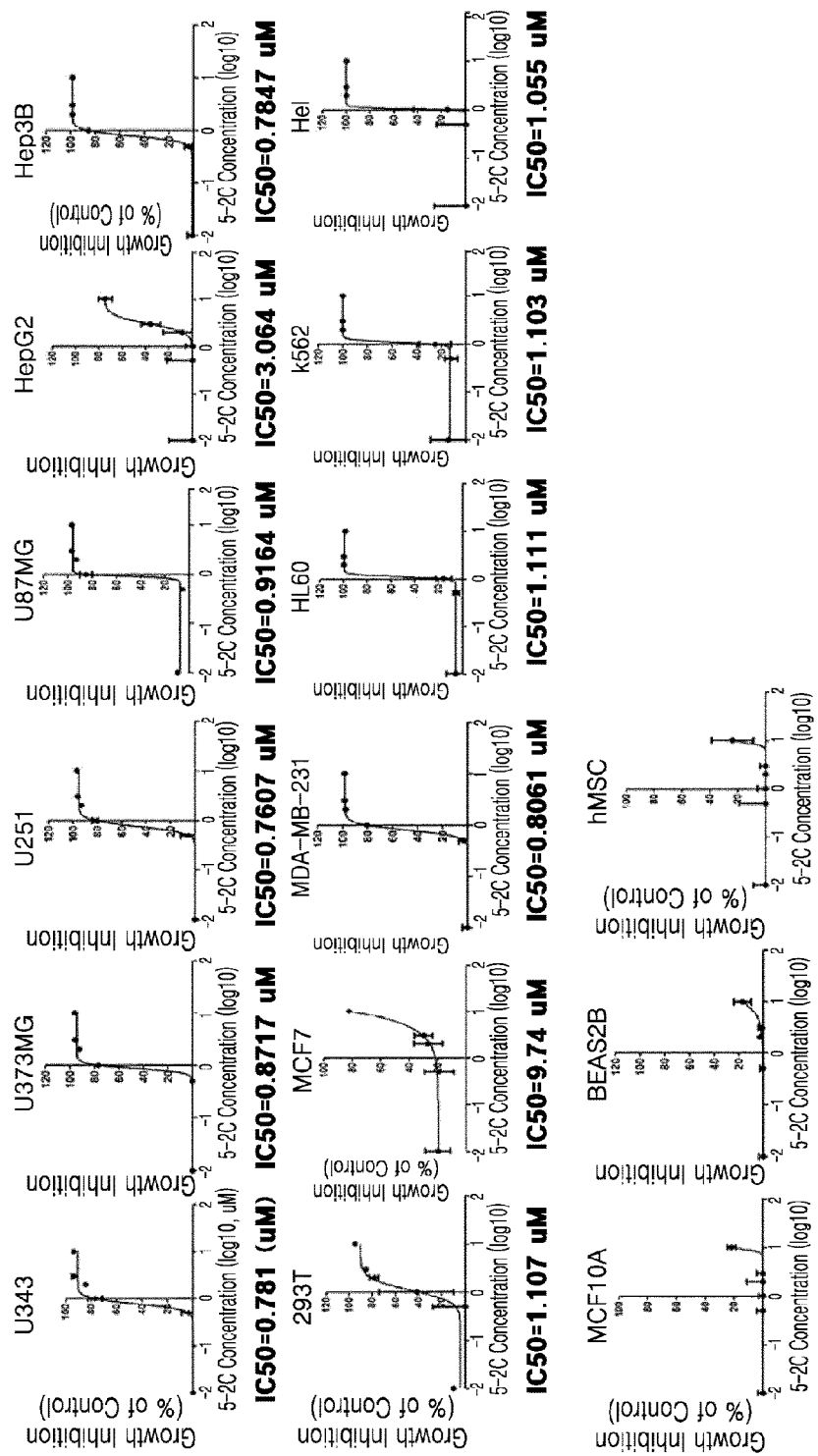
[Fig. 7a]

[Fig. 7b]
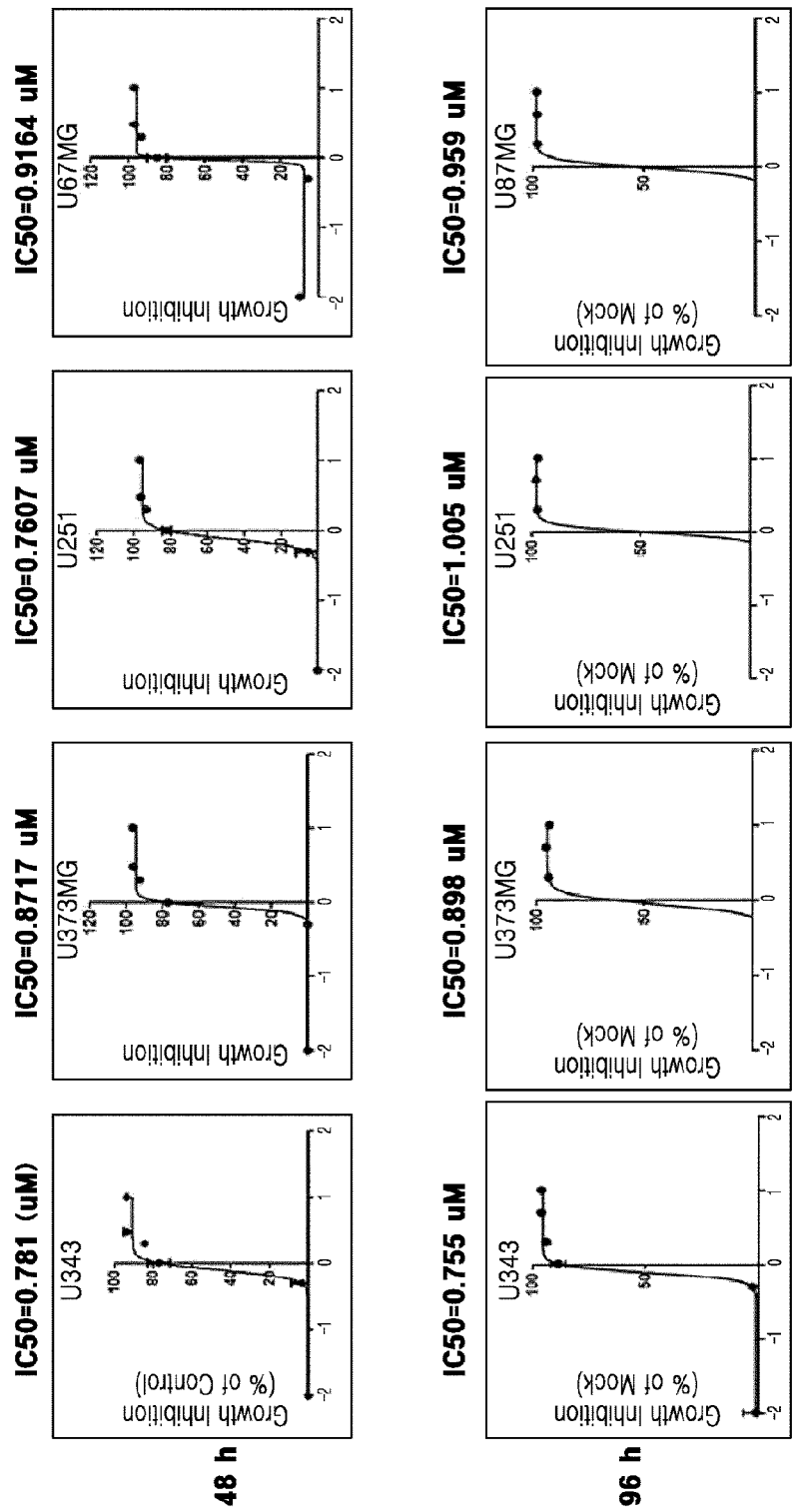

[Fig. 8]
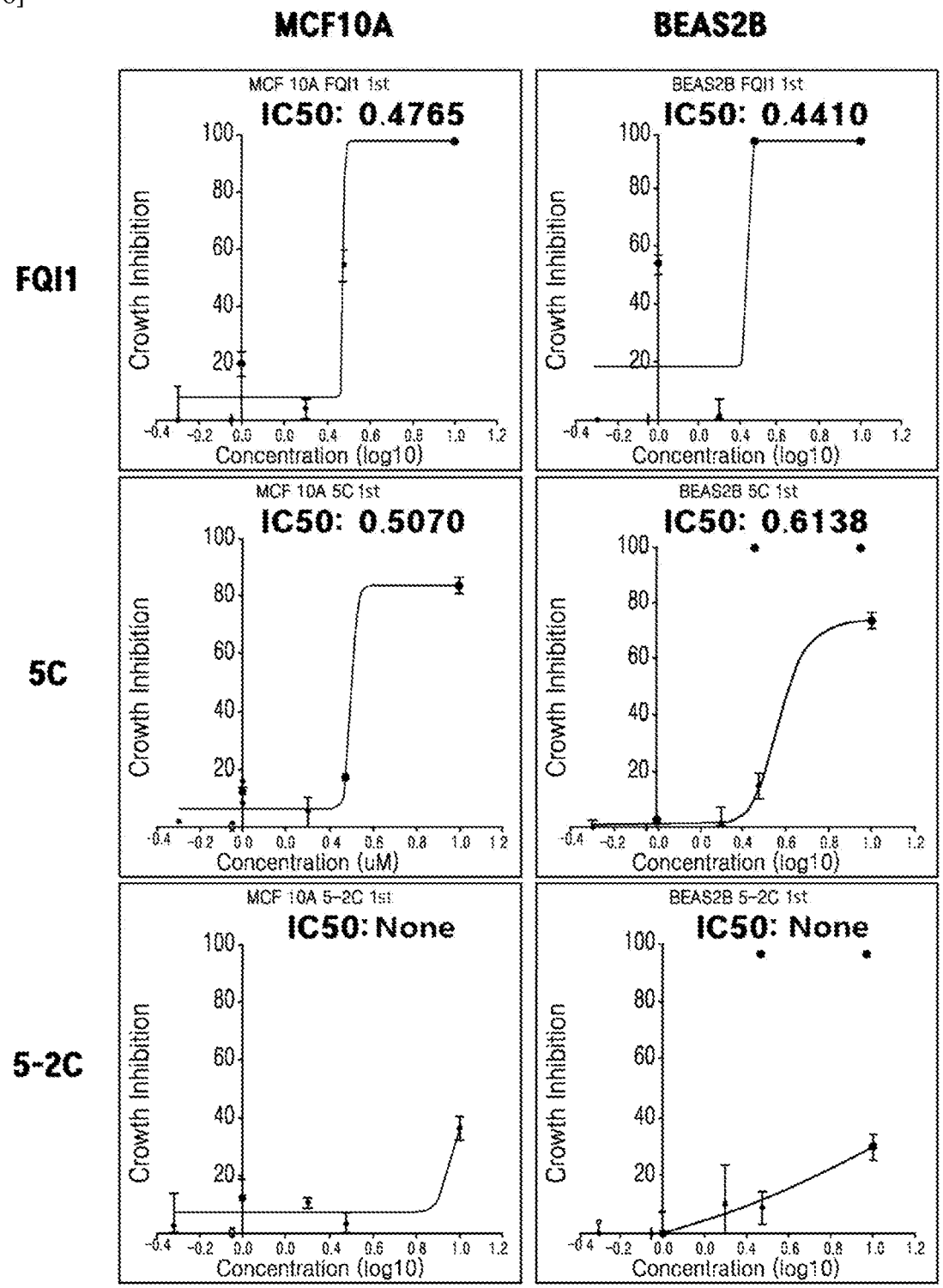

[Fig. 9a]
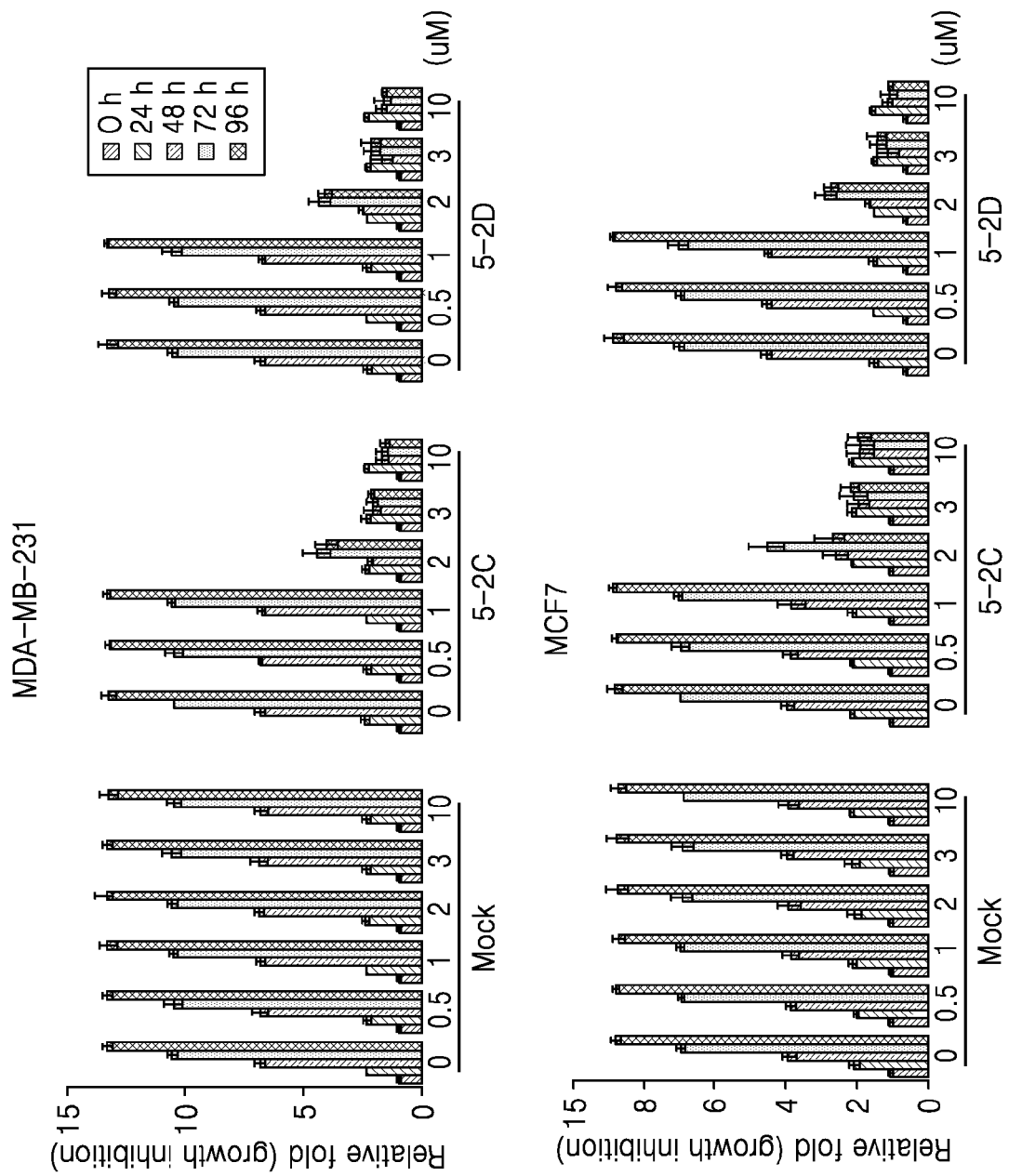

[Fig. 9b]
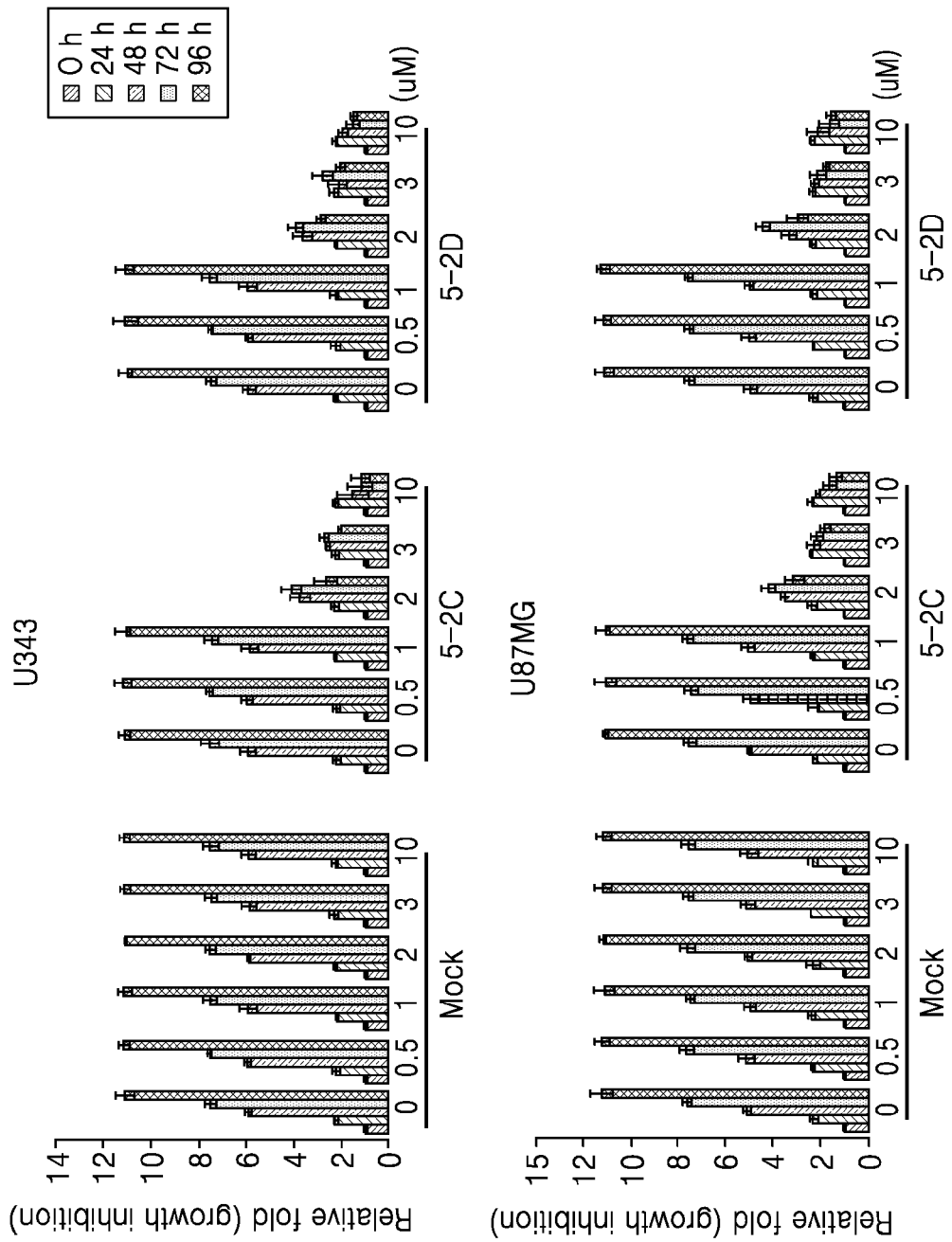

[Fig. 9c]
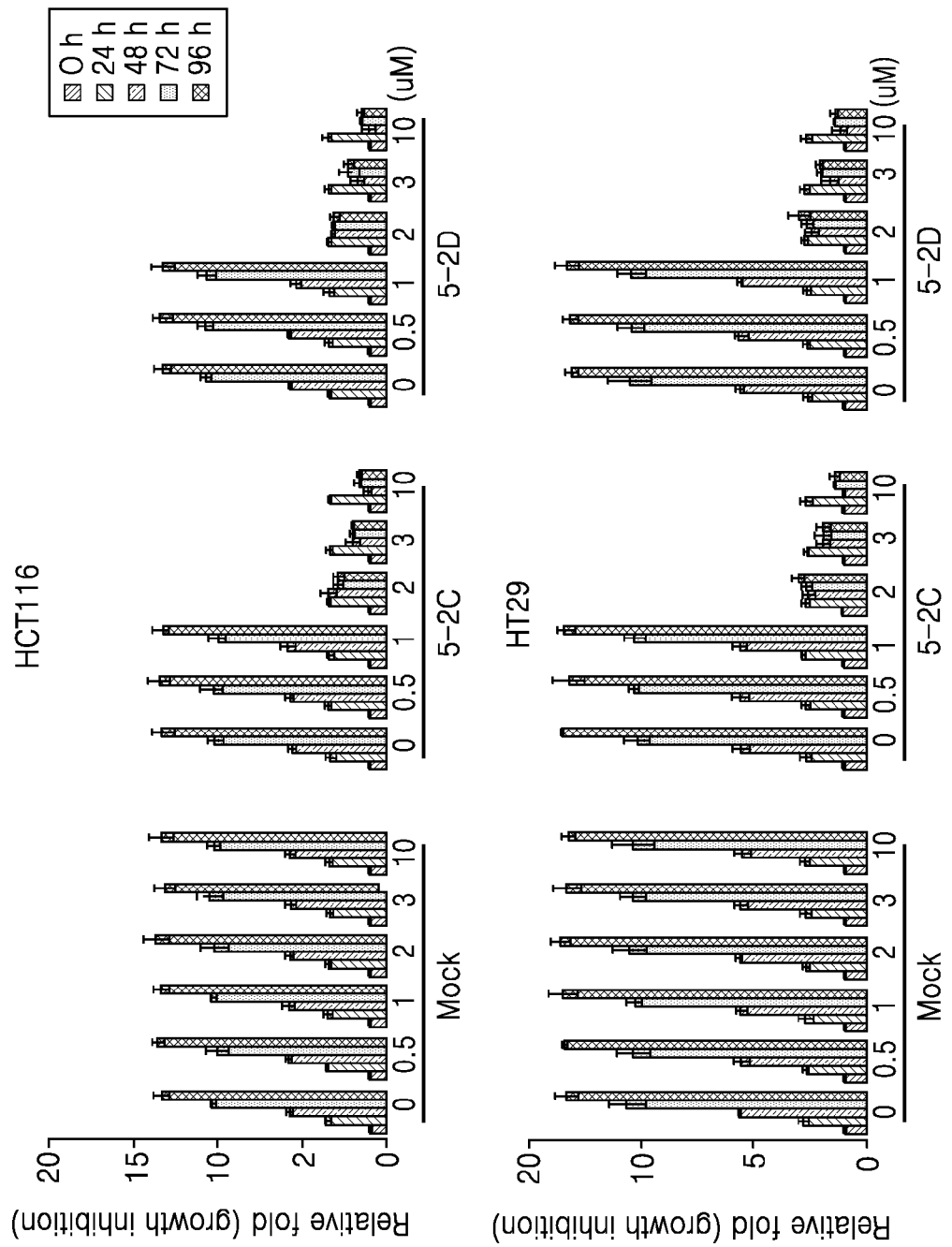

[Fig. 9d]
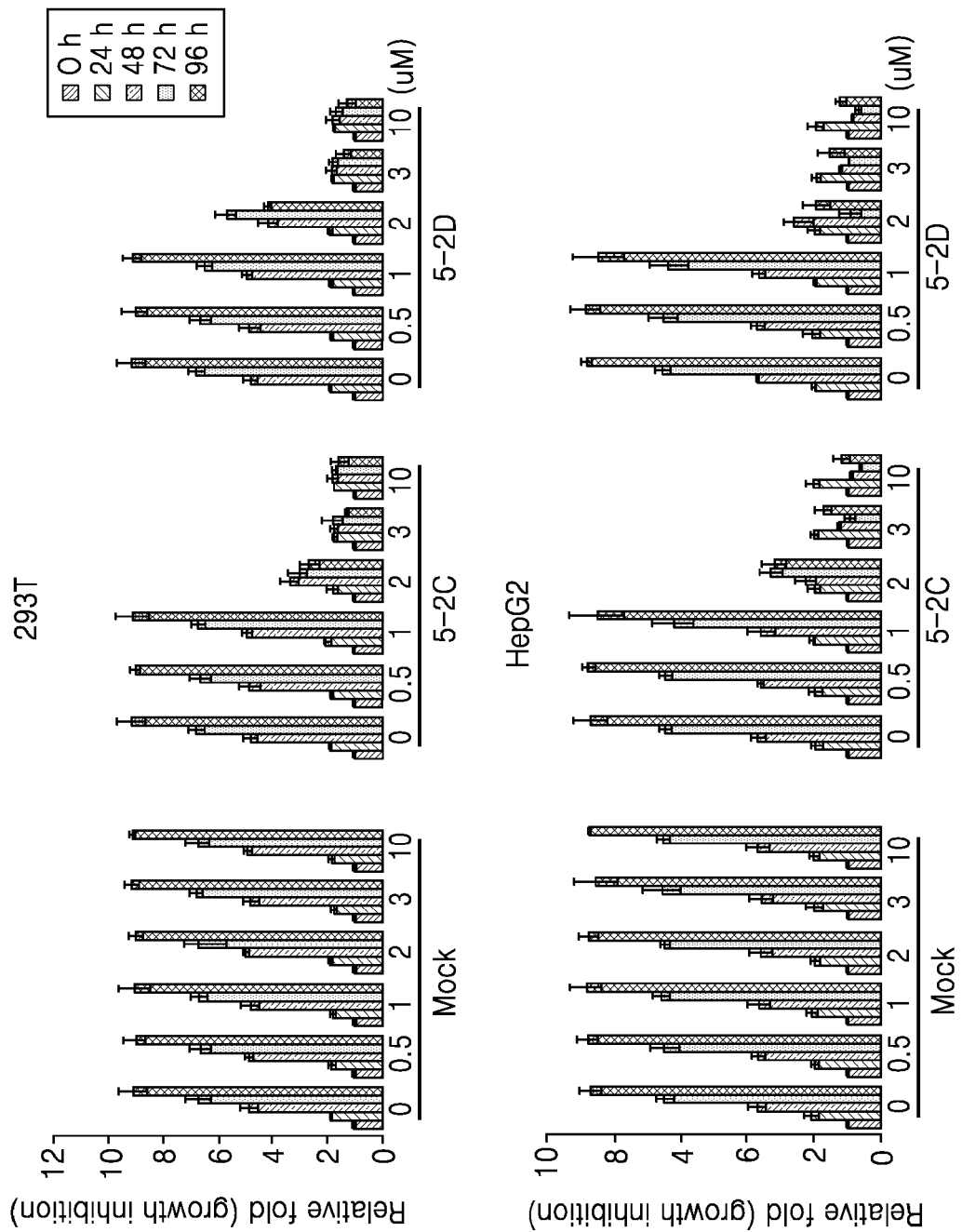

[Fig. 9e]
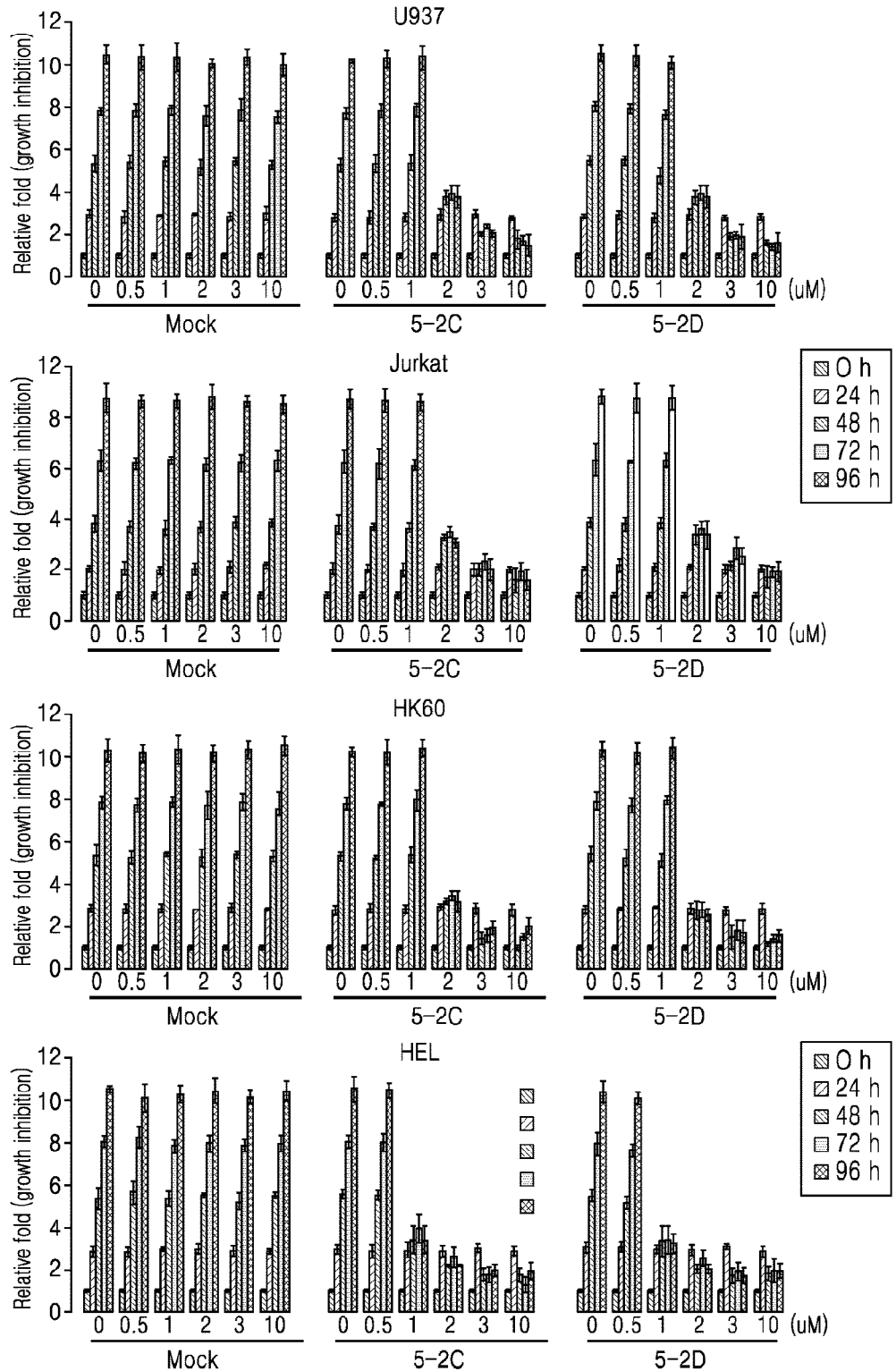

[Fig. 9f]
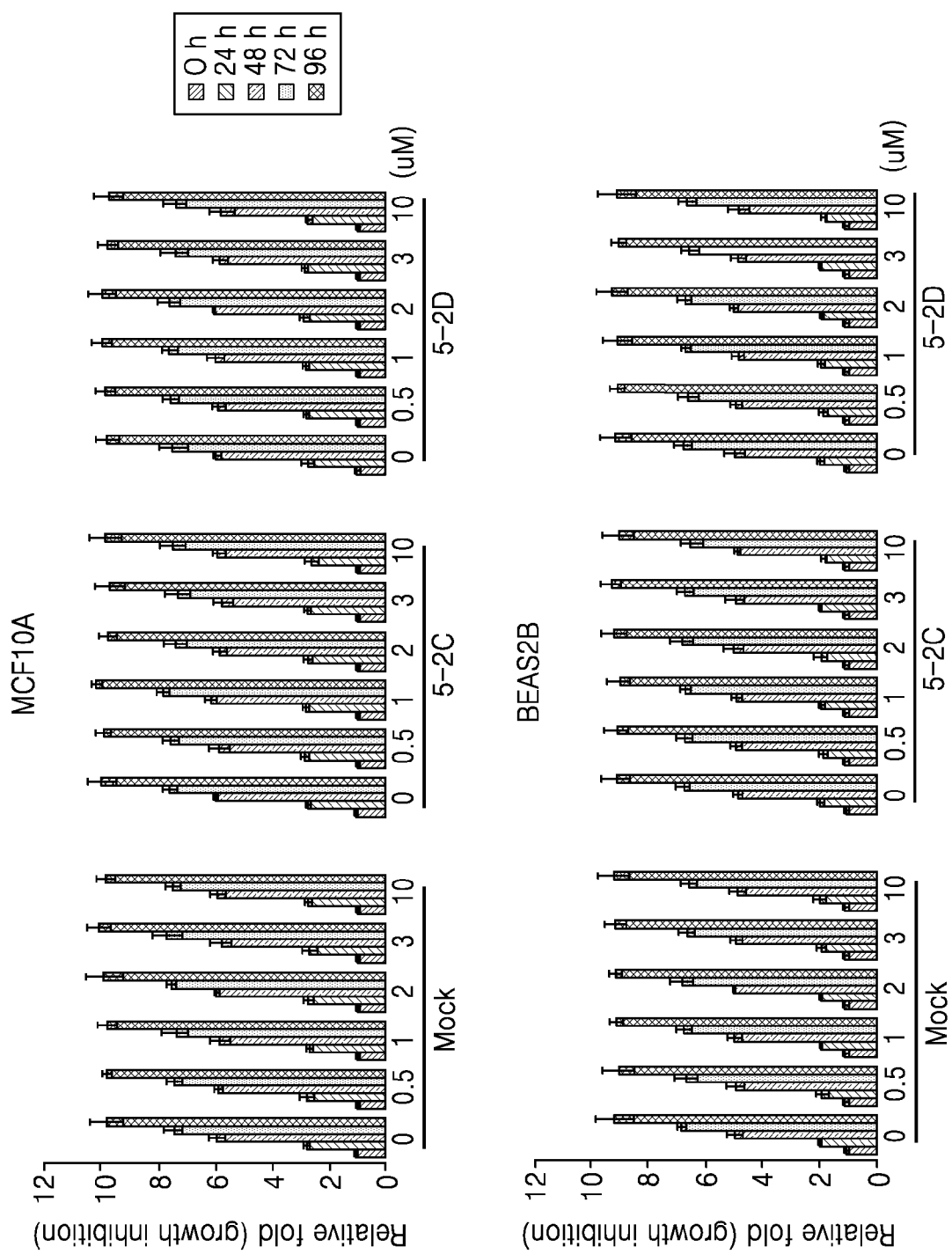

[Fig. 9g]
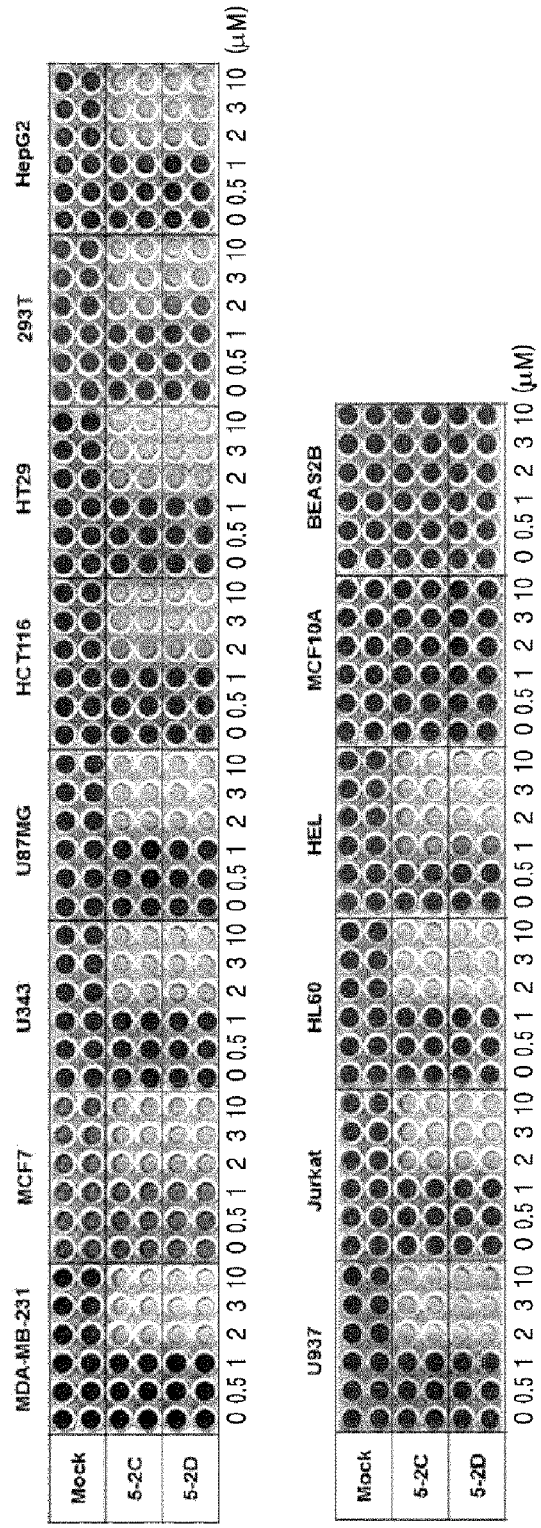

[Fig. 10]
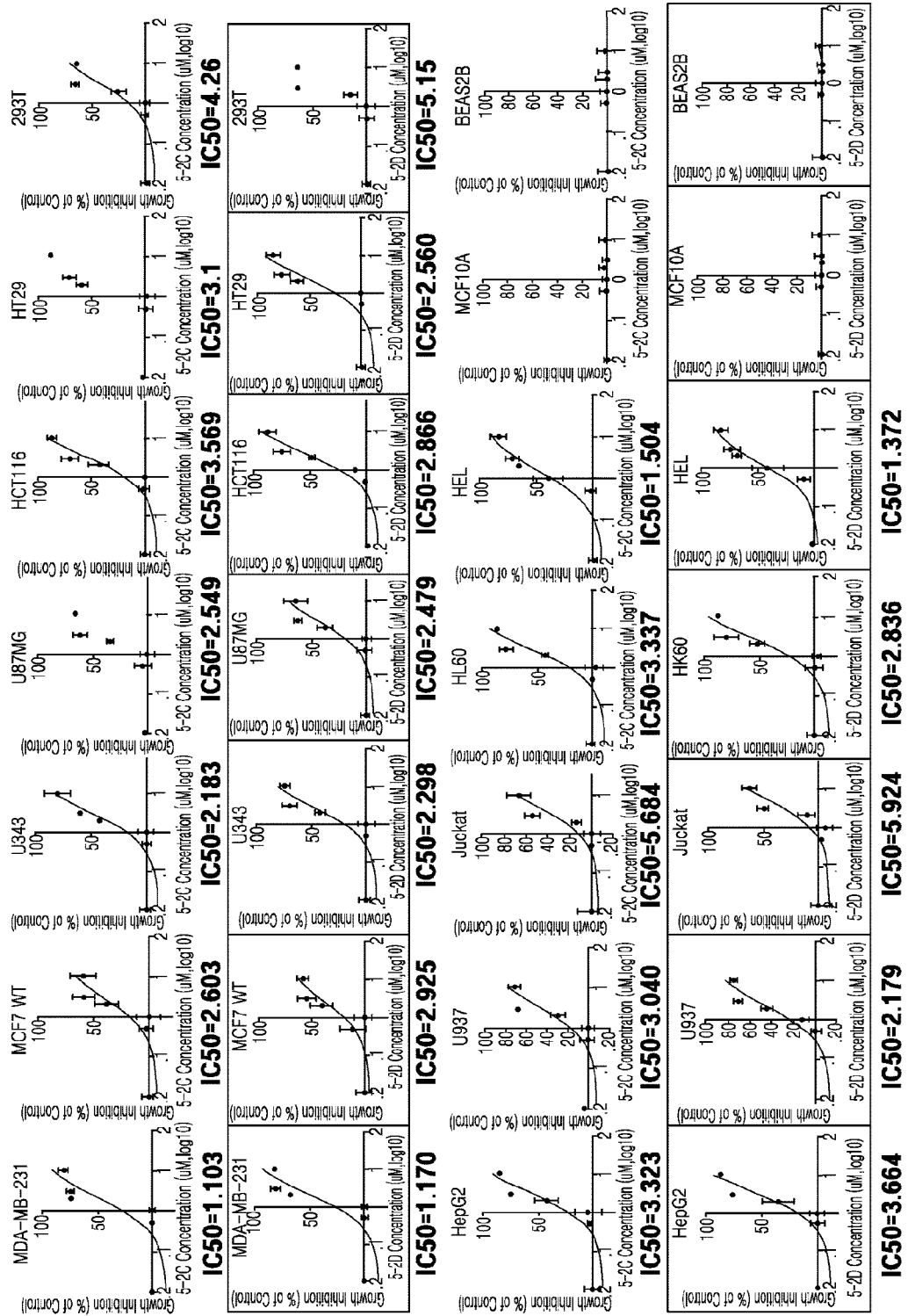

[Fig. 11a]
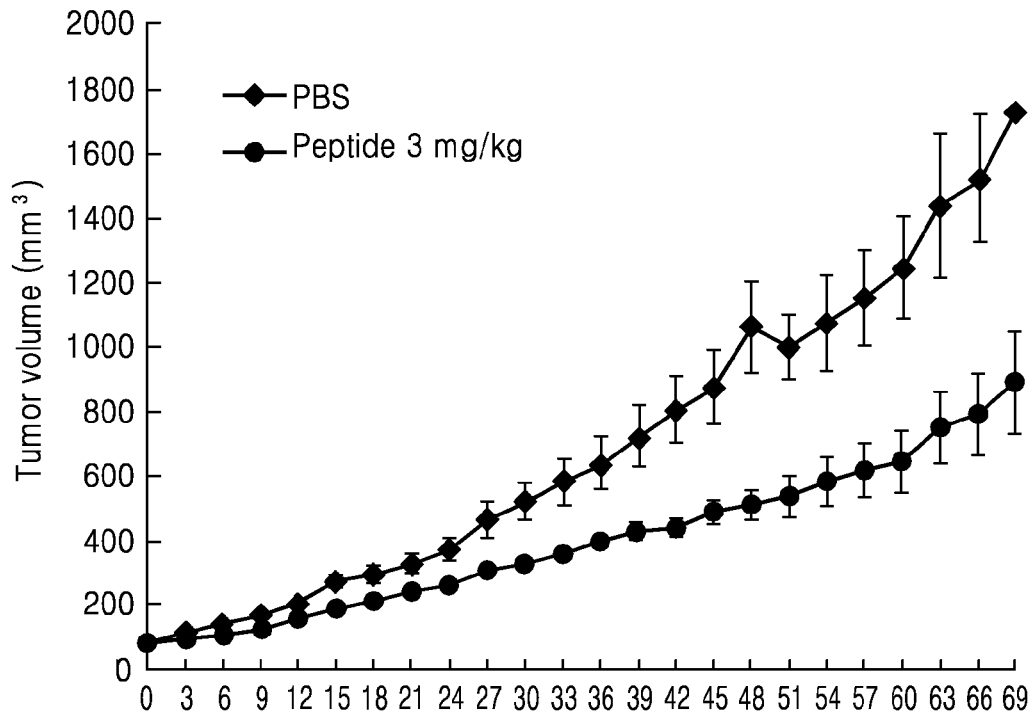
[Fig. 11b]
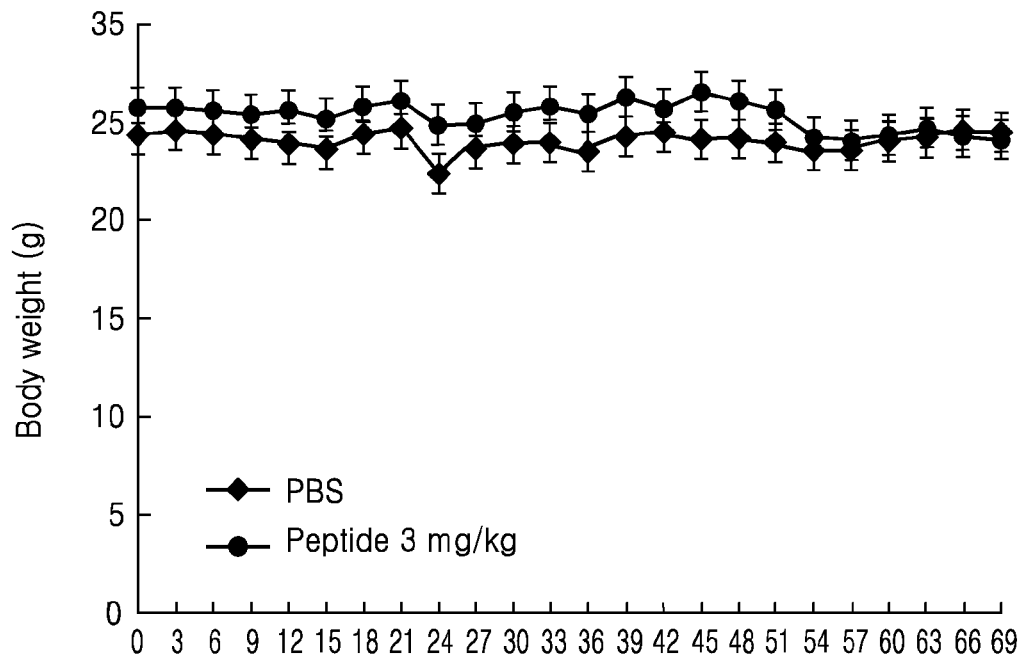

[Fig. 11c]
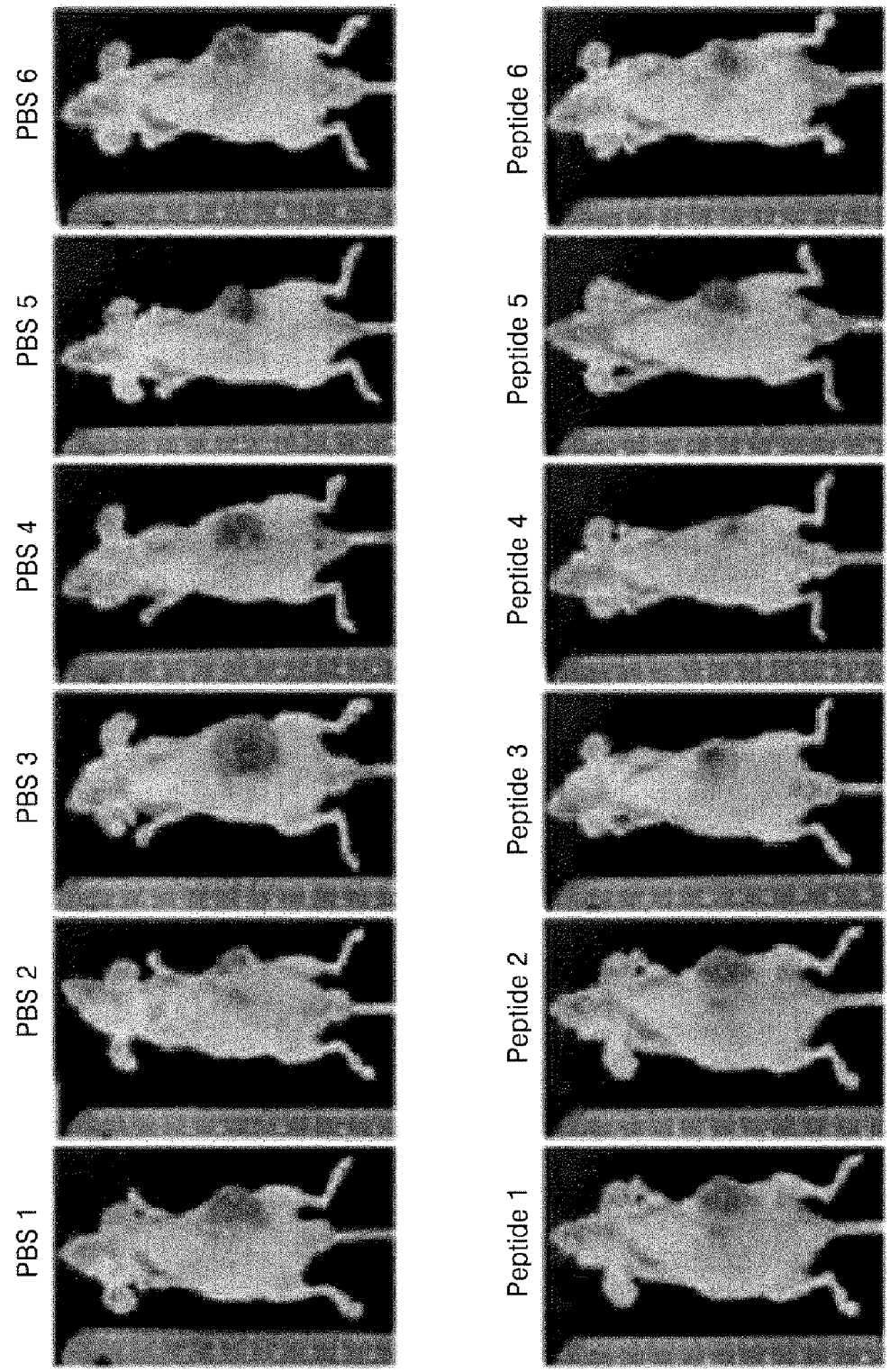

[Fig. 11d]
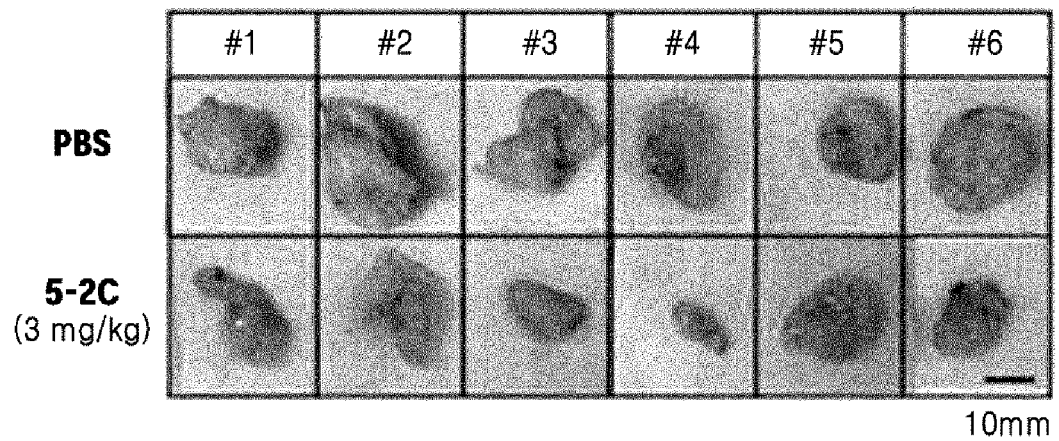
[Fig. 11e]
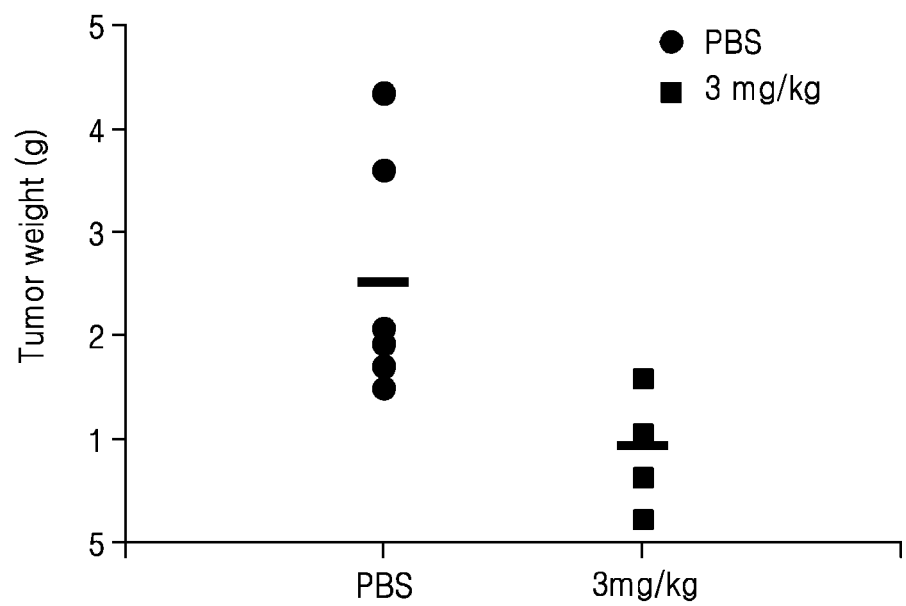

[Fig. 11f]
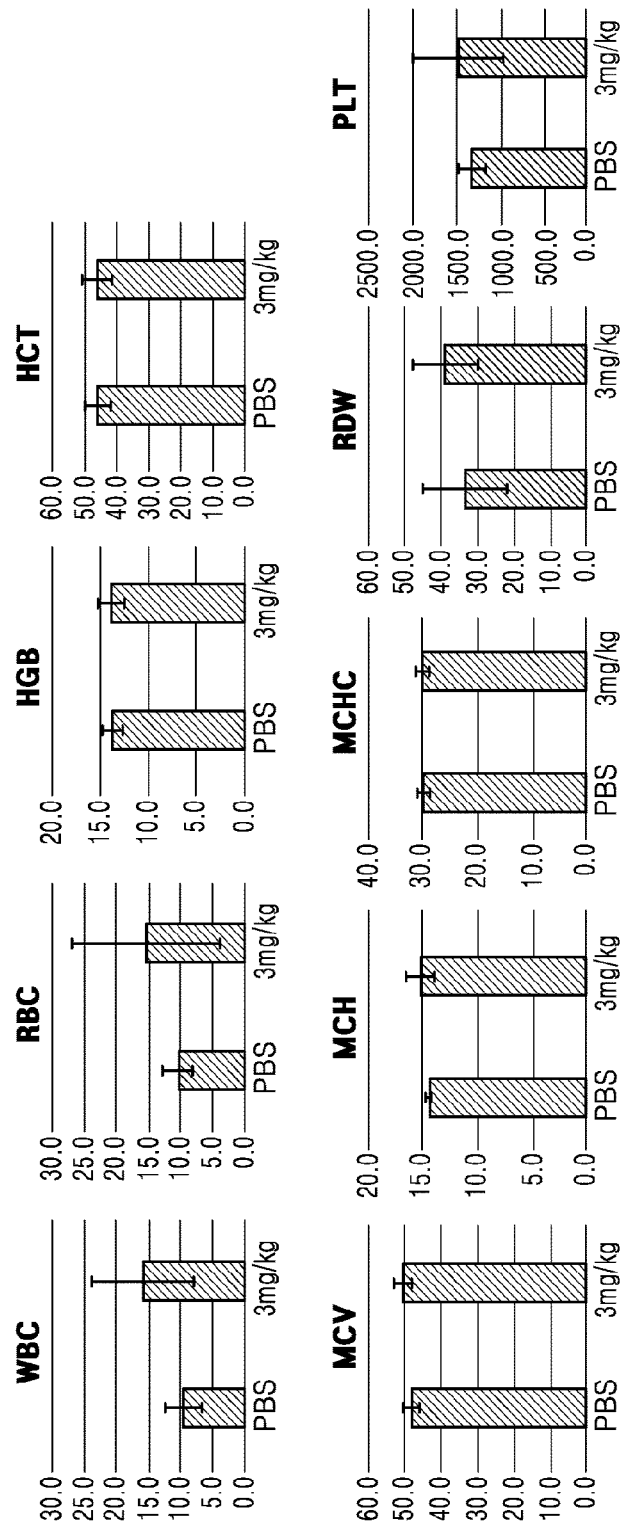

[Fig. 11g]
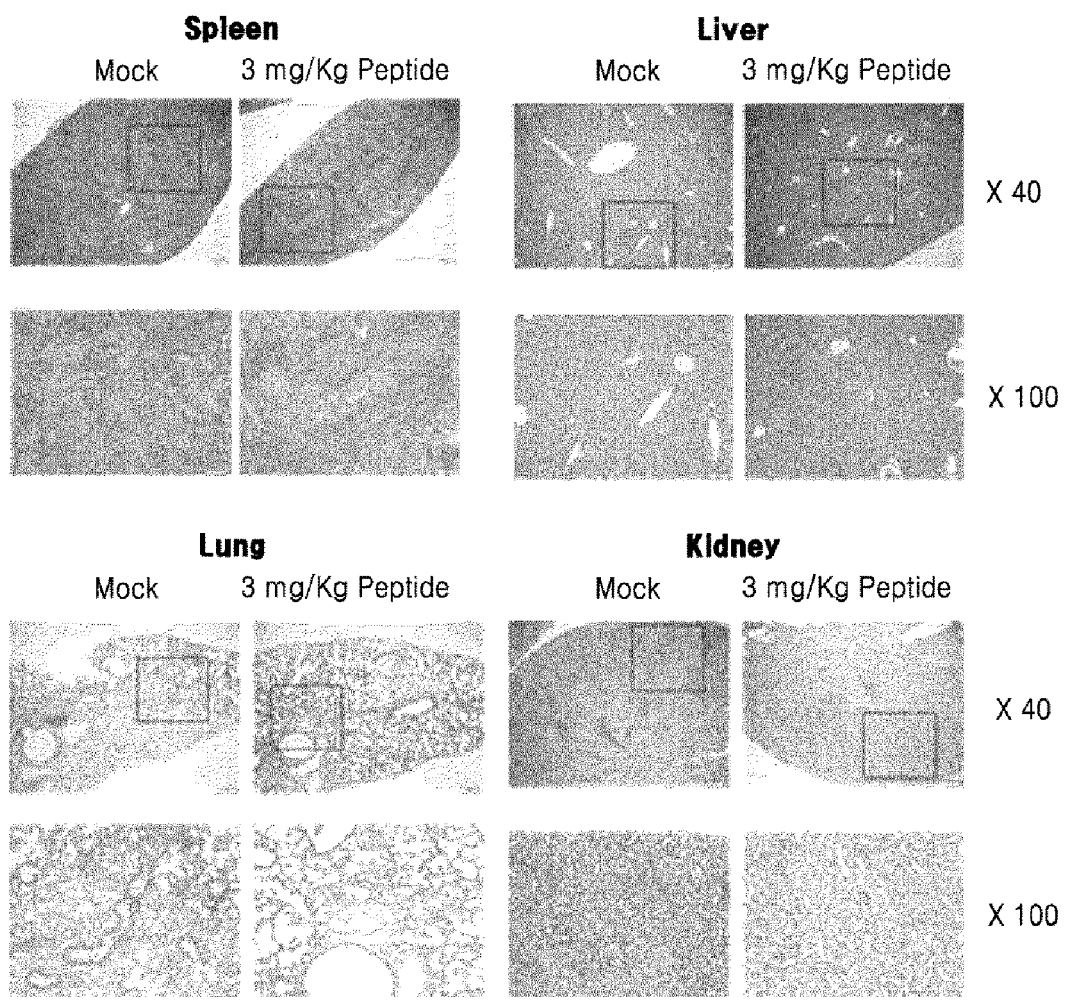

[Fig. 12a]
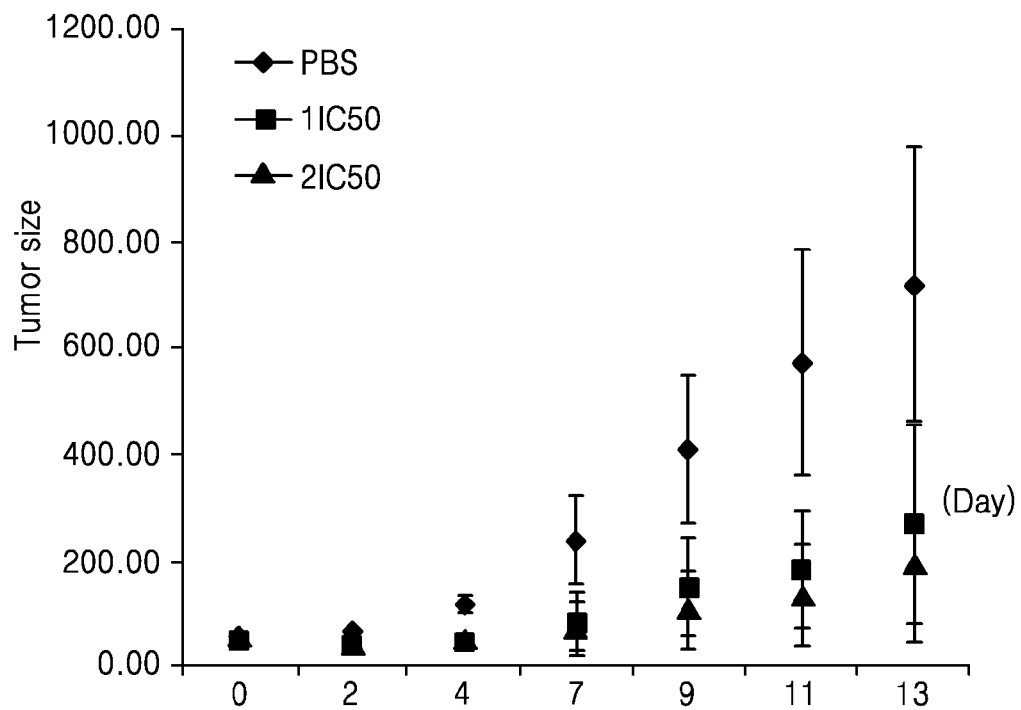
[Fig. 12b]
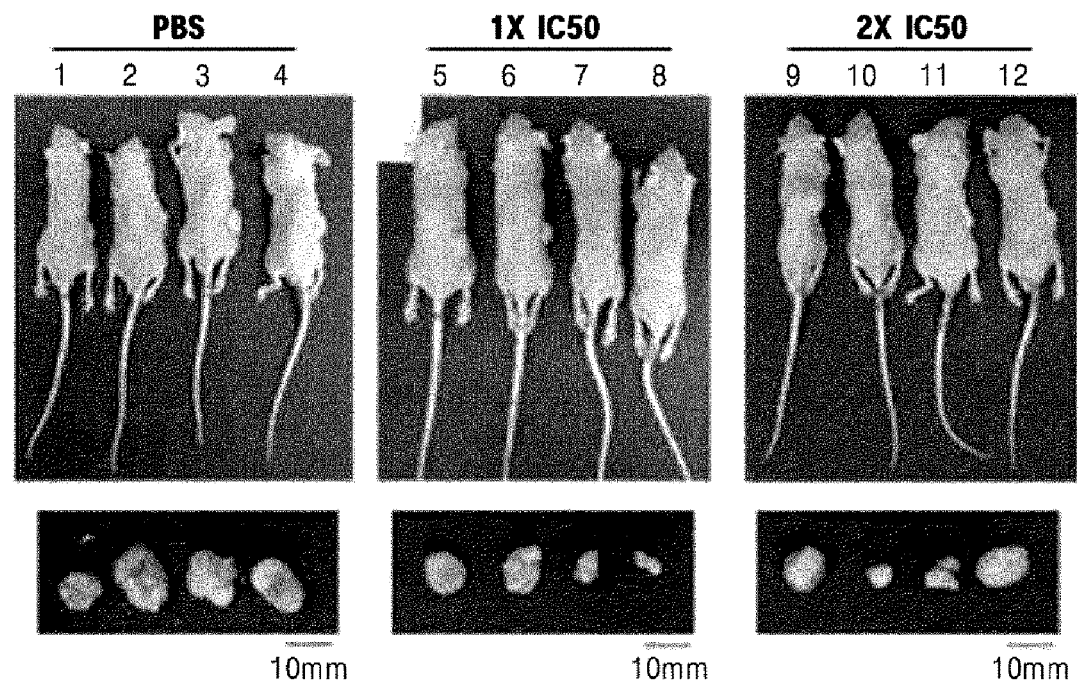

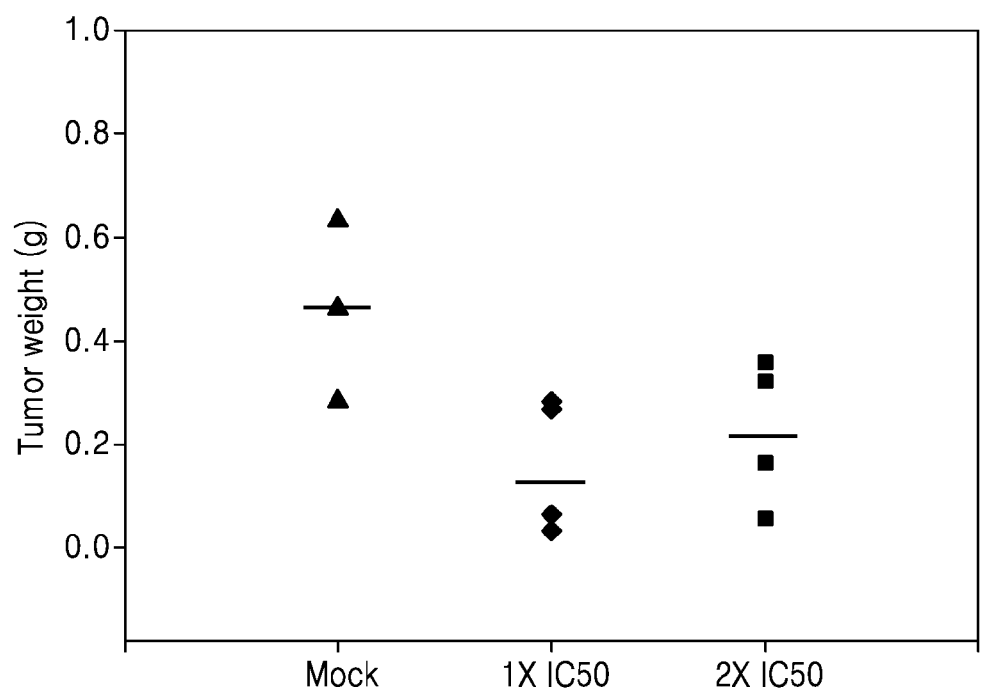
[Fig. 12c]

[Fig. 12d]
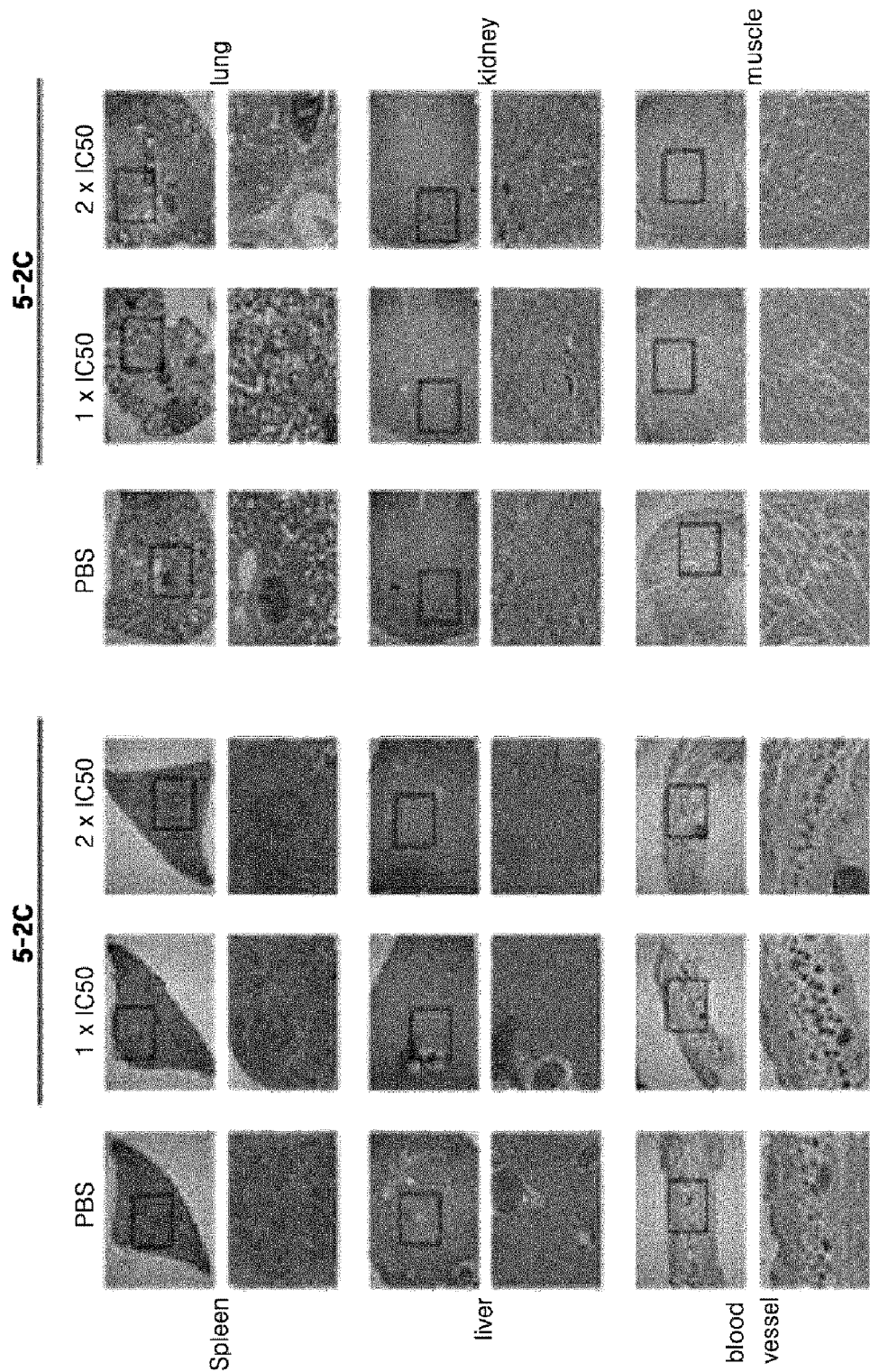

[Fig. 13a]
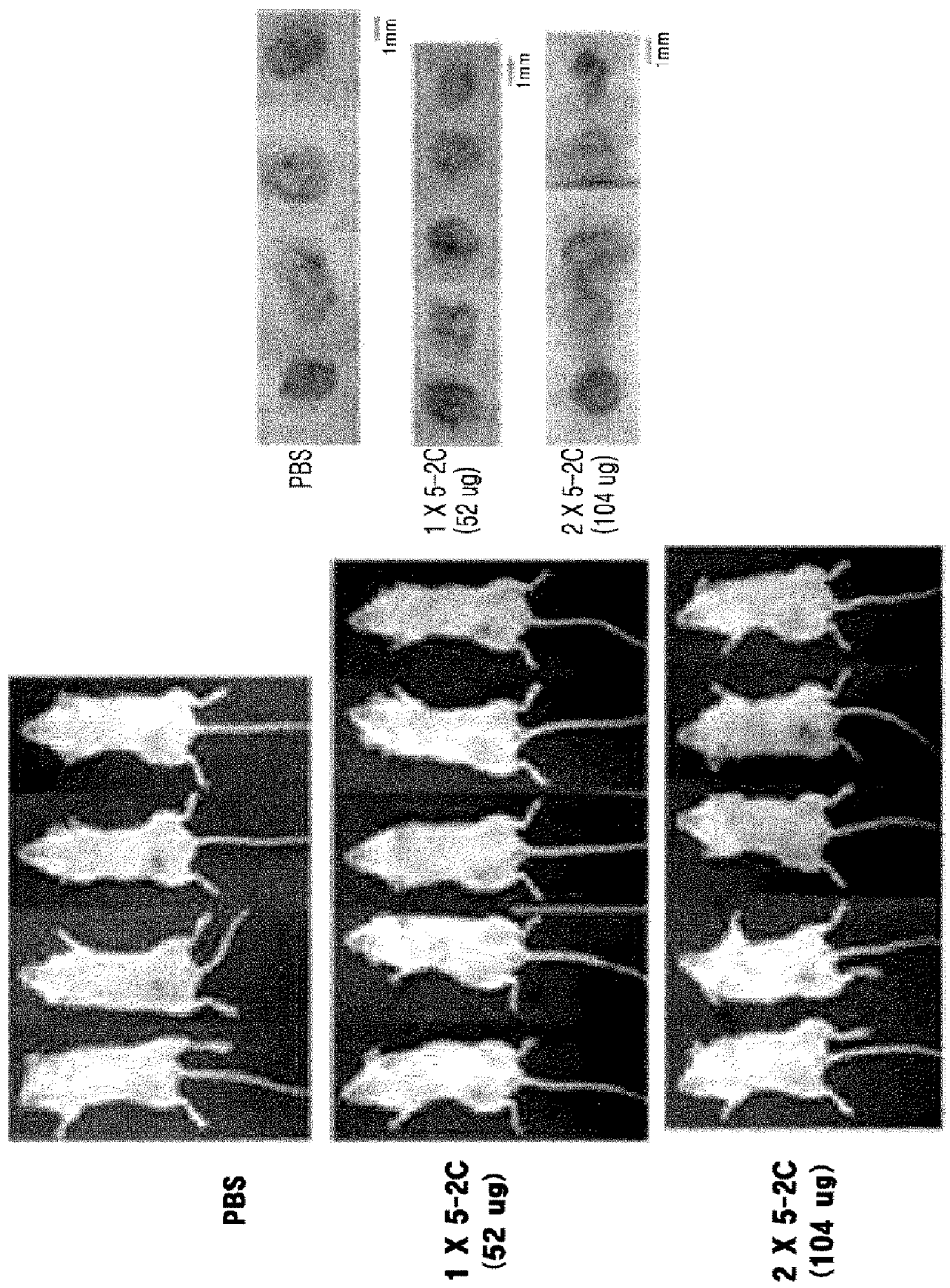

[Fig. 13b]
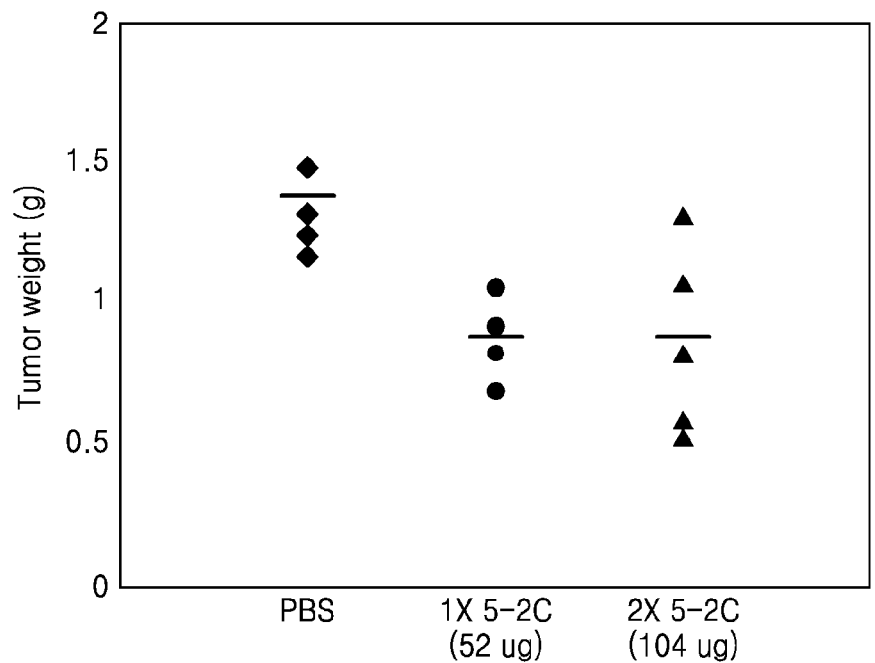
[Fig. 13c]
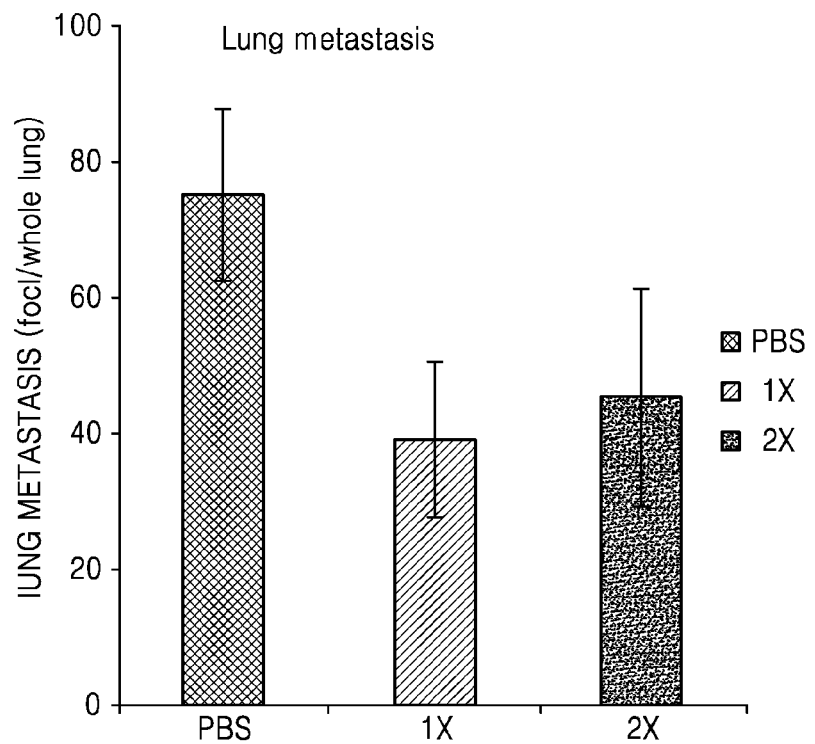

[Fig. 13d]
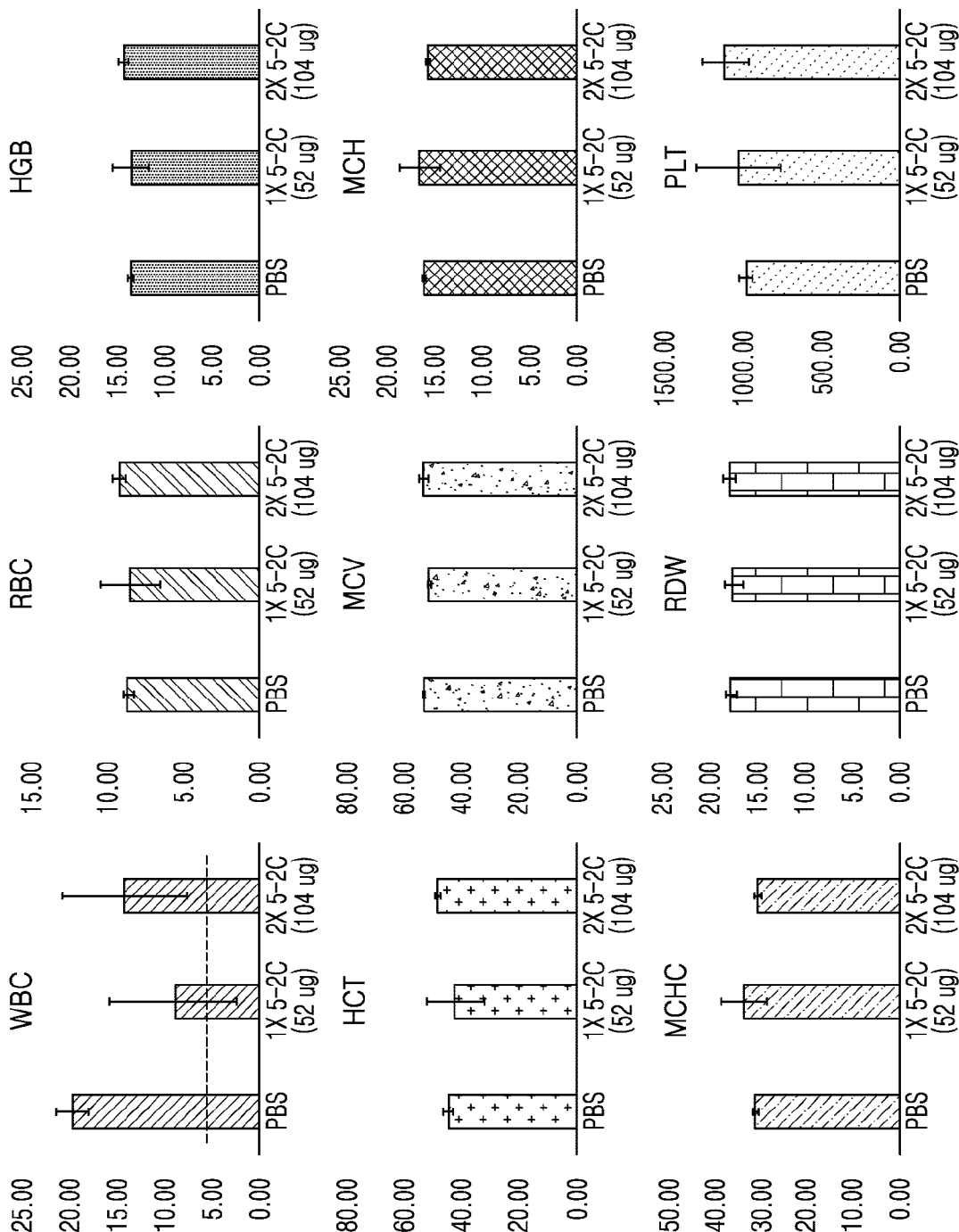

[Fig. 14a]
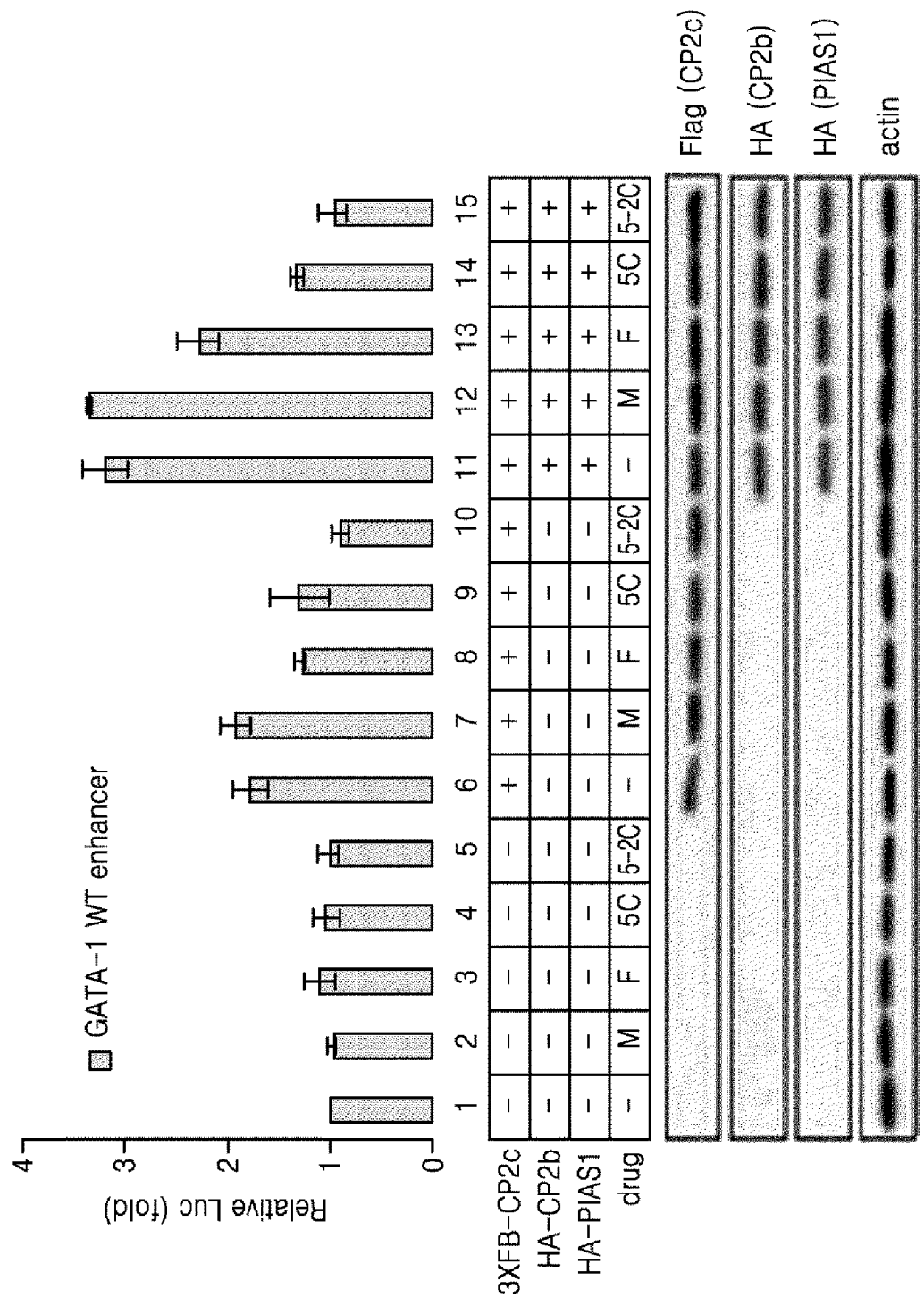

[Fig. 14b]
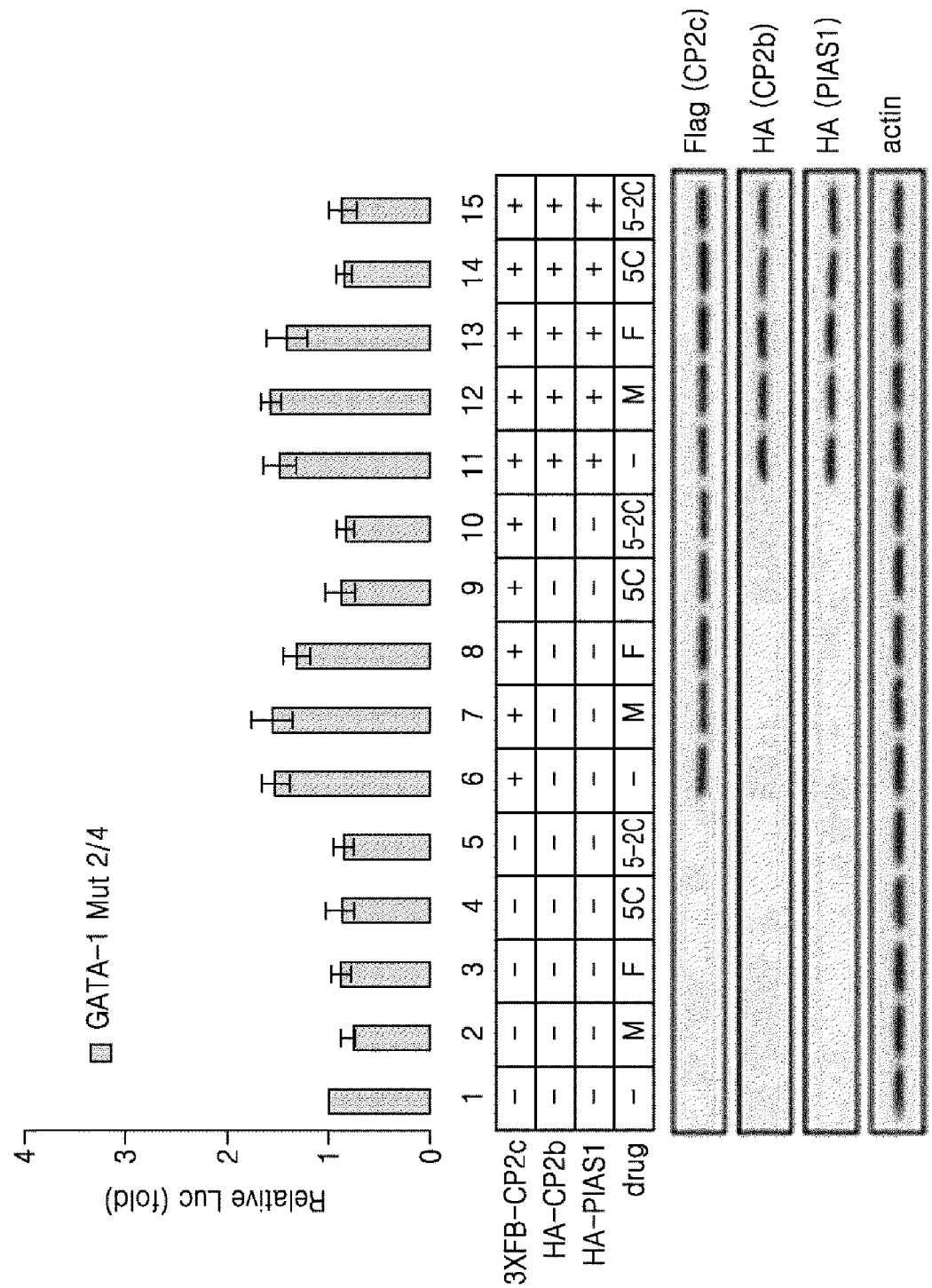

[Fig. 14c]
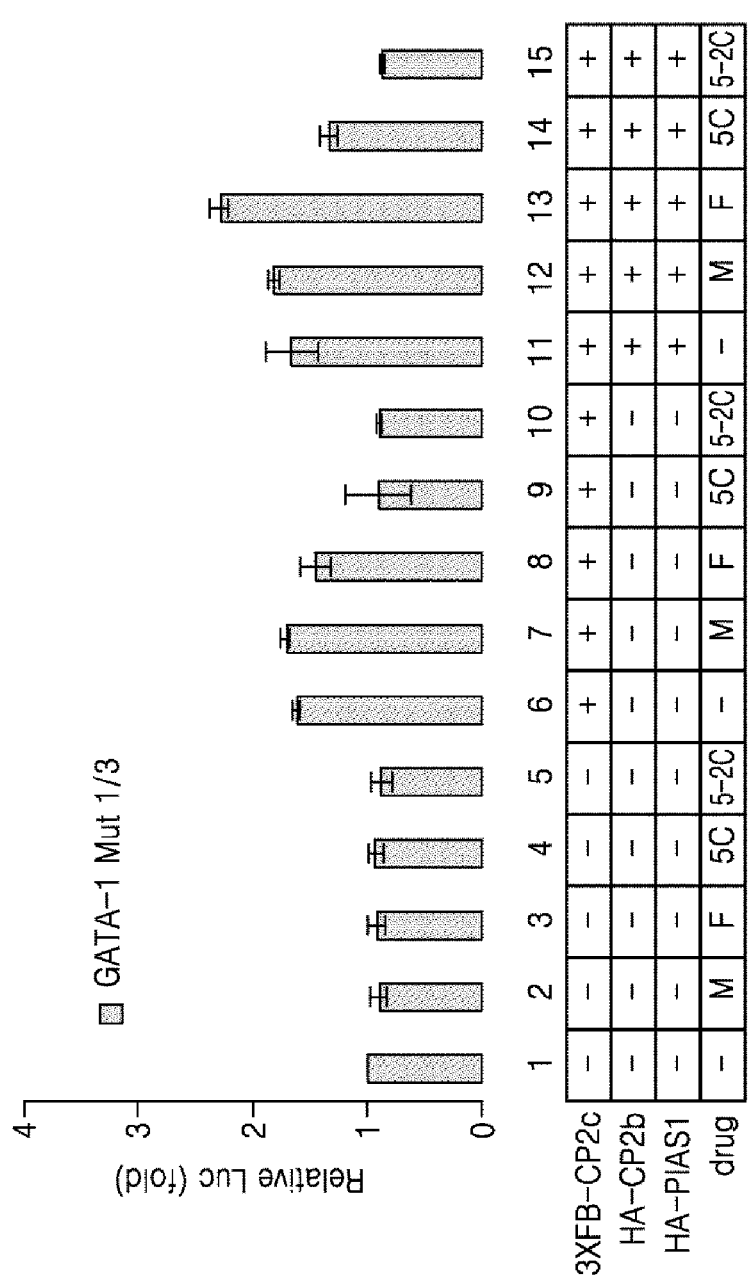

[Fig. 14d]
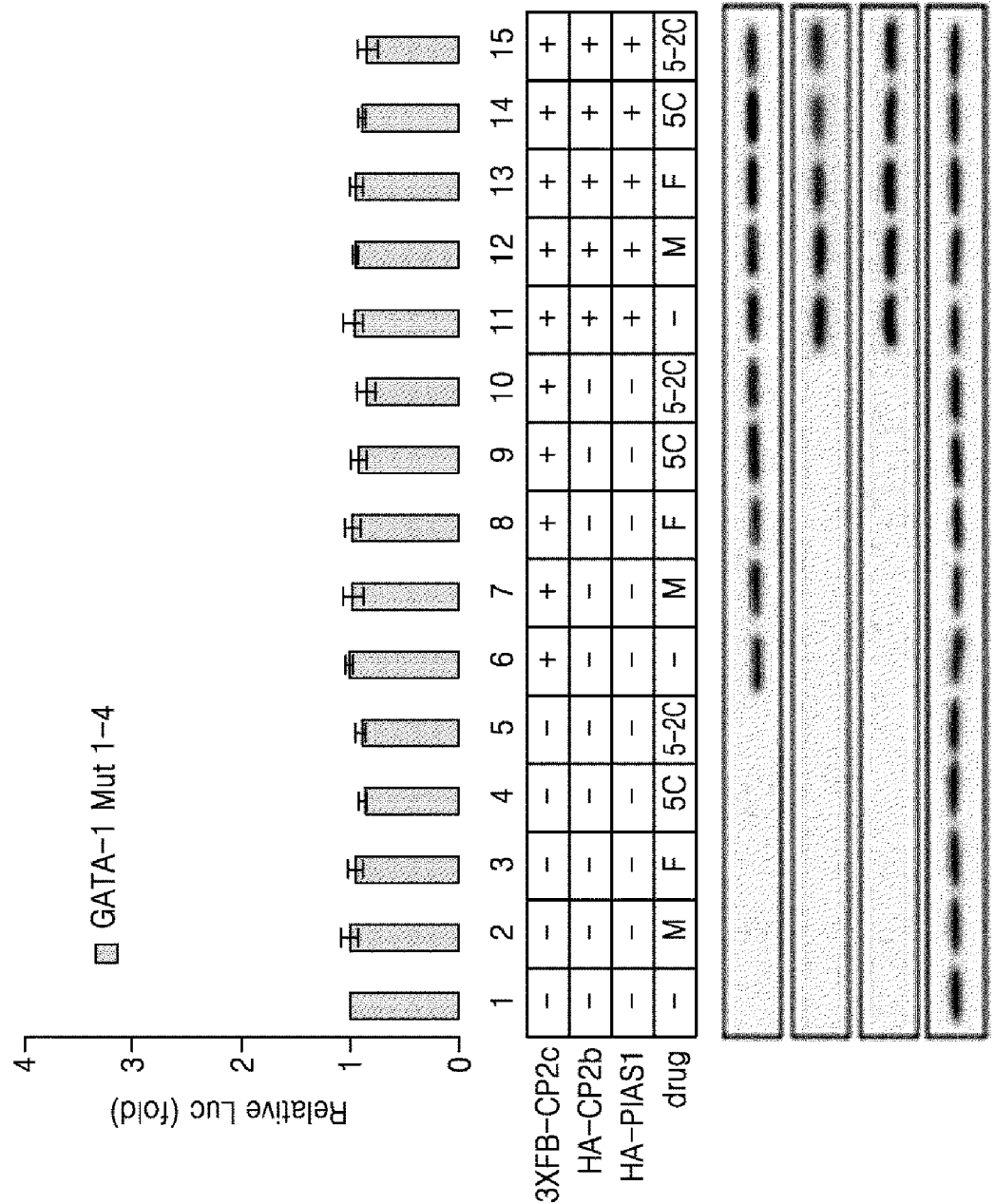

[Fig. 14e]

|  | GATA-1 | GATA-1 | | CP2 | | | | |
|---|---|---|---|---|---|---|---|---|
|  |  |  | 1 | 2 | 3 | 4 | | |
| GATA-1 WT enhancer | CGAGTCCATCT | GATAAGACTTATC | TGCTGCC CCAG | AGCAGGCCAG | AGCAGGCCAG | AGCTGG | CGTAAGCCCAG | -655 |
| Mut 1 / 3 | CGAGTCCATCT | GATAAGACTTATC | TGCTGCC <u>ACAG</u> | AGCAGGTAAG | AGCAGGCCAG | AGCTGG | CGTAAGCCCAG | |
| Mut 2 / 4 | CGAGTCCATCT | GATAAGACTTATC | TGCTGCC CCAG | AT <u>TGAGCCAG</u> | AT TGAG | | CGTAAGCCCAG | -660 |
| Mut 1 – 4 | CGAGTCCATCT | GATAAGACTTATC | TGCTGCC <u>ACAG</u> | AT <u>TGAGTAAG</u> | AT TGAG | | CGTAAGCCCAG | |

← -718      ← -695

[Fig. 15a]
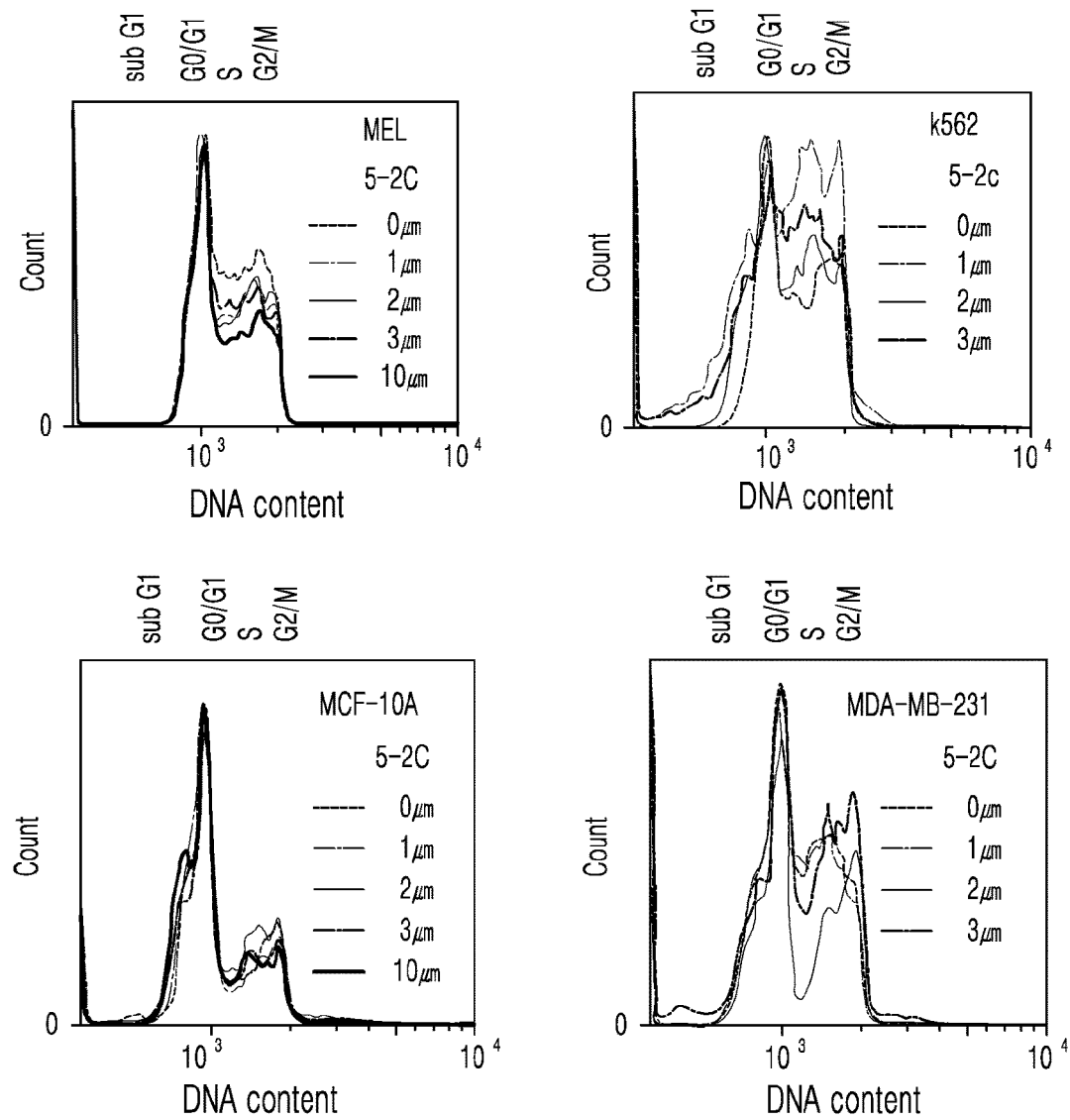

[Fig. 15b]
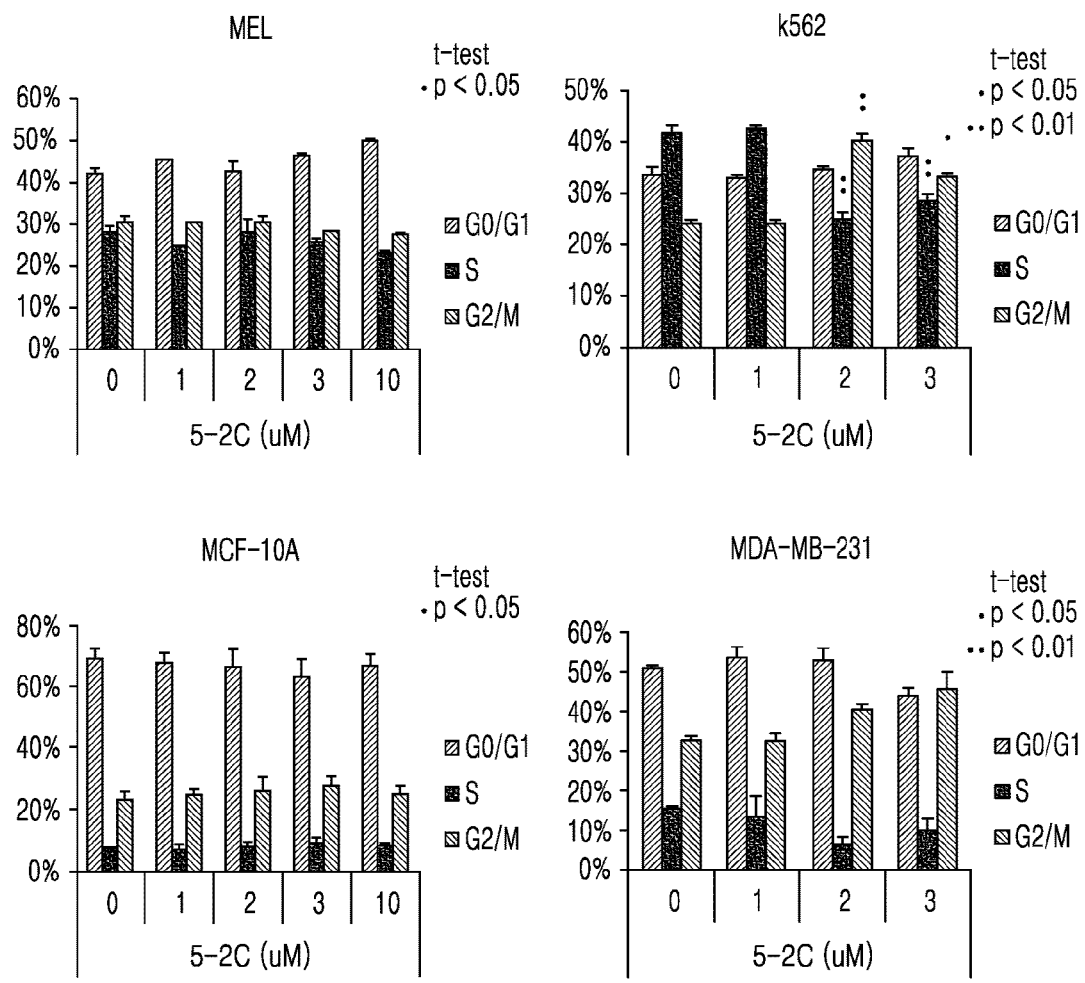

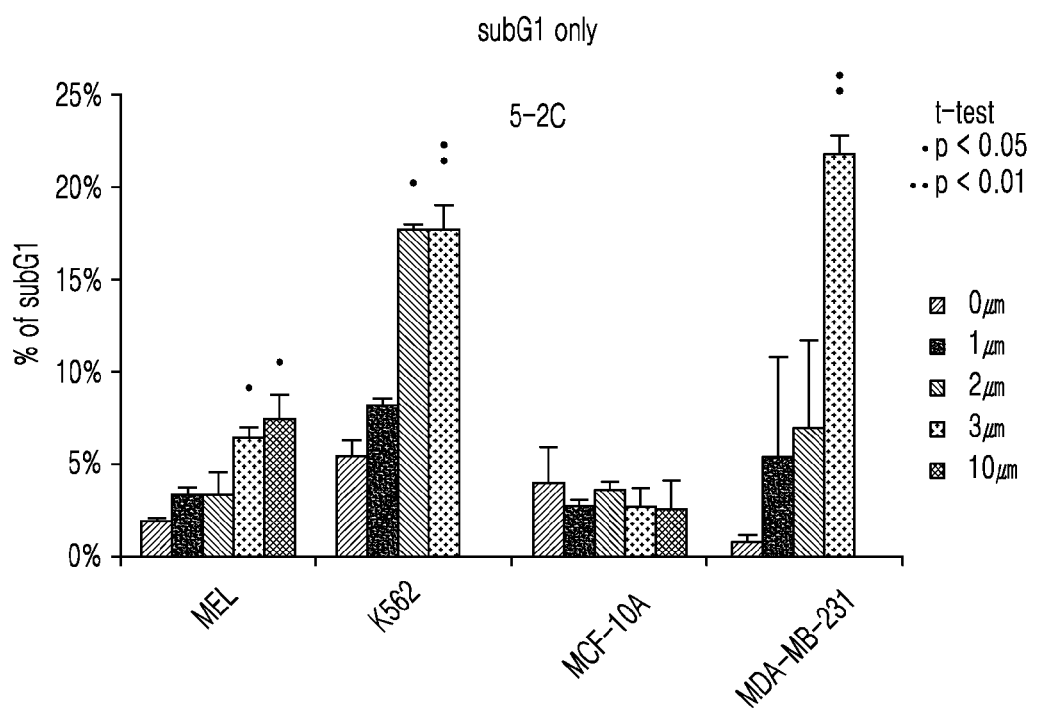
[Fig. 15c]

[Fig. 16a]
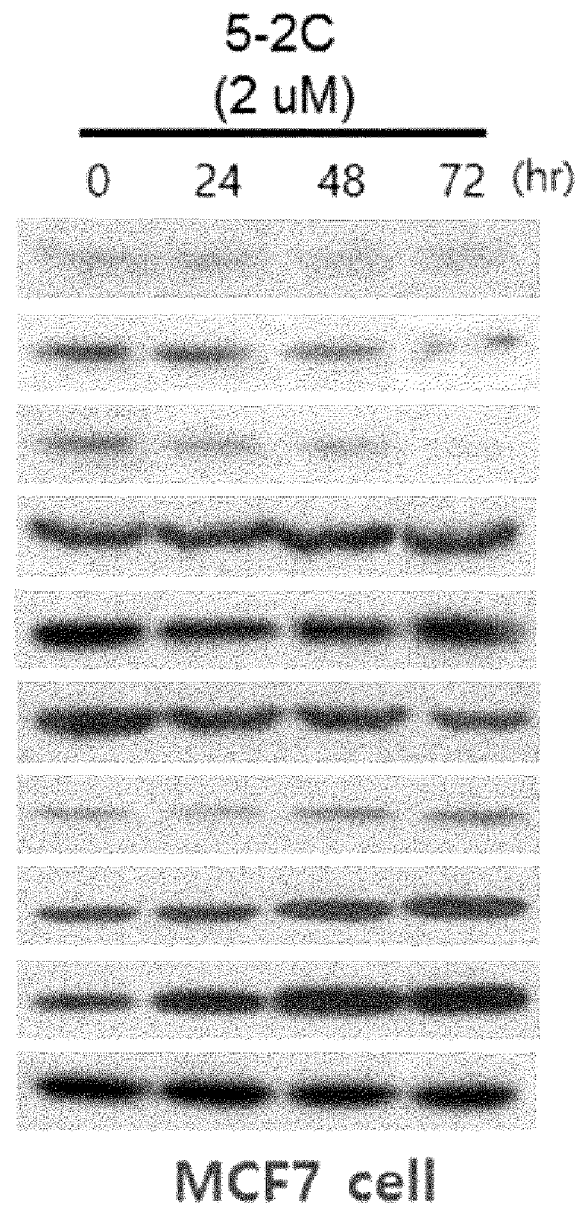

[Fig. 16b]
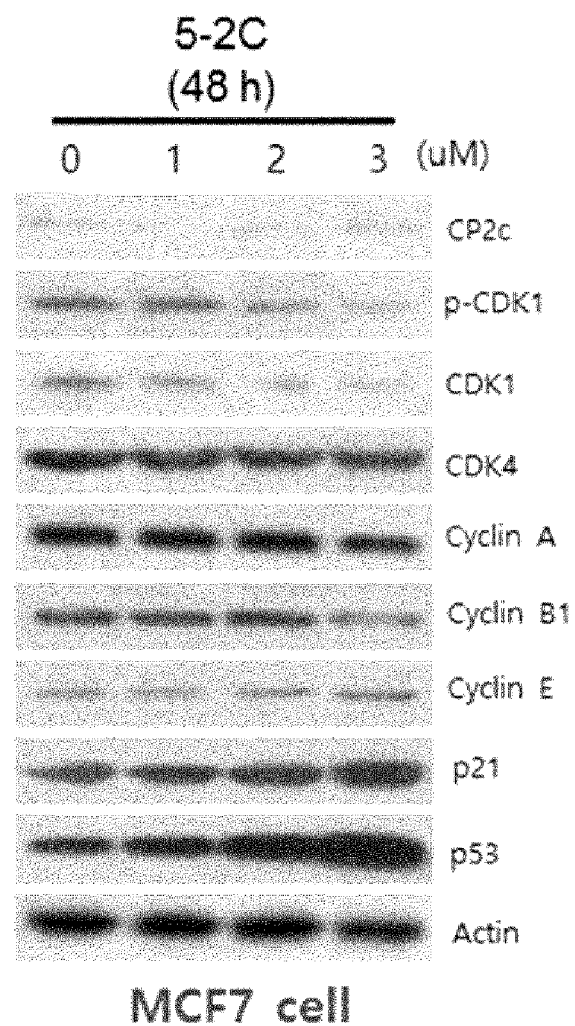

[Fig. 16c]
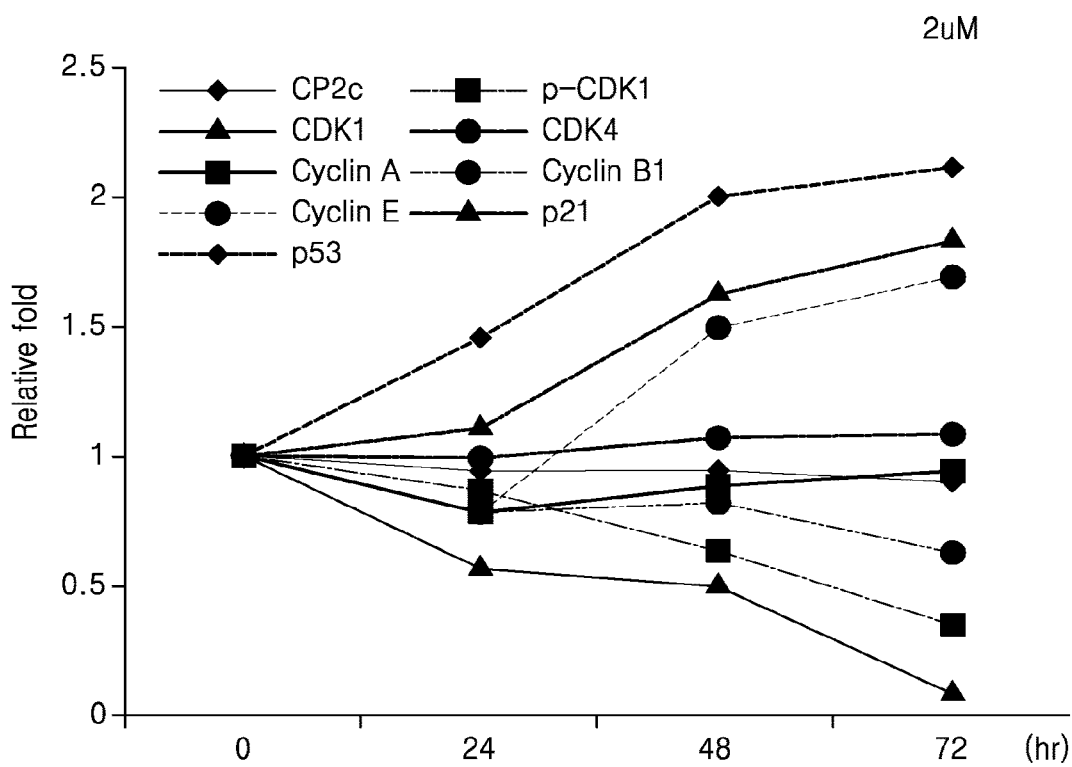
[Fig. 16d]
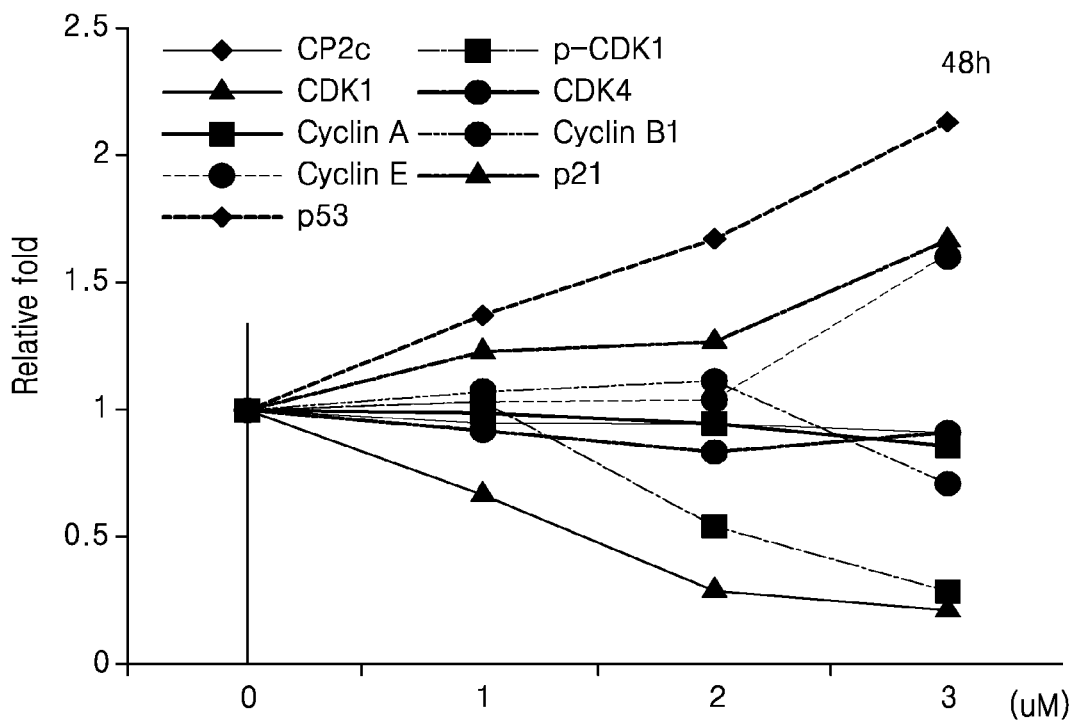

[Fig. 17]
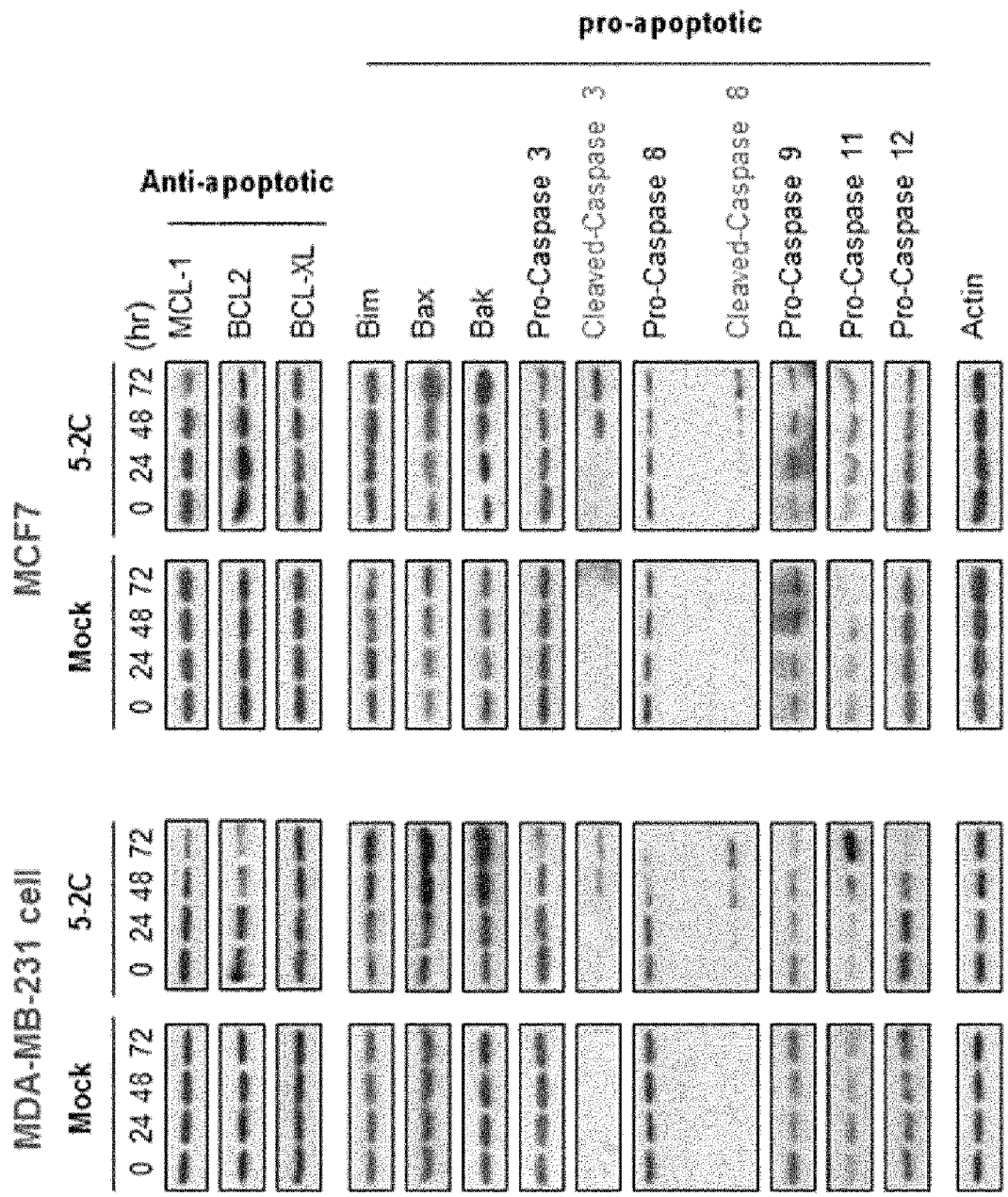

[Fig. 18]
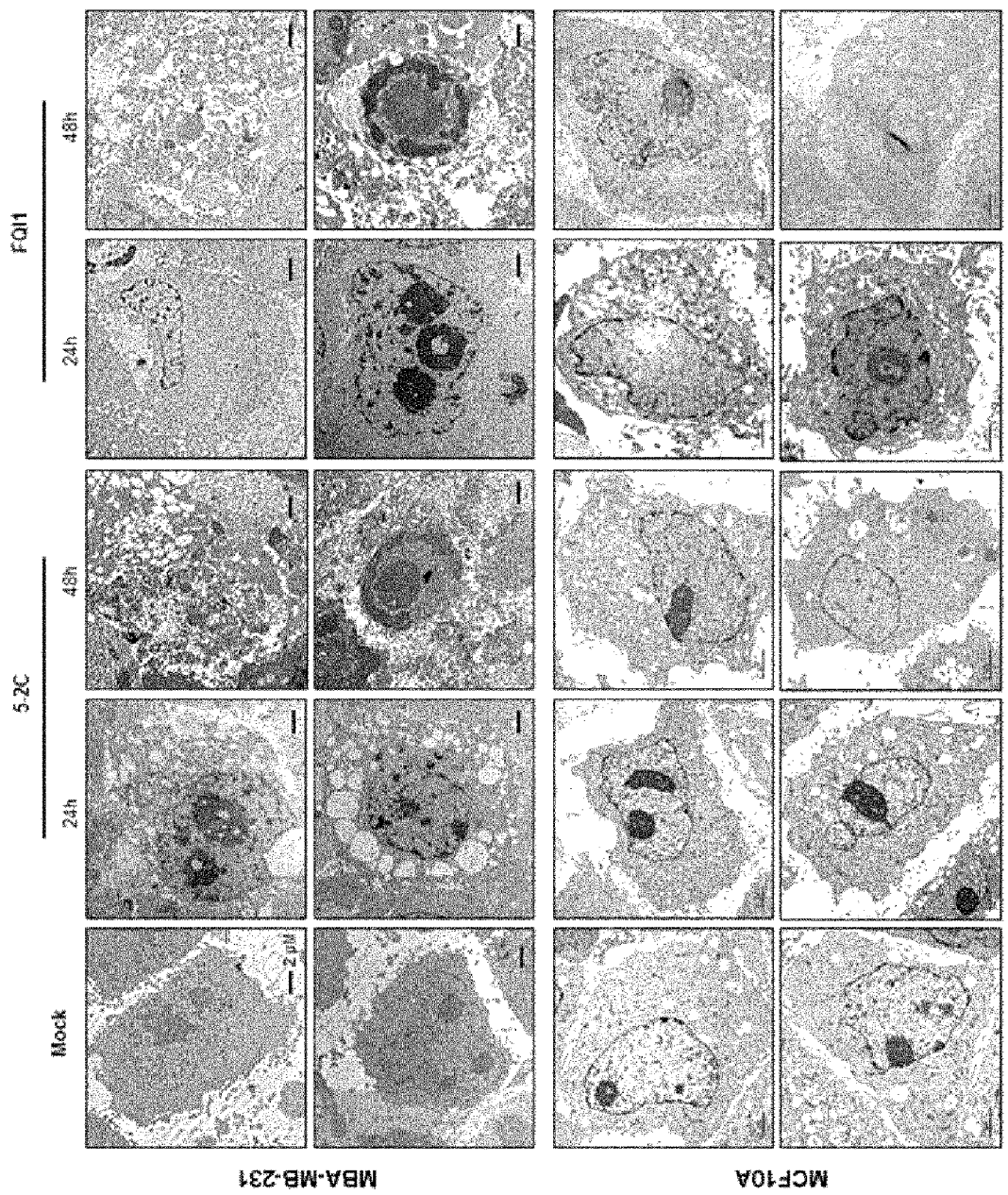

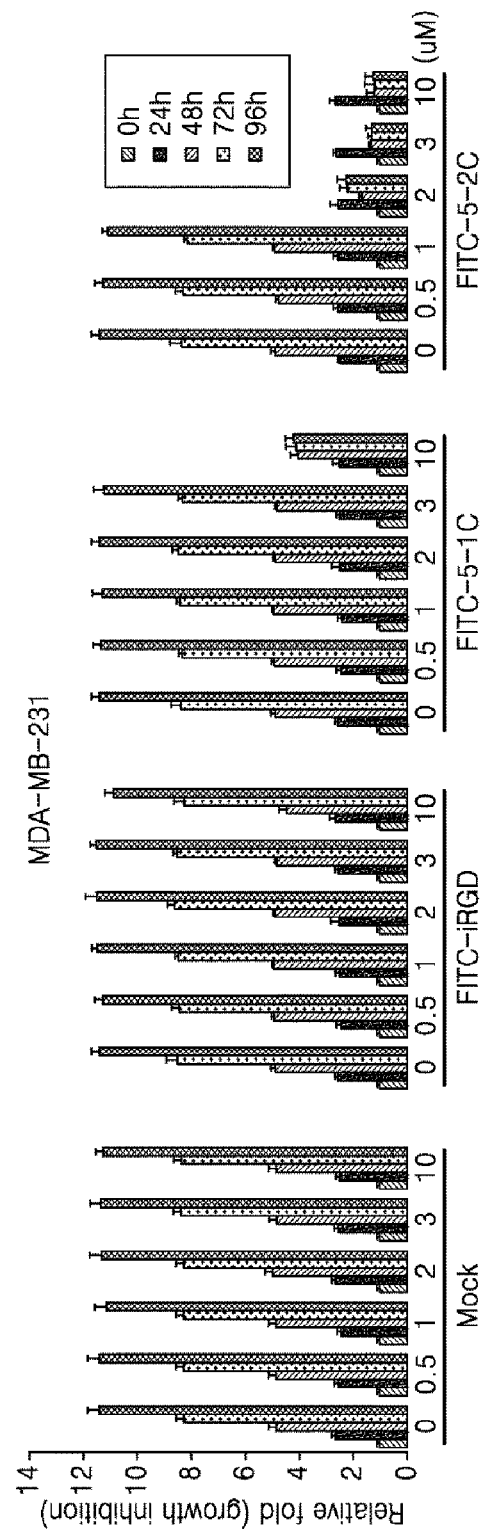
[Fig. 19a]

[Fig. 19b]
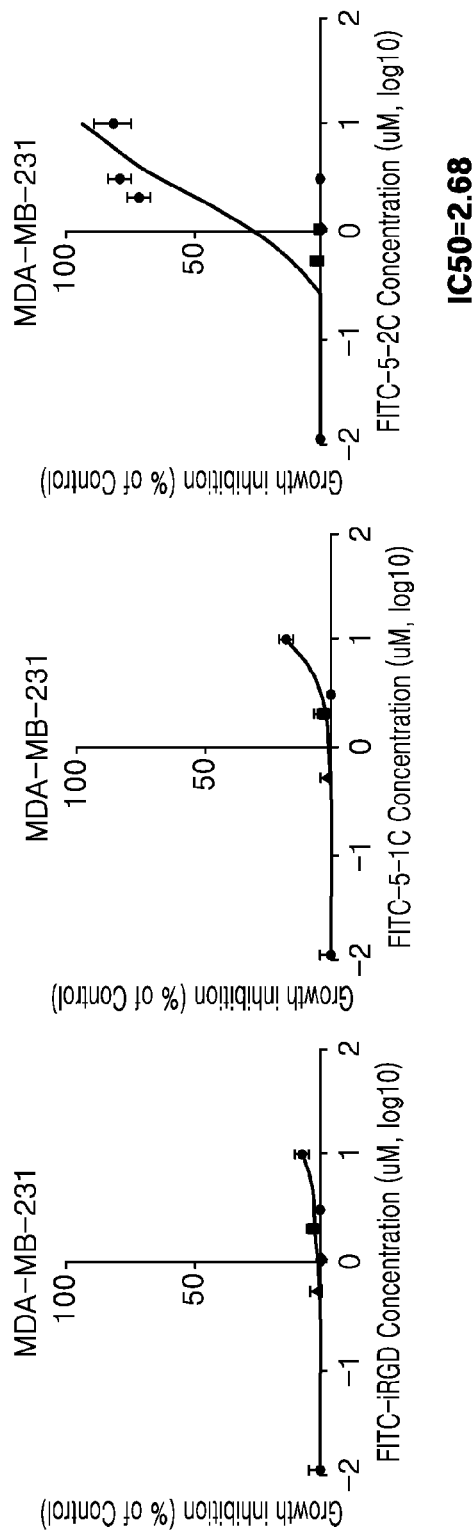

[Fig. 19c]
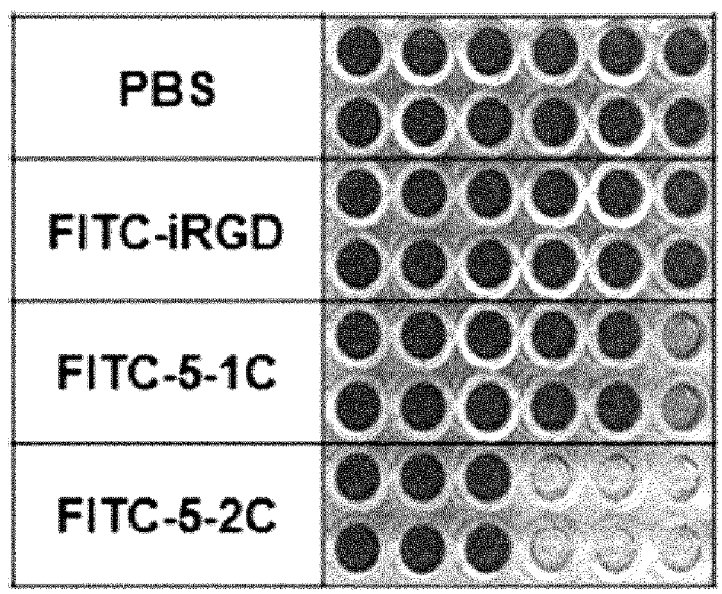

[Fig. 19d]
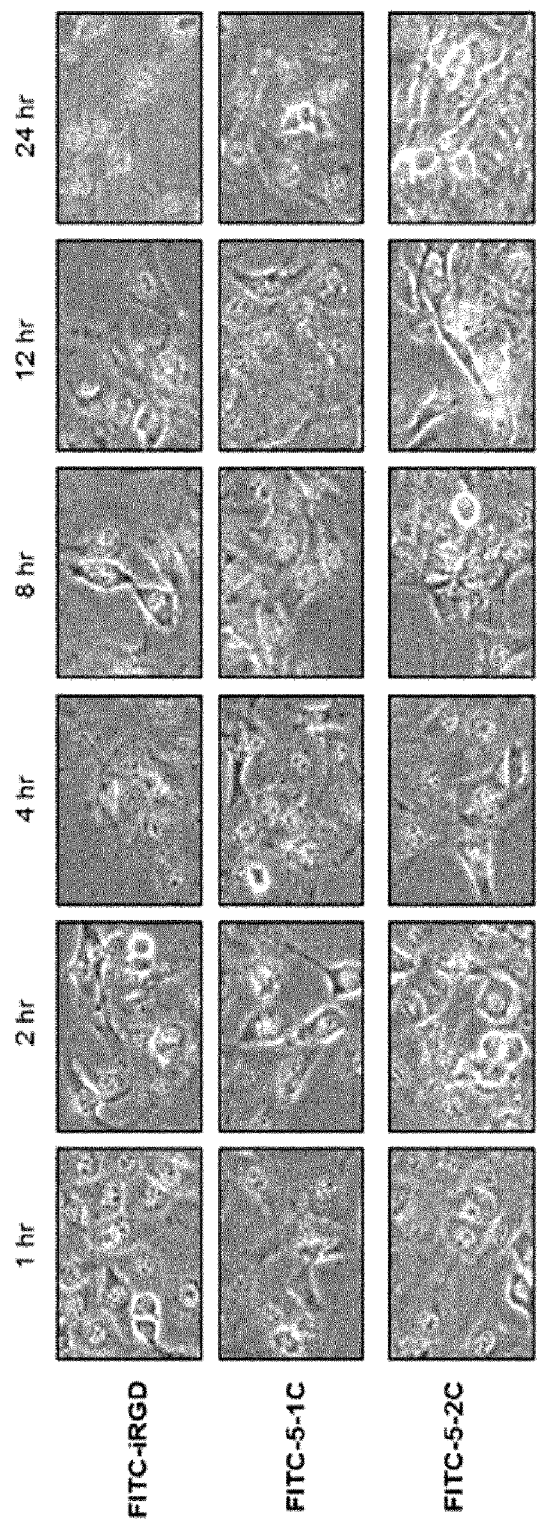

[Fig. 20a]
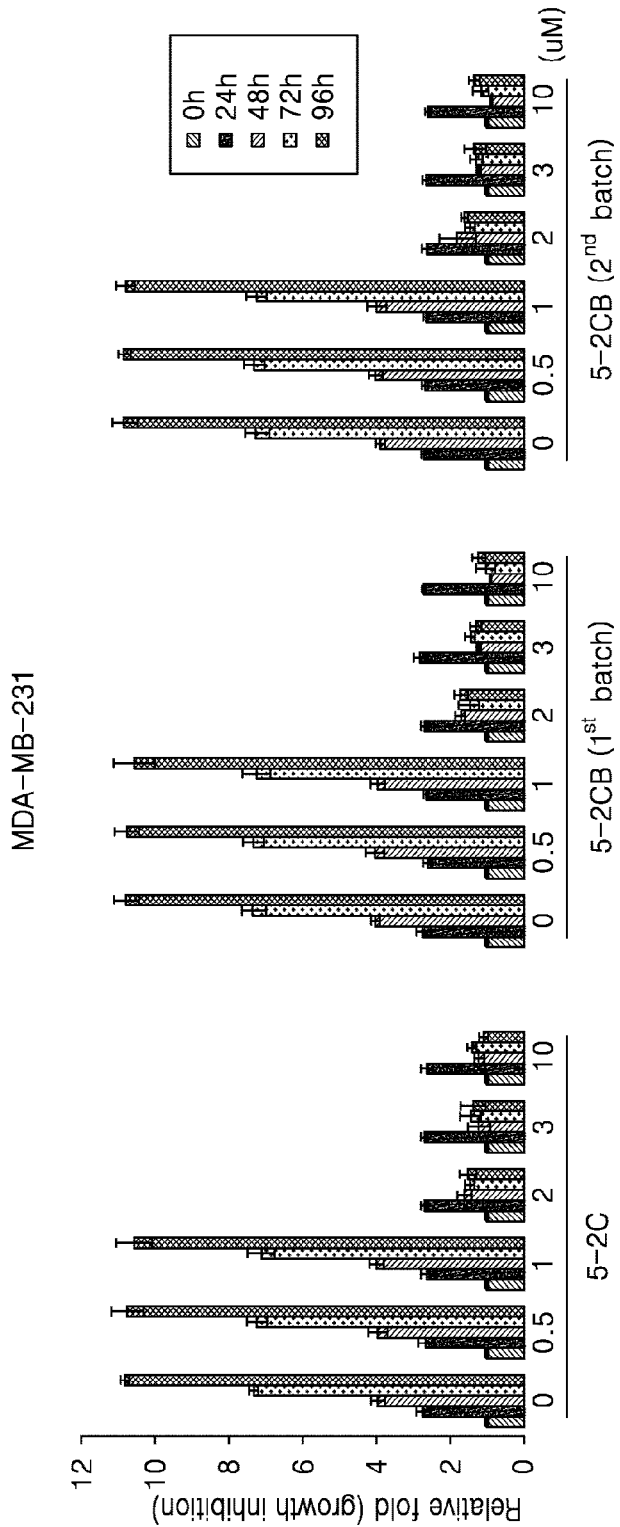

[Fig. 20b]
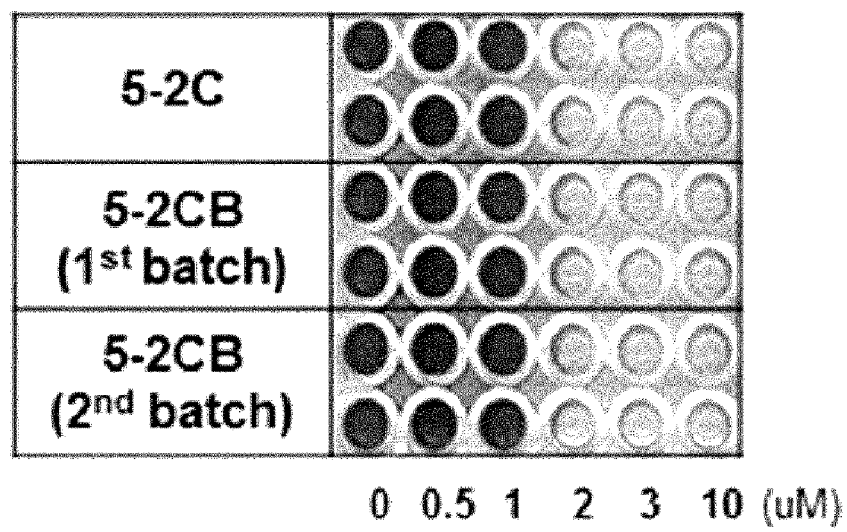

[Fig. 20c]
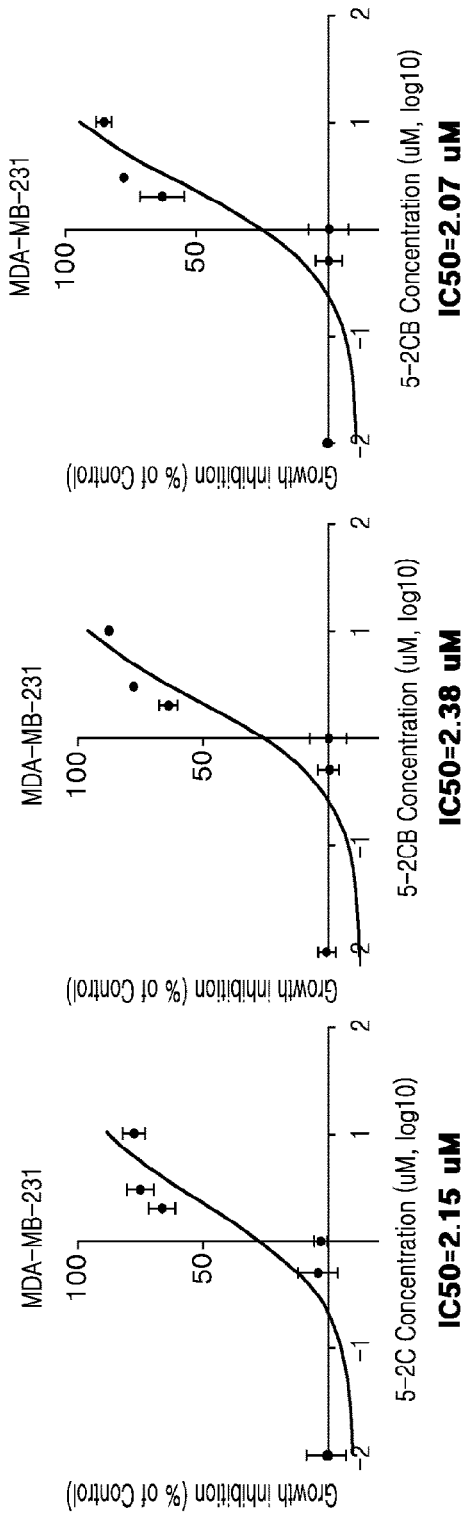

[Fig. 20d]
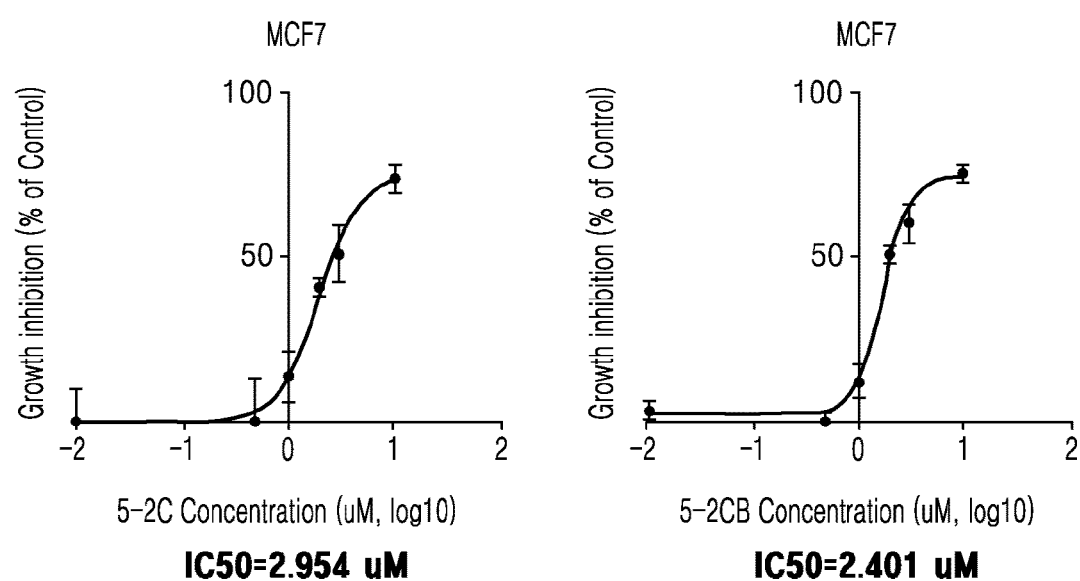

[Fig. 21a]
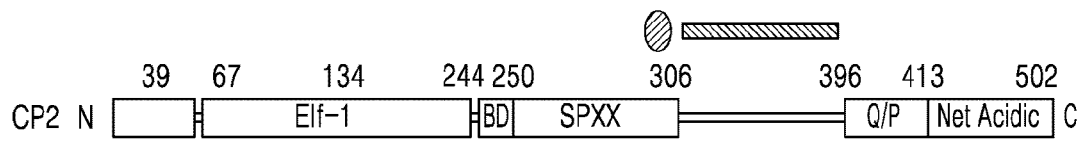
| | Mutant name | Mutain |
|---|---|---|
| 1 | GST-CP2c MUT #1 | H312A |
| 2 | GST-CP2c MUT #2 | E315A |
| 3 | GST-CP2c MUT #3 | D322A |
| 4 | GST-CP2c MUT #4 | E332A |
| 5 | GST-CP2c MUT #5 | H338A |
| 6 | GST-CP2c MUT #6 | R339A |
| 7 | GST-CP2c MUT #7 | R341A |
| 8 | GST-CP2c MUT #8 | R347A |
| 9 | GST-CP2c MUT #9 | D356A |
| 10 | GST-CP2c MUT #10 | K359A |
| 11 | GST-CP2c MUT #11 | R362A |
| 12 | GST-CP2c MUT #12 | D363A |
| 13 | GST-CP2c MUT #13 | D364A |
| 14 | GST-CP2c MUT #14 | D373A |
| 15 | GST-CP2c MUT #15 | R376A |
| 16 | GST-CP2c MUT #16 | K382A |
| 17 | GST-CP2c MUT #17 | R384A |
| 18 | GST-CP2c MUT #18 | R387A |
| 19 | GST-CP2c MUT #19 | R389A |

[Fig. 21b]
DNA IP (binding ability to the consensus CP2 binding site)
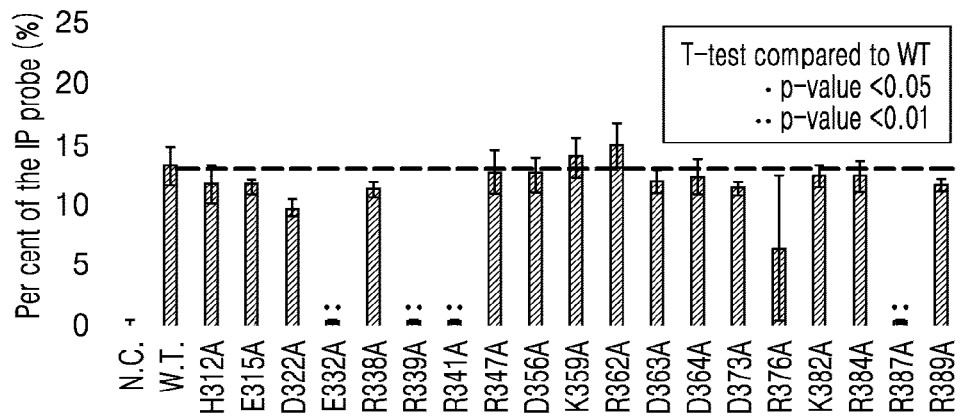
CP2c BS probe: 
[Fig. 21c]
ELISA (binding ability to the peptide 5-2)
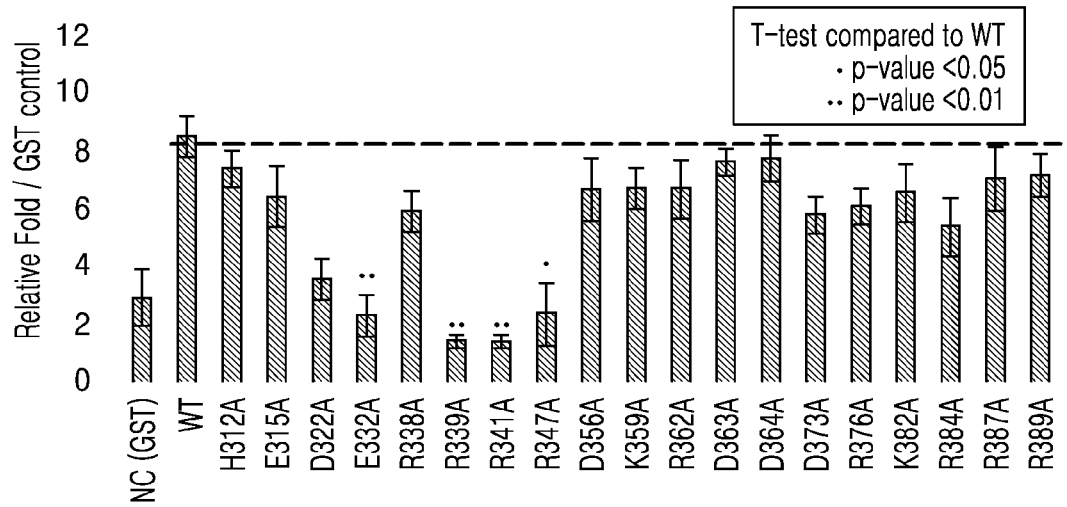
5-2CB peptide: 

[Fig. 21d]
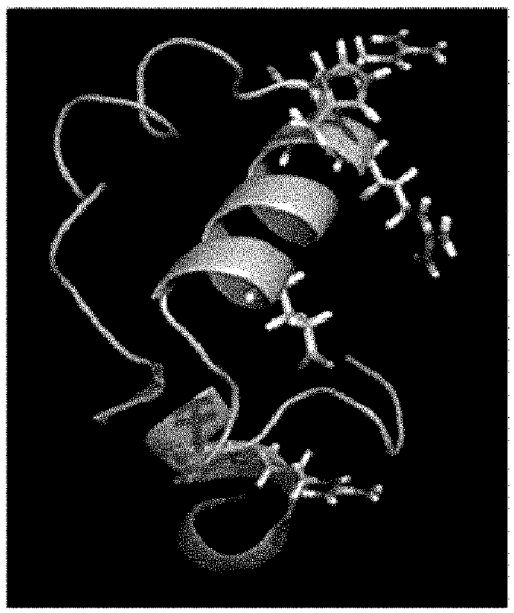 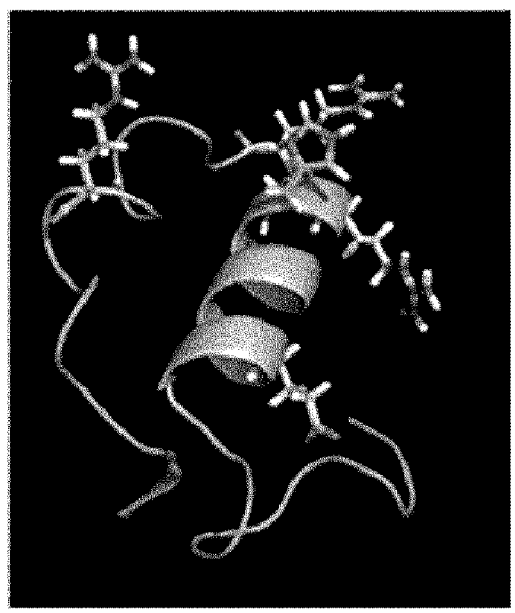
DNA binding      Peptide 5-2 binding

SEQUENCE LISTING

```
<160> NUMBER OF SEQ ID NOS: 19

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      artificially synthesized peptide
```

```
<400> SEQUENCE: 1

Asn Tyr Pro Gln Arg Pro
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      artificially synthesized peptide

<400> SEQUENCE: 2

Cys Arg Gly Asp Lys Gly Pro Asp Cys
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      artificially synthesized peptide
<220> FEATURE:
<221> NAME/KEY: MOD_RES
<222> LOCATION: (1)..(1)
<223> OTHER INFORMATION: 6-aminohexanoic acid
<220> FEATURE:
<221> NAME/KEY: MOD_RES
<222> LOCATION: (3)..(3)
<223> OTHER INFORMATION: 6-aminohexanoic acid

<400> SEQUENCE: 3

Lys Cys Lys Gly Gly Ser Gly Gly Ser
1               5

<210> SEQ ID NO 4
<211> LENGTH: 26
<212> TYPE: PRT
<213> ORGANISM: Artificial Sequence
<220> FEATURE:
<223> OTHER INFORMATION: Description of Artificial Sequence: Synthetic
      artificially synthesized peptide

<400> SEQUENCE: 4

Lys Ile Lys Lys Val Lys Lys Lys Gly Arg Lys Gly Ser Lys Ile Lys
1               5                   10                  15

Lys Val Lys Lys Lys Gly Arg Lys Gly Gly
            20                  25

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

His Glu Arg Arg Glu Ser
1               5

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (1)..(1)
<223> OTHER INFORMATION: 6-aminohexanoic acid
<220> FEATURE:
<221> NAME/KEY: MOD_RES
<222> LOCATION: (3)..(3)
<223> OTHER INFORMATION: 6-aminohexanoic acid

<400> SEQUENCE: 6

Lys Cys Lys Gly Gly Ser Gly Gly Ser Gly Gly
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

His Glu Arg Arg Glu Ser Asn Tyr Pro Gln Arg Pro
1               5                   10

<210> SEQ ID NO 8
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

His Glu Arg Arg Glu Ser Asn Tyr Pro Gln Arg Pro Cys Arg Gly Cys
1               5                   10                  15

Arg Gly Asp Lys Gly Pro Asp Cys
            20

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asn Tyr Pro Gln Arg Pro Cys Arg Gly Asp Lys Gly Pro Asp Cys
1               5                   10                  15

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

His Asn Met His Lys His Ser Ala Ser Arg Ile His
1               5                   10

<210> SEQ ID NO 11
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 11

His Lys Ser His Leu His Phe His Pro Pro Arg Pro
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

His Lys Phe His Gln His Arg Leu Pro His Leu Ala
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Val Trp Lys His Pro His His His His Tyr Lys Arg
1               5                   10

<210> SEQ ID NO 14
<211> LENGTH: 63
<212> TYPE: DNA
<213> ORGANISM: Unknown
<220> FEATURE:
<223> OTHER INFORMATION: Description of Unknown:
      Gata-1 enhancer sequence

<400> SEQUENCE: 14
cgagtccatc tgataagact tatctgctgc cccagagcag gccagagctg gcgtaagccc      60
cag                                                                   63

<210> SEQ ID NO 15
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cgagtccatc tgataagact tatctgctgc cacagagcag gtaagagctg gcgtaagccc      60
cag                                                                   63

<210> SEQ ID NO 16
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
cgagtccatc tgataagact tatctgctgc cccagattga gccagattga gcgtaagccc      60
```

```
<210> SEQ ID NO 17
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cgagtccatc tgataagact tatctgctgc cacagattga gtaagattga gcgtaagccc    60
cag                                                                 63

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
gatcccaagt tttactcggt agagcaagca caaaccagg                          39

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asn Tyr Pro Gln Arg Pro Cys Arg Gly Asp Lys Gly Pro Asp Cys Lys
1               5                   10                  15
```

PEPTIDE HAVING ANTICANCER ACTIVITY, AND PHARMACEUTICAL COMPOSITION AND DIETARY SUPPLEMENT COMPOSITION FOR PREVENTING AND TREATING CANCER, BOTH OF WHICH CONTAIN SAME AS ACTIVE INGREDIENT

CROSS-REFERENCE TO RELATED APPLICATION

This application claims priority to and is a 35 U.S.C. § 371 national phase application of PCT/KR2016/003179 (W02016/159627), filed on Mar. 29, 2016entitled "PEPTIDE HAVING ANTICANCER ACTIVITY, AND PHARMACEUTICAL COMPOSITION AND DIETARY SUPPLEMENT COMPOSITION FOR PREVENTING AND TREATING CANCER, BOTH OF WHICH CONTAIN SAME AS ACTIVE INGREDIENT", which application claims priority to and the benefit of Korean Patent Application No. 10-2015-0045480, filed Mar. 31, 2015 and Korean Patent Application No. 10-2016-0033118, filed Mar. 21, 2016; the disclosures of which is incorporated herein by reference in their entirety.

SEQUENCE STATEMENT

Incorporated by reference herein in its entirety is the Sequence Listing entitled "Q248544 SL.txt," created Jul. 26, 2019, 6,039bytes in size.

TECHNICAL FIELD

The present invention relates to a peptide with an anticancer activity, and cancer-preventing or -treating pharmaceutical and health functional-food compositions with this peptide as an active ingredient.

BACKGROUND ART

Heretofore, many anticancer agents, including natural products, proteinergic or peptidergic agents, and synthetic small molecules, have been developed and used. However, most of these anticancer agents cause serious side effects on living normal cells and may not act on some types of carcinomas. In general cases, the actions of the anticancer agents vary in patients with the same type of carcinoma. Under such circumstances, numerous world-wide studies have been conducted on development of new concepts of anticancer agent that can provide a solution to the aforementioned problems, is able to selectively remove cancer cells without affecting living normal cells, and even can eliminate any type of cancerous cells.

Transcription factor CP2c, also termed CP2, Tfcp2, LSF, LBP1 or UBP1, is widely expressed in mammals. The activity of CP2c is elaborately regulated as cells progress from the resting phase (G0) into the DNA replication phase (S) and is essential in allowing cells to effectively progress through the G1/S transition phase. The regulation of CP2c activity is mostly achieved through post-translational modifications, and its levels are kept low in the norm. However, since CP2c is overexpressed in tumor cells, it serves as an important oncogene that plays a key role in carcinogenesis. In this connection, a research group at Boston University reported Factor Quinolinone Inhibitor 1 (FQI1) as a substance that inhibits the cellular activity of CP2c in liver cancer cell lines. FQI1 and its derivatives were identified by chemical library screening and were successful in selectively inhibiting cancer cells in cell and transplanted mouse models without affecting normal cells (Grant et al., Antiproliferative small-molecule inhibitors of transcription factor LSF reveal oncogene addiction to LSF in hepatocellular carcinoma, Proc. Natl. Acad. Sci. 2012; 109(12): 4503-4508).

Further, the present inventors have reported four novel peptide motifs (HXPR, PHL, ASR, and PXHXH) that were shown by screening of a peptide display library to recognize distinct regions of CP2c (Kang et al., Identification and characterization of four novel peptide motifs that recognize distinct regions of the transcription factor CP2, FEBS Journal 2005; 272:1265-1277). The present inventors have suggested that CP2c recognizes specific binding motifs of a target protein and interacts with the protein to regulate various cellular activities. In their follow-up study, the present inventors have screened peptides inhibiting the binding of CP2c to DNA through in vitro assay based on a DNA immunoprecipitation method that is useful for highly specific and sensitive analysis of DNA-protein interactions, and as a result, found that Peptide 5 composed of 12 amino acids inhibits CP2c-DNA binding in a concentration-dependent manner (Kim et al., A DNA immunoprecipitation assay used in quantitative detection of in vitro DNA-protein complex binding, Analytical Biochemistry. 2013; 441: 147-151).

DETAILED DESCRIPTION OF THE INVENTION

Problems to be Solved by the Invention

The present invention has been made based on the results of studies conducted by the present inventors and is directed to providing a peptide for more effective suppression of the activity of CP2c, a known key transcription factor in various carcinomas, a pharmaceutical composition for preventing and treating cancer containing the peptide as an active ingredient, and a health functional food composition for preventing and treating cancer containing the peptide as an active ingredient.

Means for Solving the Problems

The present invention provides a peptide with prophylactic and therapeutic activities against cancer that binds to transcription factor CP2c and has the amino acid sequence set forth in SEQ ID NO: 1:

Asn-Tyr-Pro-Gln-Arg-Pro     (1)

According to one embodiment of the present invention, acetyl and amide groups may be linked (or bonded) to the N-terminal Asn residue and the C-terminal Pro residue of the peptide having the amino acid sequence set forth in SEQ ID NO: 1, respectively.

According to a further embodiment of the present invention, the C-terminal Pro residue of the peptide having the amino acid sequence set forth in SEQ ID NO: 1 may be linked with a peptide having the amino acid sequence set forth in SEQ ID NO: 2:

Cys-Arg-Gly-Asp-Lys-Gly-Pro-Asp-Cys     (2)

According to another embodiment of the present invention, when the peptide having the amino acid sequence set forth in SEQ ID NO: 2 is linked to the C-terminal Pro residue of the peptide having the amino acid sequence set forth in SEQ ID NO: 1, acetyl and amide groups may be bonded to the N-terminal Asn residue of the peptide having the amino acid sequence set forth in SEQ ID NO: 1 and the C-terminal Cys residue of the peptide having the amino acid sequence set forth in SEQ ID NO: 2, respectively.

According to another embodiment of the present invention, the C-terminal Pro residue and the N-terminal Asn residue of the peptide having the amino acid sequence set forth in SEQ ID NO: 1 may be linked with the peptide having the amino acid sequence set forth in SEQ ID NO: 2 and a peptide having the amino acid sequence set forth in SEQ ID NO: 3, respectively:

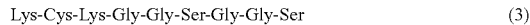

Lys-Cys-Lys-Gly-Gly-Ser-Gly-Gly-Ser  (3)

wherein the first amino acid Lys and the third amino acid Lys represent 6-aminohexanoic acid, and the N-terminal Lys residue of the peptide having the amino acid sequence set forth in SEQ ID NO: 3 may be linked with fluorescein isothiocyanate (FITC).

According to another embodiment of the present invention, when the peptide having the amino acid sequence set forth in SEQ ID NO: 2 is linked to the C-terminal Pro residue of the peptide having the amino acid sequence set forth in SEQ ID NO: 1 and the peptide having the amino acid sequence set forth in SEQ ID NO: 3 is linked to the N-terminal Asn residue of the peptide having the amino acid sequence set forth in SEQ ID NO: 1, an amide group may be linked to the C-terminal Cys residue of the peptide having the amino acid sequence set forth in SEQ ID NO: 2.

According to another embodiment of the present invention, the N-terminal Asn residue of the peptide having the amino acid sequence set forth in SEQ ID NO: 1 may be bonded with a peptide having the amino acid sequence set forth in SEQ ID NO: 4:

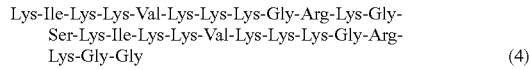

Lys-Ile-Lys-Lys-Val-Lys-Lys-Lys-Gly-Arg-Lys-Gly-
Ser-Lys-Ile-Lys-Lys-Val-Lys-Lys-Lys-Gly-Arg-
Lys-Gly-Gly  (4)

According to another embodiment of the present invention, when the peptide having the amino acid sequence set forth in SEQ ID NO: 4 is linked to the N-terminal Asn residue of the peptide having the amino acid sequence set forth in SEQ ID NO: 1, acetyl and amide groups may be linked to the N-terminal Lys residue of the peptide having the amino acid sequence set forth in SEQ ID NO: 4 and the C-terminal Pro residue of the peptide having the amino acid sequence set forth in SEQ ID NO: 1, respectively.

According to another embodiment of the present invention, the peptide having the amino acid sequence set forth in SEQ ID NO: 2 may be linked to the C-terminal Pro residue of the peptide having the amino acid sequence set forth in SEQ ID NO: 1 and biotin-tagged Lys may be linked to the ε-NH$_2$ of the C-terminal Cys residue of the peptide having the amino acid sequence set forth in SEQ ID NO: 2.

According to another embodiment of the present invention, when the peptide having the amino acid sequence set forth in SEQ ID NO: 2 is linked to the C-terminal Pro residue of the peptide having the amino acid sequence set forth in SEQ ID NO: 1 and biotin-tagged Lys is linked to the ε-NH$_2$ of the C-terminal Cys residue of the peptide having the amino acid sequence set forth in SEQ ID NO: 2, acetyl and amide groups may be linked to the N-terminal Asn residue of the peptide having the amino acid sequence set forth in SEQ ID NO: 1 and the biotin-tagged C-terminal Lys linked to the ε-NH$_2$ of the C-terminal Cys residue of the peptide having the amino acid sequence set forth in SEQ ID NO: 2, respectively.

The present invention also provides a pharmaceutical composition for preventing and treating cancer containing at least one of the peptides modulating CP2c activity as an active ingredient.

The present invention also provides a health functional food composition for preventing and treating cancer containing at least one of the peptides modulating CP2c activity as an active ingredient.

Effects of the Invention

The peptide or the pharmaceutical composition penetrates the membranes of cancer cells with very high efficiency, is capable of specific binding to CP2c, and can inhibit the ability of CP2c to bind to DNA. Therefore, the peptide or the pharmaceutical composition of the present invention has the ability to inhibit the activity of CP2c. Due to its ability, the peptide or the pharmaceutical composition of the present invention impedes CP2c-mediated cancer cell-specific transcriptional activity, thus being effective in specific treatment of cancer cells. In addition, the peptide or the pharmaceutical composition of the present invention can be used to prevent cancer. Furthermore, the peptide of the present invention can be used as a health food additive for cancer prevention.

BRIEF DESCRIPTION OF THE DRAWINGS

FIG. 1 is a schematic representation of the full-length amino acid sequence of CP2c composed of a total of 6 regions and amino acid sequences of various CP2c mutants in which the N- and C-termini of the CP2c sequence are deleted. FIG. 1 discloses SEQ ID NOS 7 and 10-13, respectively, in order of appearance.

FIG. 2 shows the binding affinities of DNA-CP2c complexes measured by DNA immunoprecipitation (DIP) assay for five CP2c-binding peptides (Peptide 5, Peptide 8, Peptide 13, Peptide 21, and Peptide 31).

FIG. 3 shows the binding affinities of DNA-CP2c complexes by DIP assay for Peptide 5, Peptide 8, Peptide 5-1, and Peptide 5-2.

FIGS. 4a to 4e are microscopy images taken after culture of FQI1, Peptide 5C, and Peptide 5-2C with various cancer cell lines and normal human stem cells and differentiated cells: specifically, the images of FIG. 4a show liver cancer cell lines (HepG2, Hep3B), a human embryonic kidney cell line (293T), breast cancer cell lines (MVCF7, MDA-MB-231), blood cancer cell lines (K562, MEL, HEL, HL60), and glioblastoma cell lines (U251, U373MG, U87MG); the images of FIG. 4b show epidermal cell lines (MCF10A, BEAS2B) from various tissue sources, primarily cultured mouse T lymphocytes (resting and activated T lymphocytes), and human mesenchymal stem cells (hMSCs); the images of FIG. 4c show MCF7, 293T, and MBA-MB-231 cell lines during mammosphere culture; the images of FIG. 4d show human embryonic stem cells (hESCs) during co-culture with fibroblasts; and the images of FIG. 4e show human hematopoietic progenitor cells (HPCs) and cells derived therefrom during differentiation into erythrocytes (cells on days 3, 7, and 14 after differentiation induction).

FIGS. 5a to 5j show the relative viabilities of HepG2 cell line and Hep3B cell line (5a), MCF7 cell line and MDA-MB-231 cell line (5b), U251 cell line, U87MG cell line, and U343 cell line (5c), K562 cell line, HEL cell line, and HL60 cell line (5d), 293T cell line (5e), MCF10A cell line and BEAS2B cell line (5f), primarily cultured mouse T lymphocytes (resting and activated T lymphocytes) (5g), hMSC cell line (5h), hESC cell line (5i), hematopoietic progenitor cells (HPCs) and cells derived therefrom during induction of differentiation into erythrocytes (on days 3, 7, and 14) (5j) after one-time treatment with FQI1, Peptide 5C, and Peptide 5-2C at increasing concentrations, and FIG. 5k shows images of well plates 96 h after the peptide treatment.

FIGS. 6a and 6b are images comparing the expression levels of CP2c protein in 6 colon cancer cell lines, 6 lung cancer cell lines, 3 breast cancer cell lines, 3 glioblastoma cell lines, and one cervical cancer cell line (6a) and blood cancer cell lines (MEL, K562, HEL, HL60), liver cancer cell lines (HepG2, Hep3B), a human epidermoid carcinoma cell line (A431), a colon cancer cell line (HCT116), epidermal cell lines (293T, BEAS2B, MCF10A) from various tissue sources, and a hMSC cell line (6b), as determined by Western blotting.

FIGS. 7a and 7b show graphs for calculating $IC_{50}$ values of Peptide 5-2C for the cell lines shown in FIG. 5 after treatment of the cell lines with Peptide 5-2C and the calculated $IC_{50}$ values: specifically, FIG. 7a shows graphs for calculating $IC_{50}$ values at 48 h after each cell line was treated once with Peptide 5-2C and the calculated $IC_{50}$ values; and FIG. 7b shows graphs for calculating $IC_{50}$ values at 48 h and 96 h after glioblastoma cell lines U343, U373MG, U251, and U87MG were treated once with Peptide 5-2C and the calculated $IC_{50}$ values.

FIG. 8 shows graphs for calculating $IC_{50}$ values at 48 h after treatment of MCF10A cell line and BEAS2B cell line with FQI1, Peptide 5C, and Peptide 5-2C and the calculated $IC_{50}$ values.

FIGS. 9a to 9f show the relative viabilities of MDA-MB-231 cell line and MCF7 cell line (9a), U343 cell line and U87MG cell line (9b), HCT116 cell line and HT29 cell line (9c), 293T cell line and HepG2 cell line (9d), U937 cell line, Jurkat cell line, HL60 cell line, and HEL cell line (9e), and MCF10A cell line and BEAS2B cell line (9f) after one-time treatment with Peptide 5-2C and Peptide 5-2D at increasing concentrations, and FIG. 9g shows images of well plates 96 h after the peptide treatment.

FIG. 10 shows graphs for calculating $IC_{50}$ values of Peptide 5-2C and Peptide 5-2D for the cell lines shown in FIG. 9 after treatment of the cell lines with Peptide 5-2C and Peptide 5-2D and the calculated $IC_{50}$ values.

FIGS. 11a to 11g show the ability of Peptide 5-2C to inhibit tumor growth and the physiological properties of Peptide 5-2C in mouse models transplanted with U343 glioblastoma cell line. U343 glioblastoma cell line ($2.5 \times 10^6$ cells/50 μl) was injected subcutaneously into the backs of male BALB/C nude mice (n=6/group), Peptide 5-2C (3 mg/kg) was directly injected into the tumor sites every three days from the time when the tumor sizes increased to about 8 mm², the body weights of the mice and the volumes of the tumors were measured, the mice were sacrificed on day 70 after the peptide injection, and the tumors, blood, and major organs were excised. Specifically, FIG. 11a shows the volumes of the tumors during the experimental period, FIG. 11b shows changes in the body weight of the mice, FIG. 11c shows images of the mice on day 70 after the peptide administration, FIG. 11d shows images of the excised tumors, FIG. 11e shows the weights of the tumors excised from the mice and their average values, FIG. 11f shows various standard blood indices of the mice in the control and peptide treated groups, and FIG. 11g shows H/E-stained images of the major organs (spleens, livers, lungs, and kidneys).

FIGS. 12a to 12d show the ability of Peptide 5-2C to inhibit tumor growth and the physiological properties of Peptide 5-2C in mouse models transplanted with A431 human epidermoid carcinoma cell line. A431 cell line ($5 \times 10^6$ cells/100 μl) was injected subcutaneously into the backs of male BALB/C nude mice (n=4/group), Peptide 5-2C ($1 \times IC_{50}$; 1.7 mg/kg, $2 \times IC_{50}$; 3.5 mg/kg) was injected every other day into the mice through the tail veins a total of five times from the time when the tumor sizes increased to about 50 mm², the tumor volumes were measured, the mice were sacrificed on day 13 after the peptide injection, and the tumors and major organs were excised. FIG. 12a shows the volumes of the tumors during the experimental period, FIG. 12b shows images of the mice and the excised tumors, FIG. 12c shows the weights of the tumors excised from the mice and their average values, and FIG. 12d shows H/E-stained images of the major organs (spleens, livers, lungs, blood vessels, and muscles) of the groups.

FIGS. 13a to 13d show the ability of Peptide 5-2C to inhibit metastasis to lung tissue and tumor growth and the physiological properties of Peptide 5-2C in animal models transplanted with MDA-MB-231 cell line (LM1 cells) capable of metastasizing to lung tissue. MDA-MB-231 cell line (LM1 cells; $1 \times 10^6$ cells/40 μl) was injected into the mammary fat pads of 12-week-old female BALB/C nude mice (n=5/group), Peptide 5-2C ($1 \times IC_{50}$; 1.7 mg/kg=52 μg/mouse, $2 \times IC_{50}$; 3.5 mg/kg=104 μg/mouse) was injected every three days into the mice through the tail veins a total of five times from the time when the tumor sizes increased to about 50 mm², the tumor volumes were measured, the mice were sacrificed on day 30 after the peptide injection, and the tumors and major organs were excised. FIG. 13a shows images of the mice with tumors and the excised tumors, FIG. 13b shows the weights of the tumors excised from the mice and their average values, FIG. 13c shows means and standard deviations of the number of the tumor foci metastasized to the lung in the control and peptide-treated groups, and FIG. 13d shows the blood indices of the mice in the control and peptide treated groups.

FIGS. 14a to 14e show the expression profiles of luciferase reporters for normal CP2c binding sites and sequences of CP2c mutants in order to analyze the transcriptional activity of CP2c by Peptide 5C and Peptide 5-2C. FIG. 14e discloses SEQ ID NOS 14-17, respectively, in order of appearance.

FIGS. 15a to 15c show the results of cell cycle analysis for various cell lines (MEL, K562, MCF-10A, MDA-MB-231) by FACS at 48 h after treatment of the cell lines with Peptide 5-2C at various concentrations of 0, 1, 2, 3, and 10 μM in order to analyze the influence of Peptide 5-2C on cell cycle: specifically, FIG. 15a shows the distributions of cells depending on the amount of DNA during FACS; FIG. 15b shows quantified distributions of cells in different cell cycle phases; and FIG. 15c shows enlarged distributions of cells in subG1 phase showing apoptosis.

FIGS. 16a to 16d show the expression profiles of cell cycle-related marker genes when MCF7 cell line was treated with Peptide 5-2C at different concentrations for different periods of time: specifically, FIG. 16a shows time-dependent expression profiles of various cell cycle-related marker gene proteins when treated with 2 μM Peptide 5-2C for 72 h, as determined by Western blotting, FIG. 16b shows the expression profiles of cell cycle-related marker gene proteins after treatment with Peptide 5-2C at various concentrations (0, 1, 2, and 3 μM) for 48 h, as determined by Western blotting; and FIGS. 16c and 16d show quantified changes in the expression of the marker gene proteins in FIGS. 16a and 16b, respectively.

FIG. 17 show time-dependent expression profiles of apoptosis-related marker gene proteins after treatment of MDA-MB-231 cell line and MCF7 cell line with 2 μM Peptide 5-2C.

FIG. 18 shows electron microscopy images showing cell morphologies 24 h and 48 h after treatment of MDA-MB-231 cell line and MCF10A cell line with 2 μM Peptide 5-2C: cells treated with physiological saline and cells treated with 2 μM FQI1 were used as negative and positive controls, respectively.

FIGS. 19a to 19d are graphs confirming intracellular migration pathways of FITC-conjugated Peptide 5-2C in MDA-MB-231 cell line with the passage of time: specifically, FIG. 19a shows changes in cell growth rate after MDA-MB-231 cell line was treated with physiological saline and FITC-conjugated-iRGD, FITC-5-1C, and FITC-5-2C peptides at concentrations of 0, 0.5, 1, 2, 3, and 10 μM for 96 h, as determined by MTT assay; FIG. 19b shows graphs for calculating $IC_{50}$ values of the peptides in the treated groups at 48 h after the treatment and the calculated $IC_{50}$ values; FIG. 19c shows images of well plates showing examples of MTT assay at 96 h; and FIG. 19d shows images showing time-dependent intracellular distributions of the FITC-conjugated peptides (each 2 μM) for 24 h after treatment with the peptides.

FIGS. 20a to 20d compare the influence of Peptide 5-2CB (biotin-tagged Peptide 5-2C) on cancer cell survival with that of Peptide 5-2C: specifically, FIG. 20a shows the relative viabilities of MDA-MB-231 cell line after one-time treatment with Peptide 5-2C and two different batches of Peptide 5-2CB at increasing concentrations; FIG. 20b shows images of well plates 96 h after the peptide treatment; FIG. 20c shows graphs for calculating $IC_{50}$ values at 48 h after treatment of MDA-MB-231 cell line with the peptides and the calculated $IC_{50}$ values; and FIG. 20d shows graphs for calculating $IC_{50}$ values at 48 h after treatment of MCF7 cell line with the peptides and the calculated $IC_{50}$ values.

FIGS. 21a to 21d show the results of a series of experiments for identifying important amino acids for DNA binding and Peptide 5-2C binding in a CP2c protein region (corresponding amino acids 306 to 396) to which Peptide 5-2C binds: specifically, FIG. 21a shows a list of regions to which Peptide 5-2C binds and 19 GST-fusion mutants produced by substituting polar amino acids in the amino acid sequence of the site with alanine; FIG. 21b shows the results of DNA-IP for the binding of GST-fusion proteins purified from mutants overexpressed in E. coli using GST antibody beads with a DNA probe of a CP2c binding site present in a radioactively labeled alpha-globin promoter. FIG. 21b discloses SEQ ID NO: 18; FIG. 21c shows the results of direct ELISA assay for the binding of purified GST-fusion mutant proteins with Peptide 5-2C. FIG. 21c discloses SEQ ID NO: 19; and FIG. 21d shows important amino acids for DNA binding and Peptide 5-2C binding to tertiary structures, which were predicted based on the Rosetta modeling algorism for 306-396 amino acid region of CP2c.

BEST MODE FOR CARRYING OUT THE INVENTION

The present invention will now be described in more detail.

The present invention provides a peptide with therapeutic activities against cancer that binds to transcription factor CP2c and has the amino acid sequence set forth in SEQ ID NO: 1:

Asn-Tyr-Pro-Gln-Arg-Pro (1)

The peptide having the amino acid sequence set forth in SEQ ID NO: 1 (hereinafter also referred to as "Peptide 5-2") is composed of six amino acids and interacts with CP2c protein to regulate the activity of the protein, as can be specifically seen from the Examples section that follows. CP2c is a protein that is specifically overexpressed in tumor cells. This activity regulation eventually leads to anticancer effects.

As described above, the present inventors have found that Peptide 5 composed of 12 amino acids inhibits CP2c-DNA binding in a concentration dependent manner (Kim et al., A DNA immunoprecipitation assay used in quantitative detection of in vitro DNA-protein complex binding, *Analytical Biochemistry*. 2013; 441: 147-151). However, as can be seen from the results of the following Examples section, Peptide 5 composed of 12 amino acids inhibits cell growth and induces apoptosis even in normal control cell lines whereas Peptide 5-2 of the present invention composed of 6 amino acids (6 downstream amino acids of Peptide 5) does not substantially induce the growth inhibition and apoptosis of normal control cell lines. On the other hand, Peptide 5-1 composed of the 6 upstream amino acids of Peptide 5 fails to inhibit CP2c-DNA binding and treatment with Peptide 5-1 does not affect the growth inhibition and apoptosis induction of cancer cell lines as well as normal cell control groups. Therefore, the peptide 5-2 of the present invention presents the possibility of an ideal cancer treatment due to its specific activity against cancer cells without affecting normal cells.

Peptide 5-2 of the present invention may be imparted with various functionalities by modification. For example, Peptide 5-2 of the present invention may be modified into the following peptides.

First, the peptide of the present invention may be imparted with high stability by modification. To this end, acetyl and amide groups are linked to the N-terminal Asn residue and the C-terminal Pro residue of the peptide having the amino acid sequence set forth in SEQ ID NO: 1, respectively. This modified peptide is also referred to as 'Peptide 5-2A'.

Next, the efficiency of the cell penetrability of the peptide having the amino acid sequence set forth in SEQ ID NO: 1 may be increased by modification. To this end, the iRGD peptide sequence (CRGDKGPDC (SEQ ID NO: 2)) responsible for binding to the neuropilin 1receptor is linked to the C-terminal Pro residue of the peptide having the amino acid sequence set forth in SEQ ID NO: 1. This modified peptide is also referred to as 'Peptide 5-2B'. Likewise, acetyl and amide groups may be bonded to the N-terminal Asn residue and the C-terminal Cys residue of Peptide 5-2B, respectively. This modified peptide is also referred to as 'Peptide 5-2C'.

To easily track the intracellular migration pathways and biodistributions of the Peptide 5-2 or 5-2C by fluorescence/confocal microscopy and bioimaging, a FITC fluorescent dye-containing compound (FITC-(6-aminohexanoic acid)-Cys-(6-aminohexanoic acid)-Gly-Gly-Ser-Gly-Gly-Ser-Gly-Gly (SEQ ID NO: 6)) may be further linked to the N-terminal Asn residue of Peptide 5-2 or 5-2C. This modified peptide is also referred to as 'Peptide FITC-5-2' or 'Peptide FITC-5-2C'. Likewise, an amide group may be bonded to the C-terminal Cys of Peptide FITC-5-2C.

Furthermore, in order to increase the blood-brain barrier (BBB) and cell penetration efficiencies of the peptide, the dNP2 peptide sequence (KIKKVKKKGRKGSKIKKVKK-KGRKGG (SEQ ID NO: 4); Lim et al., Nat Commun (2015) 6, 8244) having such functions may also be linked to the N-terminal Asn residue of Peptide 5-2. This modified peptide is also referred to as 'Peptide 5-2D'. Likewise, acetyl and amide groups may be linked to the N-terminal Lys residue and the C-terminal Pro residue of the Peptide 5-2D, respectively.

To facilitate the analysis of binding between Peptide 5-2C and transcription factor CP2c, biotin-tagged Lys may also be linked to the ε-NH$_2$ of the C-terminal Cys residue of Peptide 5-2C. This modified peptide is also referred to as 'Peptide 5-2CB'. Likewise, acetyl and amide groups may be linked to the N-terminal Asn residue and the C-terminal Lys residue of the Peptide 5-2CB, respectively.

The present invention also provides a pharmaceutical composition for preventing and treating cancer containing the peptide having the amino acid sequence set forth in SEQ ID NO: 1 as an active ingredient and a health functional food composition for preventing and treating cancer containing the peptide having the amino acid sequence set forth in SEQ ID NO: 1 as an active ingredient.

As used herein, the term "treatment" means all of the actions in which the symptoms of cancer have taken a turn for the better or been modified by the administration of the peptide or the pharmaceutical composition according to the present invention.

As used herein, the term "administration" means the introduction of a substance, that is, the peptide derivative or the pharmaceutical composition of the present invention, into a subject by any suitable method. The peptide derivative or the pharmaceutical composition of the present invention may be administered via any of the common routes as long as it is able to reach a desired tissue. Specifically, a variety of administration routes are contemplated, including intraperitoneally, intravenously, intramuscularly, subcutaneously, intradermally, orally, topically, intranasally, intrapulmonarily and intrarectally, but the present invention is not limited to these administration routes. Since the orally administered peptide of the present invention is not digested, the composition of the present invention is preferably coated with an active drug or protected from degradation in the stomach. Preferably, the composition of the present invention may be administered in the form of an injectable preparation. The pharmaceutical composition of the present invention may be administered using a certain device capable of delivering the active substance to target cells.

As used herein, the term "containing as an active ingredient" means the presence of an amount sufficient to treat a disease in a reasonable beneficial/risk ratio applicable to any medical treatment. The effective dosage level of the composition may be determined depending on factors, including the type and severity of the disease, the activity of the drug, the patient's sensitivity to the drug, the time of administration, the route of administration, excretion rate, the duration of treatment, drugs used in combination with the composition, and other factors known in the medical field. The peptide or the pharmaceutical composition of the present invention may be administered individually or in combination with other therapeutic agents and may be administered sequentially or simultaneously with conventional therapeutic agents. The peptide or the pharmaceutical composition of the present invention may be administered in single or multiple dosages. It is important to administer the peptide or the pharmaceutical composition of the present invention in the minimal amount that can exhibit the maximum effect without causing side effects, in view of all the above-described factors. The amount of the peptide or the pharmaceutical composition according to the present invention can be easily determined by those skilled in the art. The dose and administration frequency of the pharmaceutical composition according to the present invention are determined depending on the kind of the drug as an active ingredient together with various relevant factors, including the type of disease to be treated, the route of administration, the age, sex, and weight of patient, and the severity of disease.

The pharmaceutical composition of the present invention may further include one or more pharmaceutically acceptable carriers so long as it contains the peptide of the present invention as an active ingredient. Examples of suitable pharmaceutically acceptable carriers include: binders, lubricants, disintegrants, excipients, solubilizers, dispersants, stabilizers, suspending agents, colorants, and flavors for oral administration; buffers, preservatives, pain-relieving agents, solubilizers, isotonic agents, and stabilizers for injectable preparations; and bases, excipients, lubricants, and preservatives for topical administration. The pharmaceutical composition of the present invention may be formulated with the above-described pharmaceutically acceptable carriers. Examples of such formulations include: tablets, troches, capsules, elixirs, suspensions, syrups, and wafers for oral administration; and unit ampoules and multiple dosage forms for injectable preparations. The pharmaceutical composition of the present invention may also be formulated into other preparations, for example, solutions, suspensions, tablets, pills, capsules, and sustained release preparations.

Examples of carriers, excipients, and diluents suitable for the formulation of the pharmaceutical composition according to the present invention include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhyhydroxybenzoate, propylhydroxybenzoate, talc, magnesium stearate, and mineral oil. The pharmaceutical composition of the present invention may further include at least one additive selected from fillers, anticoagulants, lubricants, wetting agents, flavors, and preservatives.

The peptide of the present invention is used as an active ingredient of the health functional food composition. The food composition of the present invention may be used in combination with one or more active ingredients that are known as having anticancer activity. The food composition of the present invention may further include one or more sitologically acceptable food supplements. The health functional food composition of the present invention is intended to include compositions for all types of foods, such as functional foods, nutritional supplements, health foods, and food additives.

The types of food compositions may be prepared in various forms by general methods known in the art. For example, the health foods may be prepared into various formulations, such as tablets, pills, powders, capsules, gums, vitamin mixtures, juices, and drinks. The food composition of the present invention can be prepared into edible formulations by granulation, capsulation or pulverization. The food composition of the present invention may include one or more ingredients that are generally added for food production, for example, proteins, carbohydrates, fats, nutrients, and seasoning agents. For examples, the food composition of the present invention may be prepared into a drink. In this case, the food composition of the present invention may further include at least one additive selected from citric acid, high-fructose corn syrup, sugar, glucose, acetic acid, malic acid, fruit juice, jujube extract, and licorice extract. The food composition of the present invention may further include at least one food supplement selected from food additives generally used in the art, such as flavoring agents sweetening agents, colorants, fillers, and stabilizers. The food composition of the present invention may also contain a flavoring agent or a natural carbohydrate, like general beverages. Specific examples of such natural carbohydrates include monosaccharides, such as glucose and fructose, disaccharides, such as maltose and sucrose, polysaccharides, such as dextrins and cyclodextrins, and sugar alcohols, such as xylitol, sorbitol, and erythritol. Examples of suitable flavoring agents include natural flavoring agents (thaumatin and stevia extract (e.g., rebaudioside A and glycyrrhizin) and synthetic flavoring agents (saccharin and aspartame).

Furthermore, the food composition of the present invention may also contain at least one additive selected from: nutritional supplements, vitamins, minerals (electrolytes), sweeteners, such as synthetic and natural sweeteners, colorants, fillers (cheese and chocolate), pectic acid and its salts, alginic acid and its salts, organic acids, protective colloid thickeners, pH adjusting agents, stabilizers, preservatives, glycerin, alcohols, and carbonating agents used in carbonated beverages, which may be used independently or in combination.

Mode for Carrying out the Invention

The present invention will be explained in more detail with reference to the following examples. These examples are provided to assist in understanding the invention and are not intended to limit the scope of the invention.

EXAMPLE 1

Inhibition of CP2c-DNA Binding by Peptide 5

EXAMPLE 1.1

Five peptide motifs (Peptide 5, Peptide 8, Peptide 13, Peptide 21, and Peptide 31) interacting with mouse CP2c protein were identified using the phage display technique disclosed in the preceding research conducted by the present inventors.

EXAMPLE 1.2

To analyze whether the five peptides identified in Example 1.1 bind to CP2c in cells to affect the ability of CP2c to bind to DNA, DNA immunoprecipitation (DIP) assay was performed as disclosed in another preceding research conducted by the present inventors (Kim et al., A DNA immunoprecipitation assay used in quantitative detection of in vitro DNA-protein complex binding, *Analytical Biochemistry*. 2013; 441: 147-151).

In summary, the differentiation of a murine erythroid leukemia (MEL) cell line was induced by treatment with 5 mM hexamethylene bisacetamide (HMBA) and, on day 2 after differentiation, a cellular nuclear extract was separated. For the nuclear extract separation, first, $1 \times 10^6$ cells of the cell line were harvested and washed with PBS. After addition of 200 μl of nuclear extraction buffer A (10 mM HEPES, 10 mM KCl, 0.1 mM EDTA, 0.1 mM EGTA, 0.5 mM phenylmethylsulfonyl fluoride, protease inhibitor cocktail (Roche)), the reaction was allowed to proceed at 4° C. for 15 min. To the reaction mixture was added 0.6% NP-40. The resulting turbid solution was centrifuged and the supernatant was discarded. To the pellets remaining after the centrifugation was added 50 μl of nuclear extraction buffer C (20 mM HEPES, 400 mM NaCl, 1 mM EDTA, 1 mM EGTA, 1 mM phenylmethylsulfonyl fluoride, protease inhibitor cocktail (Roche)). The pellets were detached by tapping at 4° C. for 5-10 min, followed by centrifugation. Only the supernatant was used for subsequent experiments.

Subsequently, 5 μg of the nuclear extract and an [α-32p] dCTP-labeled DNA probe (a sequence corresponding to the common CP2c binding site present in mouse α-globin promoter and between −156 and −124 in the start codon of the α-globin gene, see the paper of Kim et al. for details of the sequence) were allowed to react with a binding buffer (4% glycerol, 10 mM Tris-HCl, 1 mM DTT, 1 mM EDTA, and 0.1% NP-40) for 15 min, and gradually increasing amounts (0.2, 0.5, and 1 μg) of the identified CP2c binding peptides (Peptide 5, Peptide 8, Peptide 13, Peptide 21, and Peptide 31) were added thereto. Then, the reaction was continued at room temperature for additional 15 min. To each reaction mixture was added 20 μl of 50% protein G-agarose bead suspension. The resulting mixture was reacted at 4° C. for 1 h to remove non-specific binding. After addition of 2 μg of anti-CP2c antibody (Cosmo genetech), the reaction was carried out at 4° C. for 10 h. 20 μl of 50% protein G-agarose bead suspension was added to the reaction product bound to the CP2c antibody. The reaction was carried out at 4° C. for 2 h. The reaction mixture was washed three times with cell lysis buffer (50 mM Tris-HCl, 150 mM NaCl, 1 mM EDTA, and 1 mM phenylmethylsulfonyl fluoride). To the CP2c-bound DNA probe was added an elution buffer (50 mM Tris-HCl, 10 mM EDTA, and 1% sodium dodecyl sulfate). The mixture was reacted at 65° C. for 1 h. The CP2c protein was removed from the DNA probe and the remaining amount of the DNA probe was measured using a scintillation counter.

In order to investigate which peptide sequences of the full-length CP2c sequence composed of a total of 6 regions interact with CP2c regions, the full-length CP2c sequence and sequences of various CP2c mutants in which the N- and C-termini of the CP2c sequence are depleted, are schematically shown in FIG. 1. FIG. 2 shows the binding affinities of the DNA-CP2c complexes measured by DNA immunoprecipitation (DIP) assay for the identified five CP2c-binding peptides (Peptide 5, Peptide 8, Peptide 13, Peptide 21, and Peptide 31). Referring to FIGS. 1 and 2, Peptide 5 specifically inhibited the CP2c-DNA binding in a concentration-dependent manner.

EXAMPLE 2

Inhibition of CP2c-DNA Binding by Peptides 5-1 and 5-2

CP2c-binding Peptide 5 composed of 12 amino acids was divided into Peptides 5-1 and 5-2, each of which is composed of 6 amino acids. Thereafter, the ability of Peptides 5-1 and 5-2 to inhibit the ability of CP2c to bind to DNA was analyzed by the same method as described in Example 1.

FIG. 3 shows the binding affinities of DNA-CP2c complexes by DIP assay for Peptide 5, Peptide 8, Peptide 5-1, and Peptide 5-2. Referring to FIG. 3, Peptide 8 and Peptide 5-1 negligibly inhibited the ability of CP2c to bind to DNA whereas Peptide 5-2 specifically inhibited the binding between CP2c and DNA, which is comparable to Peptide 5.

EXAMPLE 3

Structure and characterization of the invented synthetic peptides

Since the CP2c-binding peptides described in Examples 1-2 were very unstable, they tend to be degraded in culture solution upon treatment of cells during culture and do not easily penetrate the cell membrane upon treatment of cells, limiting their use in in vivo experiments. Accordingly, the CP2c-binding peptides need to be modified for their high cell penetrability. In an attempt to modify each peptide for high stability, acetyl and amide groups are attached to the N-and C-termini of the peptide, respectively. As modifications for high cell penetrability, Peptide 5C and Peptide 5-2C were prepared in which the iRGD peptide sequence (CRGDKGPDC (SEQ ID NO: 2)) binding to the neuropilin 1 receptor was attached to Peptide 5and Peptide 5-2, respectively. The peptide sequences of the modified peptides are listed in Table 1 (the peptides were synthesized in pepMic Co.,Ltd).

TABLE 1

| Peptide | SEQ ID NO | Peptide sequence | Theoretical pI | Number of (-) charged residues | Number of (+) charged residues | Predicted half-life (h) | Instability index | Relative hydrophilicity/hydrophobicity |
|---|---|---|---|---|---|---|---|---|
| 5 | 7 | HERRESNYPQRP | 8.75 | 2 | 3 | 3.5 | 115.33 (unstable) | -3.000 |
| 5C | 8 | Ac-HERRESNYPQRPCRGCRGDKGPDC-Amide | 8.31 | 4 | 5 | | | |
| 5-2 | 1 | NYPQRP | 8.75 | 0 | 1 | 1.4 | 93.10 (unstable) | -2.667 |
| 5-2C | 9 | Ac-NYPQRPCRGDKGPDC-Amide | 8.31 | 2 | 3 | | | |

EXAMPLE 4

Microscopic Observation for Growth Inhibition and Apoptosis Induction of Cancer Cell Lines by Peptide 5C and Peptide 5-2C

EXAMPLE 4.1

Microscopic Observation for Growth Inhibition and Apoptosis Induction of Normal Cell Lines and Cancer Cell Lines by Peptide 5C and Peptide 5-2C Liver cancer cell lines (HepG2, Hep3B), a human embryonic kidney cell line (293T), breast cancer cell lines (MCF-7, MDA-MB-231), blood tumor cell lines (K562, HEL, HL60), glioblastoma cell lines (U251, U373MG, U87MG), a mammary epithelial cell line (MCF10A), a lung epithelial cell line (BEAS2B), human mesenchymal stem cells (hMSCs), and mouse primary T cells (resting and activated T cells) were inoculated into 96-well plates at a density of 3,000 cells/well, supplemented with 50 µl of culture solution, and cultured at 37° C. and 5% $CO_2$ for 1 h. FQI1, Peptide 5C, and Peptide 5-2C were added at concentrations of 2 µM to the cell line-inoculated well plates and cultured at 37° C. and 5% $CO_2$ for 48 h. After completion of the culture, cells were observed under an inverted phase contrast microscope and their morphological changes were imaged.

FIG. 4a shows microscopy images of the cancer cell lines and FIG. 4b shows microscopy images of the normal cell lines and the bio-derived normal stem cells and differentiated cells. Referring to FIGS. 4a and 4b, FQI1 inhibited the growth of the normal cell lines as well as the cancer cell lines in a concentration-dependent manner and induced apoptosis, while Peptide 5C and Peptide 5-2C specifically inhibited the growth of the cancer cell lines and induced apoptosis without substantially affecting the normal cell lines.

EXAMPLE 4.2

Microscopic Observation of the Growth Inhibition of Cancer Cell Lines During Mammosphere Culture by Peptide 5-2C and Apoptosis Induction Cancer cell lines (MCF-7, 293T, MDA-MB-231) were inoculated at a density of $1\times10^4$ cells/ml into polyHEMA-coated 100 phi Petri dishes. Physiological saline and Peptide 5-2C were added at concentrations of 2 µM to culture vessels inoculated with the cell lines and cells were cultured at 37° C. and 5% $CO_2$ for 4 days. Cells were observed under an inverted phase contrast microscope once a day and their morphological changes were imaged. FIG. 4c shows microscopy images of the cell lines observed daily during mammosphere culture. Mammosphere culture of cancer cell lines is known to increase the number of cancer stem cells. Referring to FIG. 4c, the formation of mammospheres was effectively inhibited and cell growth was decreased by treatment with Peptide 5-2C, suggesting that Peptide 5-2C would inhibit the formation of cancer stem cells and induce apoptosis.

EXAMPLE 4.3

Microscopic Observation of the Growth Inhibition of Embryonic Stem Cell Line During Co-Culture on Embryonic Epithelial Cells and Apoptosis Induction by Peptide 5C and Peptide 5-2C Two colonies of a human embryonic stem cell line (H9) per well were inoculated into 96-well plates on which normal embryonic epithelial cells or embryonic epithelial cells fluorescently stained with rhodamine were plated, followed by culture for 24 h. Physiological saline, FQI1, Peptide 5C, and Peptide 5-2C were added with increasing concentration (0, 0.5, 1, 2, 3, and 10 µM) to well plates inoculated with the cell lines and cells were cultured at 37° C. and 5% $CO_2$ for 3 days. After completion of the culture, cells were observed under an inverted phase contrast microscope and their morphological changes were imaged.

FIG. 4d shows microscopy images of the colonies depending on the treatment concentration in the treated groups for 72 h (upper) and fluorescence microscopy images of representative embryonic stem cell colonies and fluorescently labeled co-cultured cells (lower). The right-most red framed images of FIG. 4d (upper) show higher magnifications of the boxes in the images of the 10 µM-treated groups.

Referring to FIG. 4d, for FQI1 and Peptide 5C, the embryonic stem cells and the co-cultured cell line died at concentrations of ≥3 μM. In contrast, for the groups treated with Peptide 5-2C, none of the embryonic stem cells and the co-cultured cells died even at concentrations of 10 M. These results suggest that Peptide 5-2C neither inhibits the growth of totipotent stem cells nor induces apoptosis in light of the results obtained in the normal cell lines in Example 4.1.

EXAMPLE 4.4

Microscopic Observation of the Growth Inhibition of Hematopoietic Progenitor Cells and Cells Derived Therefrom During Differentiation into Erythrocytes and Apoptosis Induction by Peptide 5C and Peptide 5-2C CD34+ hematopoietic progenitor cells (HPCs) and cells during differentiation into erythrocytes (3, 7, and 14 days after differentiation) were harvested from human peripheral blood and were then treated with physiological saline, FQI1, Peptide 5C, and Peptide 5-2 at increasing concentrations for 72 h. Cells were observed under an inverted phase contrast microscope and their morphological changes were imaged. The CD34+ hematopoietic progenitor cells were cultured in IMDM media containing 1% BSA. For differentiation induction into erythrocytes, cells were cultured with EPO, SCF, IL-3, and hydrocortisone for the first 7 days, and thereafter, cultured in media supplemented with EPO, SCF, and IL-3 only.

FIG. 4e shows microscopy images of the hematopoietic progenitor cells and the cells during differentiation induction into erythrocytes (3, 7, and 14 days after differentiation) in the treated groups. Referring to FIG. 4e, growth inhibition and apoptosis of the cells were not observed even when treated with all drugs, including Peptide 5-2C, at concentrations of up to 10 μM.

EXAMPLE 5

Growth Inhibition of Cancer Cell Lines and Apoptosis Induction by Peptide 5C and Peptide 5-2C: Quantitative Measurement of Cell Viabilities by MTT Assay

EXAMPLE 5.1

Analysis of Cell Viabilities of Liver Cancer Cell Lines when Treated with Peptide 5C and Peptide 5-2C Liver cancer cell lines (HepG2, Hep3B) were inoculated into 96-well plates at a density of 3000 cells/well, and then 50 μl of culture solution was added thereto. Cells were cultured at 37° C. and 5% $CO_2$ for 1 h. FQI1, Peptide 5C, Peptide 5-2C were added at concentrations of 0, 0.5, 2, 3, and 10 μM to the well plates inoculated with the liver cancer cell lines. Cells were cultured at 37° C. and 5% $CO_2$ for 24, 48, 72, and 96 h. After completion of the culture, the remaining culture solution was removed from the well plates, the cultures were diluted with MTT solution (3-(4, 5-dimethylthiazol-2-yl)-2,5-diphenyltetrazole bromide) to a final density of 500 μg/ml, and cells were cultured at 37° C. and 5% $CO_2$ for 3 h. The remaining MTT solution was removed and 150 μl of dimethyl sulfoxide (DMSO) was added. The reaction was carried out at room temperature for 20 min. After completion of the reaction, absorbance was measured using a microplate reader.

FIG. 5a shows the relative viabilities of HepG2 cell line and Hep3B cell line after one-time treatment with the peptides at increasing concentrations. Referring to FIG. 5a, Peptide 5C and Peptide 5-2C more effectively inhibited the growth of the liver cancer cell lines and induced apoptosis than FQI1.

EXAMPLE 5.2

Analysis of Cell Viabilities of Breast Cancer Cell Lines when Treated with Peptides 5C and 5-2C The procedure of Example 5.1 was repeated to determine whether FQI1, Peptide 5C, and Peptide 5-2C effectively inhibit the growth of breast cancer cell lines (MCF7, MDA-MB-231) and induced apoptosis.

FIG. 5b shows the relative viabilities of MCF7 cell line and MDA-MB-231 cell line when treated with the peptides at increasing concentrations. Referring to FIG. 5b, Peptide 5C and Peptide 5-2C more effectively inhibited the growth of the breast cancer cell lines and induced apoptosis than FQI1.

EXAMPLE 5.3

Analysis of Cell Viabilities of Glioblastoma Cell Lines when Treated with Peptides 5C and 5-2C The procedure of Example 5.1 was repeated to determine whether FQI1, Peptide 5C, and Peptide 5-2C effectively inhibit the growth of glioblastoma cell lines (U251, U87MG, U343) and induce apoptosis.

FIG. 5c shows the relative viabilities of U251 cell line, U87MG cell line and U343 cell line when treated with the peptides at increasing concentrations. Referring to FIG. 5c, Peptide 5C and Peptide 5-2C more effectively inhibited the growth of the glioblastoma cell lines and induced apoptosis than FQI1.

EXAMPLE 5.4

Analysis of Cell Viabilities of Human Blood Cancer Cell Lines when Treated with Peptides 5C and 5-2C The procedure of Example 5.1 was repeated to determine whether FQI1, Peptide 5C, and Peptide 5-2C effectively inhibit the growth of human blood cancer cell lines (K562, HEL, HL60) and induce apoptosis.

FIG. 5d shows the relative viabilities of K562 cell line, HEL cell line, and HL60 cell line when treated with the peptides at increasing concentrations. Referring to FIG. 5d, Peptide 5C and Peptide 5-2C slightly effectively inhibited the growth of the glioblastoma cell lines and induced apoptosis compared to FQI1.

EXAMPLE 5.5

Analysis of Cell Viabilities of Human Embryonic Kidney Cancer Cell Line when Treated with Peptides 5C and 5-2C The procedure of Example 5.1 was repeated to determine whether FQI1, Peptide 5C, and Peptide 5-2C effectively inhibit the growth of a human embryonic kidney cancer cell line (293T) and induce apoptosis.

FIG. 5e shows the relative viabilities of 293T cell line when treated with the peptides at increasing concentrations. Referring to FIG. 5e, Peptide 5C and Peptide 5-2C inhibited the growth of the glioblastoma cell lines and induced apoptosis similarly to FQI1.

EXAMPLE 5.6

Analysis of Cell Viabilities of Human Lung Epithelial Cell Line and Mammary Epithelial Cell Line when Treated with Peptides 5C and 5-2C The procedure of Example 5.1 was repeated to determine whether FQI1, Peptide 5C, and Peptide 5-2C effectively inhibit the growth of a human lung epithelial cell line (BEAS2B) and a mammary epithelial cell line (MCF10A) and induce apoptosis.

FIG. 5f shows the relative viabilities of MCF10A cell line and BEAS2B cell line when treated with the peptides at increasing concentrations.

BEAS2B and MCF10A cell lines are not cancer cells but normal epithelial cell lines that are generally used as normal control groups in experiments for anticancer agent screening. Referring to FIG. 5f, FQI1 showed concentration-dependent cytotoxicity while Peptide 5C showed lower cytotoxicity than FQI1 and Peptide 5-2C caused no substantial cytotoxicity even at a concentration of 10 μM.

EXAMPLE 5.7

Analysis of Cell Viabilities of Primarily Cultured Mouse T Lymphocytes when Treated with Peptides 5C and 5-2C Similar to the procedure of Example 5.1, a determination was made as to whether FQI1, Peptide 5C, and Peptide 5-2C effectively inhibit the growth of primarily cultured mouse T lymphocytes (resting and activated T lymphocytes) and induce apoptosis. In this experiment, spleens were excised from C57BL/6 mice, and tissue cells were separated by a physical method and passed through a 0.45 m mesh to obtain a cell suspension. CD4+ T cells were separated from the suspended cells using MACS. The separated T lymphocytes ($2.5\times10^5$ cells/well) were cultured in culture solution supplemented with 10% serum. The resulting T lymphocytes ($2.5\times10^5$ cells/well) in a resting state were activated by culture in a plate pre-coated with anti-CD3 and anti-CD28.

FIG. 5g shows the relative viabilities of the primarily cultured resting and activated T lymphocytes when treated with the peptides at increasing concentrations. Referring to FIG. 5g, no substantial cytotoxicities were observed even at concentrations of 10 μM in all treated groups, including Peptide 5-2C.

EXAMPLE 5.8

Analysis of Cell Viabilities of Human Mesenchymal Stem Cells when Treated with Peptides 5C and 5-2C The procedure of Example 5.1 was repeated to determine whether FQI1, Peptide 5C, and Peptide 5-2C effectively inhibit the growth of human mesenchymal stem cells (hMSC) and induce apoptosis.

FIG. 5h shows the relative viabilities of hMSC cell line when treated with the peptides at increasing concentrations. Like BEAS2B and MCF10A cell lines, hMSC cells are not cancer cells but normal cells. Referring to FIG. 5h, FQI1 showed concentration-dependent cytotoxicity while Peptide 5-2C caused no substantial cytotoxicity even at high concentrations.

EXAMPLE 5.9

Analysis of Cell Viabilities of Human Embryonic Stem Cells when Treated with Peptides 5C and 5-2C Similar to the procedure of Example 5.1, a determination was made as to whether FQI1, Peptide 5C, and Peptide 5-2C effectively inhibit the growth of human embryonic stem cells (hESCs) that maintain pluripotency through co-culture with mouse embryonic fibroblasts (MEFs). In this experiment, two colonies of hESCs (H9 cells) per well were co-cultured in 96-well plates plated with MEF cells whose growth had been inhibited by treatment with mitomycin C (MMC). MEF cells labeled with rhodamine were often used to distinguish them from hESC-derived cells.

FIG. 5i shows the relative viabilities of unlabeled hESCs (upper) and rhodamine-labeled hESCs (lower) when treated with the peptides at increasing concentrations. Since the epithelial cells showed no toxicity to all treated substances in Example 5.6, the cell viabilities measured in this experiment could be considered as the viabilities of hESCs. Referring to FIG. 5i, FQI1 showed concentration-dependent cytotoxicity, Peptide 5C caused slight cytotoxicity at high concentrations, and Peptide 5-2C caused no substantial cytotoxicity even at high concentrations.

EXAMPLE 5.10

Analysis of Cell Viabilities of Human Hematopoietic Progenitor Cells and Cells Derived Therefrom During Differentiation into Erythrocytes when Treated with Peptides 5C and 5-2C Similar to the procedure of Example 5.1, a determination was made as to whether FQI1, Peptide 5C, and Peptide 5-2C effectively inhibit the growth of cancer cells and induce apoptosis in CD34+ hematopoietic progenitor cells (HPCs) and cells during differentiation into erythrocytes (days 3, 7, and 14 after differentiation). In this experiment, cells were prepared and cultured in the same manner as in Example 4.4.

FIG. 5j shows the relative viabilities of hematopoietic progenitor cells and cells derived therefrom during differentiation induction into erythrocytes (days 3, 7, and 14 after differentiation). Referring to FIG. 5j, no substantial cytotoxicities were observed even when treated with all drugs, including Peptide 5-2C, at concentrations of up to 10 μM.

FIG. 5k shows images of the well plates 76 h (Example 5.10) and 96 h after the peptide treatment among the data of MTT assay conducted in Examples 5a to 5j.

EXAMPLE 6

Analysis of Expression Levels of CP2c Protein in Various Cancer Cell Lines

EXAMPLE 6.1

The expression levels of CP2c protein in a total of 19 cell lines, including 6 colon cancer cell lines, 6 lung cancer cell lines, 3 breast cancer cell lines, 3 glioblastoma cell lines, and one cervical cancer cell line were compared and analyzed by Western blotting. $1\times10^6$ cells of each of the cell lines during culture were collected and washed with phosphate-buffered saline (PBS). A cell extract was obtained using cell lysis buffer (50 mM Tris-HCl, pH 7.4, 150 mM NaCl, 1 mM EDTA, pH 8, 1% Triton X-100, 1 mM phenylmethylsulfonyl fluoride, protease inhibitor cocktail (Roche)). A predetermined amount of the protein was electrophoresed on a SDS-polyacrylamide gel (7.5%-15%), transferred to a PVDF membrane, and reacted in 5% blocking solution for 1 h. The protein was reacted with anti-CP2c Ab (Cosmo gentech) as a primary antibody at room temperature for 1 h and was treated with horseradish peroxidase-conjugated anti-rabbit Ab (Abcam) as a secondary antibody at room temperature for 1 h. An ECL system (Amersham-GE Healthcare) was used for detection.

The experimental results are shown in FIG. 6a. Referring to FIG. 6a, CP2c was overexpressed in various cancer cell lines.

EXAMPLE 6.2

The procedure of Example 6.1 was repeated to confirm the expression levels of CP2c protein in blood cancer cell lines (MEL, K562, HEL, HL60), liver cancer cell lines (HepG2, Hep3B), an epidermoid carcinoma cell line (A431), a colon cancer cell line (HCT116), and epithelial cell lines (293T, BEAS2B, MCF10A) and hMSC cell lines from various tissue sources.

The experimental results are shown in FIG. 6b. Referring to FIG. 6b, CP2c was overexpressed in various cancer cell lines but such a phenomenon was not observed in normal cell lines, such as hMSC.

EXAMPLE 7

Measurement of $IC_{50}$ Values of Peptide 5-2C in Various Cancer Cell Lines after Peptide 5-2C Treatment

EXAMPLE 7.1

Measurement of $IC_{50}$ Values of Peptide 5-2C in Various Cancer Cell Lines and Normal Cell Lines after Peptide 5-2C Treatment Based on the results of the MTT experiments conducted on various cancer cell lines in Example 5, $IC_{50}$ values after Peptide 5-2C treatment for 48 h were calculated using the Graph Prism Pad 6 program ($IC_{50}$ refers to the concentration of each substance needed to reduce the number of cells by 50%).

FIG. 7a shows graphs for calculating $IC_{50}$ values of Peptide 5-2C after treatment of each cell line with Peptide 5-2C for 48 h and the calculated $IC_{50}$ values. Referring to FIG. 7a, Peptide 5-2C did not substantially affect the growth inhibition of the normal control cell lines and the induction of apoptosis but had $IC_{50}$ values of an average of ~1 M with slight differences in various cancer cell lines.

EXAMPLE 7.2

Measurement of $IC_{50}$ Values of Peptide 5-2C after Peptide 5-2C Treatment for Different Periods of Time After one-time treatment of various glioblastoma cell lines (U343, U373MG, U251, and U87MG) with Peptide 5-2C, $IC_{50}$ values were measured with time using the Graph Prism Pad 6 program.

FIG. 7b shows graphs for calculating $IC_{50}$ values at 48 h and 96 h after each cell line was treated once with Peptide 5-2C and the calculated $IC_{50}$ values. Referring to FIG. 7b, the $IC_{50}$ values after 48 h were similar to those after 96 h, suggesting that the Peptide 5-2C maintained its effect on the inhibition of cell growth and the induction of apoptosis for 96 h.

EXAMPLE 7.3

Measurement of $IC_{50}$ Values of FQI1, Peptide 5C, and Peptide 5-2C in MCF10A Cell Line and BEAS2B Cell Line after Treatment with the Peptides Based on the results of the MTT experiments conducted on the lung epithelial cell line (BEAS2B) and the mammary epithelial cell line (MCF10A) in Example 5, $IC_{50}$ values after FQI1, Peptide 5C, and Peptide 5-2C treatment were calculated using the Sigma plot program.

FIG. 8 shows graphs for calculating $IC_{50}$ values after treatment with FQI1, Peptide 5C, and Peptide 5-2C and the calculated $IC_{50}$ values. Referring to FIG. 8, the treatment of the normal control cell lines with FQI1 inhibited cell growth and induced apoptosis, similarly to the treatment with Peptide 5C (the $IC_{50}$ values of FQI1 were substantially the same as those of Peptide 5C in MCF10A but the $IC_{50}$ values of Peptide 5C were 1.5 times higher than those of FQI1 in BEAS2B) but the treatment with Peptide 5-2C did not substantially affect the growth inhibition of the normal control cell line and the induction of apoptosis.

EXAMPLE 8

Comparison and analysis of growth inhibition of cancer cell lines and induction of apoptosis by Peptides 5-2C and 5-2D: Quantitative measurement of cell viabilities by MTT assay Peptide 5-2C is a variant of Peptide 5-2 (SEQ ID NO: 1) whose terminal Pro residue is bonded with the RGD peptide sequence (CRGDKGPDC; SEQ ID NO: 2) binding to the neuropilin 1 receptor. This modification increases the cell penetrability of the peptide. As demonstrated in the above examples, Peptide 5-2 can specifically inhibit the growth of cancer cell lines and can induce apoptosis. It is necessary to use a complex of Peptide 5-2 and another cell-penetrating peptide in order to confirm that these effects of Peptide 5-2C on specific growth inhibition of cancer cells and the induction of apoptosis are dependent on Peptide 5-2 rather than on the RGD sequence. To this end, Peptide 5-2D was synthesized in which the dNP2 peptide sequence (KIKKVKKK-GRKGSKIKKVKKKGRKGG (SEQ ID NO: 4); Lim et al., Nat Commun (2015) 6, 8244), which is known to have the ability to penetrate blood-brain barrier (BBB) and cells, is attached to the N-terminal Asn residue of Peptide 5-2. The cell viabilities of cancer cell lines when treated with Peptide 5-2D were quantitatively measured by MTT assay and were compared with the effects of Peptide 5-2C.

EXAMPLE 8.1

Analysis of Cell Viabilities of Breast Cancer Cell Lines when Treated with Peptide 5-2D The procedure of Example 5.1 was repeated to determine whether Peptide 5-2D effectively inhibits the growth of breast cancer cell lines (MCF7, MDA-MB-231) and induces apoptosis.

FIG. 9a shows the relative viabilities of MDA-MB-231 cell line and MCF7 cell line when treated with physiological saline as a negative control, Peptide 5-2C as a positive control, and Peptide 5-2D at increasing concentrations. Referring to FIG. 9a, Peptide 5-2D inhibited the growth of the breast cancer cell lines and efficiently induced apoptosis, similarly to Peptide 5-2C.

EXAMPLE 8.2

Analysis of Cell Viabilities of Glioblastoma Cell Lines when Treated with Peptide 5-2D The procedure of Example 5.1 was repeated to determine whether Peptide 5-2D effectively inhibits the growth of glioblastoma cell lines (U343, U87MG) and induces apoptosis.

FIG. 9b shows the relative viabilities of U343 cell line and U87MG cell line when treated with physiological saline as a negative control, Peptide 5-2C as a positive control, and Peptide 5-2D at increasing concentrations. Referring to FIG. 9b, Peptide 5-2D inhibited the growth of the glioblastoma cell lines and efficiently induced apoptosis, similarly to Peptide 5-2C.

EXAMPLE 8.3

Analysis of Cell Viabilities of Colon Cancer Cell Lines when Treated with Peptide 5-2D The procedure of Example 5.1 was repeated to determine whether Peptide 5-2D effectively inhibits the growth of colon cancer cell lines (HCT116, HT29) and induces apoptosis.

FIG. 9c shows the relative viabilities of HCT116 cell line and HT29 cell line when treated with physiological saline as a negative control, Peptide 5-2C as a positive control, and Peptide 5-2D at increasing concentrations. Referring to FIG. 9c, Peptide 5-2D inhibited the growth of the glioblastoma cell lines and efficiently induced apoptosis, similarly to Peptide 5-2C.

EXAMPLE 8.4

Analysis of Cell Viabilities of Human Embryonic Kidney Cancer Cell Line and Liver Cancer Cell Line when Treated with Peptide 5-2D The procedure of Example 5.1 was repeated to determine whether Peptide 5-2D effectively inhibits the growth of a human embryonic kidney cancer cell line (293T) and a liver cancer cell line (HepG2) and induces apoptosis.

FIG. 9d shows the relative viabilities of 293T cell line and HepG2 cell line when treated with physiological saline as a negative control, Peptide 5-2C as a positive control, and Peptide 5-2D at increasing concentrations. Referring to FIG. 9d, Peptide 5-2D inhibited the growth of the human embryonic kidney cancer cell line and liver cancer cell line and efficiently induced apoptosis, similarly to Peptide 5-2C.

EXAMPLE 8.5

Analysis of Cell Viabilities of Human Blood Cancer Cell Lines when Treated with Peptide 5-2D The procedure of Example 5.1 was repeated to determine whether Peptide 5-2D effectively inhibits the growth of human blood cancer cell lines (U937, Jurkat, HL60, HEL) and induces apoptosis.

FIG. 9e shows the relative viabilities of U937 cell line, Jurkat cell line, HL60 cell line, and HEL cell line when treated with physiological saline as a negative control, Peptide 5-2C as a positive control, and Peptide 5-2D at increasing concentrations. Referring to FIG. 9e, Peptide 5-2D inhibited the growth of the human embryonic kidney cancer cell line and the liver cancer cell line and efficiently induced apoptosis, similarly to Peptide 5-2C.

EXAMPLE 8.6

Analysis of Cell Viabilities of Human Mammary Epithelial Cell Line and Lung Epithelial Cell Line when Treated with Peptide 5-2D The procedure of Example 5.1 was repeated to determine whether Peptide 5-2D effectively inhibits the growth of a mammary epithelial cell line (MCF10A) and a lung epithelial cell line (BEAS2B) and induces apoptosis.

FIG. 9f shows the relative viabilities of MCF10A cell line and BEAS2B cell line when treated with physiological saline as a negative control, Peptide 5-2C as a positive control, and Peptide 5-2D at increasing concentrations. Referring to FIG. 9f, Peptide 5-2D did not affect the growth of the mammary epithelial cell line and the lung epithelial cell line and apoptosis, similarly to Peptide 5-2C.

FIG. 9g shows images of the well plates 96 h after the peptide treatment among the data of MTT assay conducted in Examples 8.1 to 8.6.

EXAMPLE 9

Measurement of $IC_{50}$ Values of Peptide 5-2D in Various Cancer Cell Lines after Peptide 5-2D Treatment Based on the results of the MTT experiments conducted on various cancer cell lines and normal cell lines in Example 8, $IC_{50}$ values after Peptide 5-2C treatment for 48 h were calculated using the Graph Prism Pad 6 program ($IC_{50}$ refers to the concentration of each substance needed to reduce the number of cells by 50%).

FIG. 10 shows graphs for calculating $IC_{50}$ values 48 h after each cell line was treated once with Peptides 5-2C and 5-2D and the calculated $IC_{50}$ values. Referring to FIG. 10, Peptide 5-2D did not substantially affect the growth inhibition of the normal control cell lines and the induction of apoptosis but had $IC_{50}$ values of an average of ~3 M with slight differences in various cancer cell lines, similarly to Peptide 5-2C.

In conclusion, Peptide 5-2 can specifically inhibit the growth of cancer cells and induce apoptosis when a cell penetration-promoting peptide, such as RGD or dNP2, is connected to the C- or N-terminus of Peptide 5-2.

EXAMPLE 10

Analysis of the Inhibitory Effect of Peptide 5-2C Treatment on Tumor Growth in Mouse Models Transplanted with Various Cancer Cell Lines and Prediction of General Physiological Toxicity

EXAMPLE 10.1

Analysis of Inhibitory Effect of Peptide 5-2C Treatment on Tumor Growth in Mouse Models Transplanted with Glioblastoma Cell Line (U343) and Prediction of General Physiological Toxicity U343 glioblastoma cell line ($2.5 \times 10^6$ cells/50 μl) was injected subcutaneously into the backs of 5-week-old male BALB/C nude mice (n=6/group), Peptide 5-2C (3 mg/kg) was directly injected into the tumor sites every three days from the time when the tumor sizes increased to about 8 mm², the body weights of the mice and the volumes of the tumors were measured, the mice were sacrificed on day 70 after the peptide injection, and the tumors, blood, and major organs were excised. The tumor sizes were measured using a vernier calipers and the tumor volumes were calculated by (major axis×minor axis²)/2. Peripheral blood was collected from the ophthalmic artery of each mouse using a microcapillary coated with EDTA and stored in a sample tube coated with 5.4 mg EDTA. The tumors and the major organs were excised by dissection. The collected blood was subjected to a fundamental complete blood cell count (CBC) using a Coulter LH 750 Hematology analyzer. After the tumors were weighed, the tumors and the major organs were stained with 4% formaldehyde. Tissue slices were prepared through paraffin section and stained with hematoxylin/eosin. Acquired data were statistically analyzed using the Excel program.

FIG. 11 shows the ability of Peptide 5-2C to inhibit tumor growth and the physiological properties of Peptide 5-2C in mouse models transplanted with U343 glioblastoma cell line. Specifically, FIG. 11a shows the volumes of the tumors during the experimental period, FIG. 11b shows changes in the body weight of the mice, FIG. 11c shows images of the mice on day 70 after the peptide administration, FIG. 11d shows images of the excised tumors, FIG. 11e shows the weights of the tumors excised from the mice and their average values, FIG. 11f shows various standard blood indices of the mice in the control and peptide-treated groups, and FIG. 11g shows H/E-stained images of the major organs (spleens, livers, lungs, and kidneys). Referring to FIGS. 11a to 11g, there were no differences in the weight of the mice, the major CBC indices of the mice, and the histologic/anatomic characteristics of the major organs when Peptide 5-2C was directly administered to tumor sites, compared to when only physiological saline was administered (control). However, the tumor volume and weight were reduced by ~60%. Taken together, Peptide 5-2C (3 mg/kg) efficiently inhibits the growth of tumor without causing special physiological toxicity in tumor models transplanted with a glioblastoma cell line.

EXAMPLE 10.2

Analysis of Inhibitory Effect of Peptide 5-2C Treatment on Tumor Growth in Mouse Models Transplanted with Epidermoid Carcinoma Cell Line (A431) and Prediction of General Physiological Toxicity A431 cell line (5×10⁶ cells/100 µl) was injected subcutaneously into the backs of 7-week-old male BALB/C nude mice (n=4/group), Peptide 5-2C (1×IC$_{50}$; 1.7 mg/kg, 2×IC$_{50}$; 3.5 mg/kg) was injected every other day into the mice through the tail veins a total of five times from the time when the tumor sizes increased to about 50 mm², the tumor volumes were measured, the mice were sacrificed on day 13 after the peptide injection, and the tumors and major organs were excised. After the tumors were weighed, the tumors and the major organs were stained with 4% formaldehyde. Tissue slices were prepared through paraffin section and stained with hematoxylin/eosin. Acquired data were statistically analyzed using the Excel program.

FIGS. 12a to 12d show the ability of Peptide 5-2C to inhibit tumor growth and physiological properties of Peptide 5-2C in the mouse models transplanted with the A431 human epidermoid carcinoma cell line. FIG. 12a shows the volumes of the tumors during the experimental period, FIG. 12b shows images of the mice and the excised tumors, FIG. 12c shows the weights of the tumors excised from the mice in the groups and their average values, and FIG. 12d shows H/E-stained images of the major organs (spleens, livers, lungs, blood vessels, and muscles) of the groups. Referring to FIGS. 12a to 12d, when Peptide 5-2C was injected every other day through the veins a total of five times, the volume and weight of the tumors derived from the A431 epidermoid carcinoma cell line were reduced by ≥70% and ≥60%, respectively, and there were no significant changes in the histologic/anatomic characteristics of the major organs. Taken together, these results indicate that Peptide 5-2C can efficiently inhibit the growth of tumors derived from a epidermoid carcinoma cell line via intravenous administration.

EXAMPLE 10.3

Analysis of Inhibitory Effect of Peptide 5-2C Treatment on Tumor Growth in Mouse Models Transplanted with Breast Cancer Cell Line (MDA-MB-231) and Prediction of General Physiological Toxicity MDA-MB-231 cell line (LM1 cells; 1×10⁶ cells/40 µl), whose metastasis to lung tissue had been confirmed, was injected into the mammary fat pads of 12-week-old female BALB/C nude mice (n=5/group), Peptide 5-2C (1×IC$_{50}$; 1.7 mg/kg=52 g/mouse, 2×IC$_{50}$; 3.5 mg/kg=104 µg/mouse) was injected every three days into the mice through the tail veins a total of five times from the time when the tumor sizes increased to about 50 mm², the tumor volumes were measured, the mice were sacrificed on day 30 after the peptide injection, and the tumors and major organs were excised. The collected blood was subjected to a fundamental CBC using a Coulter LH 750 Hematology analyzer. After the tumors were weighed, the tumors and the major organs were stained with 4% formaldehyde. Tissue slices were prepared through paraffin section and stained with hematoxylin/eosin. Acquired data were statistically analyzed using the Excel program.

FIGS. 13a to 13d show the ability of Peptide 5-2C to inhibit metastasis to lung tissue and tumor growth, and physiological properties of Peptide 5-2C in the animal models transplanted with MDA-MB-231 cell line (LM1 cells) capable of metastasizing to lung tissue. FIG. 13a shows images of the mice sacrificed on day 30 after the injection of the breast cancer cell line and the excised tumors, FIG. 13b shows the weights of the tumors excised from the mice in the control and peptide-treated groups and their average values, FIG. 13c shows means and standard deviations of the number of the tumor foci metastasized to the lung in the control and peptide-treated groups, and FIG. 13d shows the CBC indices in the control and peptide-treated groups. Referring to FIGS. 13a to 13d, when Peptide 5-2C was injected into the tumor mouse models transplanted with MDA-MB-231 breast cancer cell line, whose metastasis to lung tissue had been confirmed, through the veins, the tumor weights were reduced by ~30% and the number of the tumor foci metastasized to the lung was reduced by ~50% compared to those in the control group. On the other hand, the CBC indices in the Peptide 5-2C-injected groups were similar to those in the control group but the number of leukocytes in the control mice transplanted with the breast cancer cell line amounted to twice that in the normal mice and the number of leukocytes in the mice injected with Peptide 5-2C was close to the normal value (FIG. 13d). In conclusion, Peptide 5-2C is effective in inhibiting the growth of tumors and the metastasis of cancer in mouse models transplanted with breast cancer cells. In addition, Peptide 5-2C can recover an increased WBC value caused by the transplantation of cancer cells to a normal level without causing any hematological toxicity.

EXAMPLE 11

Analysis of Transcriptional Activity of CP2c when Treated with Peptide 5C and Peptide 5-2C 293T cells were inoculated into a 12-well plate at a density of $1 \times 10^5$ cells/well. 12 h after inoculation, cells were transfected with combinations of a reporter vector (the wild-type reporter links the enhancer sequence of the GATA-1 gene including twice repeated CP2c-binding sites to the upstream of the luciferase gene and Mut 1/3, Mut 2/4, and Mut 1-4 reporters cause mutations of the CP2c binding sites present in the enhancer sequence) and various Flag-CP2c, HA-CP2b, and HA-PIAS1 expression vectors by using the effectene method. After 1-h culture, cells were treated with FQI1, Peptide 5C, and Peptide 5-2C at concentrations of 2 µM, followed by 48-h culture. Cells were harvested and lysed in 250 µl of passive cell lysis buffer (Promega) to obtain an extract. 20 µl of the cell extract and a dual-luciferase assay kit (Promega) were used to measure the activity of the labeled luciferase gene in GLOMAX (Promega) (the expression of each expression vector was confirmed by Western blotting).

The results are shown in FIGS. 14a to 14e. Specifically, FIG. 14a shows the results obtained using the reporter vector having the normal CP2c target sequence shown in FIG. 14e, FIGS. 14b to 14d show the results obtained using mutants 2/4, 1/3, and 1-4, respectively. FIG. 14e shows the normal sequence and the sequences of the mutants. Referring to FIGS. 14a to 14e, Peptide 5C and Peptide 5-2C effectively inhibit CP2c-mediated transcriptional activity compared to FQI1. This effect was not found in the mutant in which CP2c binding sites were mutated and was specifically observed in not only the site where CP2c homotetramer (J Biol Chem, 1994; Genes Cells, 1998) acts but also in the sequence where CP2c/CP2b/PIAS1 heterohexamer (CBP complex, *Nucleic Acids Res*. Kang et al., 2010) acts.

EXAMPLE 12

Analysis of Mechanisms of Action of Cancer Cell-Specific Growth Interruption and Apoptosis Induction by Peptide 5-2C Treatment

EXAMPLE 12.1

Analysis of Cell Cycle in Various Cancer Cell Lines when Treated with Peptide 5-2C $5 \times 10^5$ cells of each of MEL, K562, MCF-10A, and MDA-MB-231 cell lines were inoculated into 100 mm dishes. 24 h after inoculation, cells were treated with Peptide 5-2C such that the final concentrations were 0, 1, 2, 3, and 10 µM. 48 h after Peptide 5-2C treatment, cells were collected by trypsin treatment. Thereafter, $1 \times 10^6$ cells were suspended in 0.5 ml PBS and dissociated into single cells by pipetting. The cell suspension was transferred to a centrifugal tube containing 4.5 ml of 70% ethanol and allowed to stand at 4° C. for 2 h to immobilize the cells. A cell sediment was obtained by centrifugation, washed with 5 ml of PBS solution, sufficiently suspended in 1 ml of PI staining solution, and stained in the dark for 30 min. Cell fluorescence was measured in BD FACSAria and cell cycle was analyzed using the software provided from the same company.

FIGS. 15a to 15c show the results of cell cycle analysis for various cell lines (MEL, K562, MCF-10A, MDA-MB-231) by FACS at 48 h after treatment of the cell lines with Peptide 5-2C at various concentrations of 0, 1, 2, 3, and 10 µM in order to analyze the influence of Peptide 5-2C on cell cycle. Specifically, FIG. 15a shows the distributions of cells depending on the amount of DNA during FACS, FIG. 15b shows quantified cell distributions in cell cycle phases, and FIG. 15c shows enlarged distributions of cells in subG1 phase showing apoptosis. Referring to FIGS. 15a to 15c, when treated with Peptide 5-2C, no substantial changes in cell cycle were observed in MCF-10A cell line where growth interruption and apoptosis induction are not likely to occur. In contrast, in MEL cell line where growth interruption and apoptosis are induced when treated at high concentrations (10 µM), the number of cells in the subG1 phase was significantly increased only at high concentrations upon FACS analysis. In contrast, in K562 cell line and MDA-MB-231 cell line where growth interruption and apoptosis are induced sensitively in response to Peptide 5-2C, the number of cells in the S phase was decreased, the number of cells in the G2/M phase was increased, and an increase in the number of cells in the subG1 phase was dependent on the concentration of Peptide 5-2C. From these results, it can be concluded that the phenomena of cancer cell-specific growth interruption and apoptosis induction by Peptide 5-2C result from the interruption of cell growth by inhibiting the conversion to the G2/M phase of cell cycle.

EXAMPLE 12.2

Analysis of Expression Profiles of Cell Cycle-Related Marker Gene in MCF7 Cell Line when Treated with Peptide 5-2C at Different Concentrations for Different Periods of Time $1 \times 10^5$ cells of MCF7 breast cancer cell line were inoculated into a 6-well plate. 24 h after inoculation, cells were treated with Peptide 5-2C at a final concentration of 2 µM. After 0, 24, 48, and 72 h, cell extracts were collected in the same manner as in Example 6. Western blotting was performed using various antibodies against cell cycle-related marker genes. On the other hand, cell extracts were obtained from the groups treated with Peptide 5-2C at final concentrations of 1, 2, and 3 µM for 48 h and Western blotting was performed in the same manner.

FIGS. 16a to 16d show the expression profiles of cell cycle-related marker genes when MCF7 cell line was treated with Peptide 5-2C at different concentrations for different periods of time. Specifically, FIG. 16a shows time-dependent expression profiles of various cell cycle-related marker gene proteins when treated with 2 µM Peptide 5-2C for 72 h, as determined by Western blotting, FIG. 16b shows the expression profiles of various cell cycle-related marker gene proteins after treatment with Peptide 5-2C at various concentrations (0, 1, 2, and 3 µM) for 48 h, as determined by Western blotting, and FIGS. 16c and 16d show quantified changes in the expression of the marker gene proteins in FIGS. 16a and 16b, respectively. Referring to FIGS. 16a to 16d, as the Peptide 5-2C treatment time and concentration increased, the expressions of Cyclin E, p21, and p53 increased gradually and the expressions of CDK1 and Cyclin B1 decreased gradually, indicating that Peptide 5-2C interrupted the cell cycle in the G2 phase.

EXAMPLE 12.3

Expression Profiles of Apoptosis-Related Marker Gene in MDA-MB-231 Cell Line and MCF7 Cell Line Depending on Peptide 5-2C Treatment Time and Concentration In the same manner as in Example 12.2, MDA-MB-231 and MCF7 breast cancer cell lines were treated with physiological saline and 2 µM Peptide 5-2C for up to 72 h. After 0, 24, 48, and 72 h, cell extracts were collected. Western blotting was performed using various antibodies against cell cycle-related marker genes.

FIG. 17 show time-dependent expression profiles of apoptosis-related marker gene proteins after treatment of MDA-MB-231 cell line and MCF7 cell line with 2 µM Peptide 5-2C. Referring to FIG. 17, as the Peptide 5-2C treatment time increased, the expressions of the anti-apoptosis-related marker genes MCL1 and BCL2 were decreased gradually, the expressions of the apoptosis promotion-related marker genes Bim, Bax, Bak, cleaved Cas3 and Cas8, and pro-Cas11 were increased and the expressions of pro-Cas3, pro-cas8, pro-Cas9, pro-Cas12 were decreased gradually. These results can lead to the conclusion that as the Peptide 5-2C treatment time increases, the expressions of the anti-apoptosis-related marker genes are decreased and the expressions of the apoptosis promotion-related marker genes are increased, resulting in the induction of apoptosis. It is assumed that increasing p53 induces both intrinsic apoptosis through the mitochondria pathway and apoptosis through apoptosis receptor-mediated pro-Cas8 activation (Ashkenazi A, Nat rev, 2008).

EXAMPLE 12.3

Electron Microscopic Analysis of Cell Morphology of MDA-MB-231 Cell Line and MCF10A Cell Line when Treated with Peptide 5-2C $1.5 \times 10^6$ cells of MDA-MB-231 cell line and $5 \times 10^5$ cells of MCF10A cell line were inoculated into 100 mm dishes. 1 h after inoculation, cells were treated with physiological saline, 2 µM Peptide 5-2C, and 2 µM FQI1. After culture for 24 and 48 h, cells were collected. The culture solution was centrifuged and surface adherent cells were collected by trypsin treatment. The collected cells were washed once with physiological saline. The cell sediment was directly treated twice with 2.5% aqueous glutaraldehyde solution (each for 10 min). Samples for electron microscopy were prepared and imaged in accordance with general methods.

FIG. 18 represents electron microscopy images showing cell morphologies 24 h and 48 h after treatment of MDA-MB-231 cell line and MCF10A cell line with 2 µM Peptide 5-2C. Cells treated with physiological saline and cells treated with 2 µM FQI1 were used as negative and positive controls, respectively. Referring to FIG. 18, for MDA-MB-231 cell line where growth interruption and apoptosis induction were found to be sensitive to Peptide 5-2C, significantly different intracellular structural abnormalities were observed in the Peptide 5-2C-treated group compared to in the FQI1-treated group. For MCF10A cell line where no growth interruption and apoptosis induction were found by Peptide 5-2C treatment, no intracellular structural abnormalities were observed in the Peptide 5-2C-treated group, whereas intracellular structural abnormalities began to appear at 24 h after the peptide treatment and considerable nuclear disruption was observed at 48 h after the peptide treatment in the FQI1-treated group. Taken together, tumor cell-specific growth interruption and apoptosis induction by Peptide 5-2C are based on different mechanisms from those by FQI1. In the normal mammary epithelial cell line MCF10A, no intracellular structural modification was caused by Peptide 5-2C treatment whereas serious intracellular structural modification was caused by FQI1. These results are in good agreement with the results obtained in Examples 4, 5, 7, and 8.

EXAMPLE 13

Analysis of Tracking of Intracellular Migration Pathways of FITC Fluorescence-Labeled Peptide 5-2C in MDA-MB-231 Cell Line To verify that cancer cell-specific growth interruption and apoptosis induction are caused by Peptide 5-2C and iRGD simply assists in the cell penetration of the peptide, three FITC fluorescently labeled peptides (FITC-iRGD, FITC-5-1C, and FITC-5-2C) were synthesized. In the same manner as in Example 5.1, MDA-MB-231 cell line was treated with physiological saline and the FITC-conjugated peptides for 96 h and cell viabilities and $IC_{50}$ value values were calculated by MTT assay. For reference, Peptide 5-1 composed of 6 first amino acids from the N-terminus residue of Peptide 5 has no influence on the ability of CP2c to bind to DNA (see FIG. 3). Each FITC-conjugated peptide was treated for 30 min under the same conditions as described in Example 5.1. The wells were washed three times with physiological saline and replaced with new ones. Thereafter, time-lapse phase contrast microscopy images and fluorescence microscopy images were taken for 24 h (at 1, 2, 4, 8, 12, and 24 h after peptide treatment). The cell images and fluorescence images were merged using the Photoshop program.

FIGS. 19a to 19d are graphs confirming intracellular migration pathways of the FITC-conjugated Peptide 5-2C in MDA-MB-231 cell line with the passage of time. Specifically, FIG. 19a shows changes in cell growth rate after MDA-MB-231 cell line was treated with physiological saline and FITC-conjugated-iRGD, FITC-5-1C, and FITC-5-2C peptides at concentrations of 0, 0.5, 1, 2, 3, and 10 µM for 96 h, as determined by MTT assay, FIG. 19b shows graphs for calculating $IC_{50}$ values of the treated groups at 48 h after the treatment and the calculated $IC_{50}$ values, FIG. 19c shows images of well plates showing examples of MTT assay at 96 h, and FIG. 19d shows images showing time-dependent intracellular distributions of the FITC-conjugated peptides (each 2 µM) for 24 h after treatment with the peptides. Referring to FIGS. 19a to 19d, only the FITC-conjugated Peptide 5-2C inhibited cell growth and its $IC_{50}$ values were similar to those of non-FITC-conjugated Peptide 5-2C. This demonstrates that cancer cell-specific growth interruption and apoptosis induction are caused by Peptide 5-2C and iRGD simply assists in the cell penetration of the peptide. Cell penetration began to occur at 2 h after peptide treatment and cell-penetrated Peptide 5-2C was accumulated in the nucleus whereas the other peptides (iRGD and Peptide 5-1C) remained in the cytoplasm or were easily degraded after 8 h.

EXAMPLE 14

Identification of CP2c Protein Region Interacting with Peptide 5-2C and Amino Acids in the Region From the results obtained in the foregoing examples, it can be assumed that cancer cell-specific growth interruption and apoptosis induction caused by Peptide 5-2 are because Peptide 5-2 binds to CP2c to impede the binding of CP2c to a regulation site of a target gene where characteristics of cancer cells are exhibited. To support this assumption, a CP2c protein region with which Peptide 5-2C interacts and amino acids in the region directly binding to Peptide 5-2C need to be identified. Thus, an attempt was made to obtain mutant CP2c proteins in which polar amino acids present in the CP2c region binding with Peptide 5 shown in FIG. 1 were substituted with Ala and analyze the binding of the mutant CP2c proteins with Peptide 5-2C by enzyme-linked immunosorbent assay (ELISA). To facilitate this analysis, Peptide 5-2CB was synthesized in which biotin tag is bonded to the C-terminal Pro residue of Peptide 5-2C. To confirm whether Peptide 5-2CB induces cancer cell-specific growth interruption and apoptosis, like Peptide 5-2C, MTT assay was conducted on two different batches of Peptide 5-2CB in MDA-MB-231 cell line and MCF7 cell line by the same method as in Example 5.1. $IC_{50}$ values were also calculated from the results of MTT assay. To obtain 19 mutant CP2c proteins in which polar amino acids present in the CP2c region binding with Peptide 5-2C were substituted with Ala, oligonucleotides having sequences encoding the corresponding mutant amino acids were synthesized and site-directed mutagenesis was carried out. The base sequences encoding the mutant CP2c genes were cloned into the pGEX4 vector and mutant GST-fusion CP2c proteins were purified using beads bound with antibody against GST-tag. The binding of the mutant CP2c to CP2c binding sites (CP2c binding base sequence on the alpha-globin promoter) was confirmed in the same manner as in Example 1. The binding of each mutant CP2c to Peptide 5-2CB was confirmed by direct ELISA, which was used to identify CP2c-binding peptides through the phage display technique (Kang et al., FEBS J, 2005; 272: 1265-1277). The binding between Peptide 5-2CB and each mutant CP2c protein was confirmed using HRP-conjugated streptavidin beads capable of recognizing biotin tag in Peptide 5-2CB. Tertiary structure models were predicted based on the Rosetta modeling algorism for 306-396 amino acid region of CP2c and important amino acids for target DNA binding and Peptide 5-2C binding were obtained using the Swissprot program.

FIGS. 20*a* to 20*d* compare the influence of Peptide 5-2CB (biotin-tagged Peptide 5-2C) on cancer cell survival with that of Peptide 5-2C. Specifically, FIG. 20*a* shows the relative viabilities of MDA-MB-231 cell line after one-time treatment with Peptide 5-2C and two different batches of Peptide 5-2CB at increasing concentrations, FIG. 20*b* shows images of well plates 96 h after the peptide treatment, FIG. 20*c* shows graphs for calculating $IC_{50}$ values at 48 h after treatment of MDA-MB-231 cell line with each peptide and the calculated $IC_{50}$ values, and FIG. 20*d* shows graphs for calculating $IC_{50}$ values at 48 h after treatment of MCF7 cell line with each peptide and the calculated $IC_{50}$ values. Referring to FIGS. 20*a* to 20*d*, Peptide 5-2CB induced cancer cell-specific cell growth interruption and apoptosis, similarly Peptide 5-2C, and had $IC_{50}$ values similar to Peptide 5-2C. These results indicate that Peptide 5-2CB can be efficiently used for experiments shown in FIGS. 21*a* to 21*d*.

FIGS. 21*a* to 21*d* show the results of a series of experiments for identifying important amino acids for DNA binding or Peptide 5-2C binding in CP2c protein regions to which Peptide 5-2C binds. Specifically, FIG. 21*a* shows a list of binding regions of Peptide 5-2C and 19 GST-fusion mutants produced by substituting polar amino acids in the amino acid sequence of the site with alanine, FIG. 21*b* shows the results of DNA-IP for the binding of GST-fusion proteins purified from the mutants overexpressed in *E. coli* using GST antibody beads with a DNA probe of a CP2c binding site present in a radioactively labeled alpha-globin promoter, FIG. 21*c* shows the results of direct ELISA for the binding of purified GST-fusion proteins with Peptide 5-2C, and FIG. 21*d* shows important amino acids for DNA binding and Peptide 5-2C binding to tertiary structures, which were predicted based on the Rosetta modeling algorism for 306-396 amino acid region of CP2c. Referring to FIGS. 21*a* to 21*d*, 322-389 amino acid region of CP2c protein including alpha-helices recognizes a target base sequence of CP2c and is involved in binding with Peptide 5-2. Particularly, E332, R339, R341 and R387 amino acids are important for binding to DNA while E332, R339, R341 and R347 amino acid are important for binding to Peptide 5-2. Taken together, Peptide 5-2 competitively binds to important E332, R339, and R341 for binding to the target DNA base sequence of CP2c, making it impossible for CP2c to bind to the target base sequence. As a result, Peptide 5-2 inhibits the expression of CP2c target gene involved in the conversion to the G2/M phase of cell cycle to induce cancer cell-specific growth interruption and apoptosis.

INDUSTRIAL APPLICABILITY

Peptide 5-2 of the present invention penetrates the cell membranes of cancer cells with very high efficiency and is capable of specific binding to CP2c. Therefore, the peptide of the present invention inhibits the activity of CP2c, thus being effective in treating cancer through cell growth inhibition and apoptosis induction in various CP2c-mediated cancer cells.

The invention claimed is:

1. A peptide that binds to transcription factor CP2c and has the amino acid sequence Asn-Tyr-Pro-Gln-Arg-Pro (SEQ ID NO: 1),
   wherein the peptide does not include the amino acid sequence His-Glu-Arg-Arg-Glu-Ser (SEQ ID NO: 5) bonded to the N-terminal Asn residue of the peptide of SEQ ID NO: 1.

2. The peptide according to claim 1, wherein acetyl and amide groups are bonded to the N-terminal Asn residue and the C-terminal Pro residue of the peptide having the amino acid sequence set forth in SEQ ID NO: 1, respectively.

3. The peptide according to claim 1, wherein the C-terminal Pro residue of the peptide having the amino acid sequence set forth in SEQ ID NO: 1 is bonded with a peptide having the amino acid sequence Cys-Arg-Gly-Asp-Lys-Gly-Pro-Asp-Cys (SEQ ID NO: 2).

4. The peptide according to claim 3, wherein acetyl and amide groups are linked to the N-terminal Asn residue of the peptide having the amino acid sequence set forth in SEQ ID NO: 1 and the C-terminal Cys residue of the peptide having the amino acid sequence set forth in SEQ ID NO: 2, respectively.

5. The peptide according to claim 1, wherein the C-terminal Pro residue and the N-terminal Asn residue of the peptide having the amino acid sequence set forth in SEQ ID NO: 1 is linked with the peptide having the amino acid sequence set forth in SEQ ID NO: 2 and a peptide having the amino acid sequence Lys-Cys-Lys-Gly-Gly-Ser-Gly-Gly-Ser (SEQ ID NO: 3),
   wherein the first amino acid Lys and the third amino acid Lys represent 6-aminohexanoic acid, and the N-terminal Lys residue of the peptide having the amino acid sequence set forth in SEQ ID NO: 3 is linked with fluorescein isothiocyanate (FITC).

6. The peptide according to claim 5, wherein an amide group is bonded to the C-terminal Cys residue of the peptide having the amino acid sequence set forth in SEQ ID NO: 2.

7. The peptide according to claim 1, wherein the N-terminal Asn residue of the peptide having the amino acid sequence set forth in SEQ ID NO: 1 is linked with a peptide having the amino acid sequence Lys-Ile-Lys-Lys-Val-Lys-Lys-Lys-Gly-Arg-Lys-Gly-Ser-Lys-Ile-Lys-Lys-Val-Lys-Lys-Lys-Gly-Arg-Lys-Gly-Gly (SEQ ID NO: 4).

8. The peptide according to claim 7, wherein acetyl and amide groups are bonded to the N-terminal Lys residue of the peptide having the amino acid sequence set forth in SEQ ID NO: 4 and the C-terminal Pro residue of the peptide having the amino acid sequence set forth in SEQ ID NO: 1, respectively.

9. The peptide according to claim 3, wherein biotin-tagged Lys is bound to the ε-NH$_2$ of the C-terminal Cys residue of the peptide having the amino acid sequence set forth in SEQ ID NO: 2.

10. The peptide according to claim 9, wherein acetyl and amide groups are bonded to the N-terminal Asn residue of the peptide having the amino acid sequence set forth in SEQ ID NO: 1 and the biotin-tagged C-terminal Lys bound to the ε-NH$_2$ of the C-terminal Cys residue of the peptide having the amino acid sequence set forth in SEQ ID NO: 2, respectively.

11. A pharmaceutical composition comprising the peptide according to claim 1 as an active ingredient.

12. A health functional food composition comprising the peptide according to claim 1 as an active ingredient.

\* \* \* \* \*